(12) United States Patent
Stucky et al.

(10) Patent No.: US 10,770,699 B2
(45) Date of Patent: Sep. 8, 2020

(54) STABLE BROMINE CHARGE STORAGE IN POROUS CARBON ELECTRODES USING TETRAALKYLAMMONIUM BROMIDES FOR REVERSIBLE SOLID COMPLEXATION

(71) Applicant: The Regents of the University of California, Oakland, CA (US)

(72) Inventors: Galen D. Stucky, Santa Barbara, CA (US); Brian Evanko, Goleta, CA (US); Seung Joon Yoo, Goleta, CA (US); Jason Lipton, San Rafael, CA (US); Shannon W. Boettcher, Eugene, OR (US); David Xiulei Ji, Happy Valley, OR (US); Xingfeng Wang, Corvallis, OR (US)

(73) Assignees: The Regents of the University of California, Oakland, CA (US); Oregon State University, Corvallis, OR (US); University of Oregon, Eugene, OR (US)

( * ) Notice: Subject to any disclaimer, the term of this patent is extended or adjusted under 35 U.S.C. 154(b) by 413 days.

(21) Appl. No.: 15/601,811

(22) Filed: May 22, 2017

(65) Prior Publication Data
US 2017/0256366 A1 Sep. 7, 2017

Related U.S. Application Data

(63) Continuation-in-part of application No. 14/692,695, filed on Apr. 21, 2015, now Pat. No. 9,728,344.
(Continued)

(51) Int. Cl.
*H01M 2/08* (2006.01)
*H01G 9/008* (2006.01)
(Continued)

(52) U.S. Cl.
CPC ............ *H01M 2/08* (2013.01); *C07D 213/06* (2013.01); *C08K 5/19* (2013.01); *H01G 11/02* (2013.01);
(Continued)

(58) Field of Classification Search
CPC ........ H01G 11/02; H01G 11/04; H01G 11/16; H01G 11/32; H01G 11/62; H01G 11/64;
(Continued)

(56) References Cited

U.S. PATENT DOCUMENTS 5,082,594 A * 1/1992 Tsuzuki .................. C04B 41/00
  252/502
8,518,572 B2 8/2013 Kim et al.
(Continued)

*Primary Examiner* — Brittany L Raymond
(74) *Attorney, Agent, or Firm* — Gates & Cooper LLP

(57) ABSTRACT

Electrolytes for use in electric double-layer capacitors (EDLCs; often referred as supercapacitors or ultracapacitors) are disclosed. In one example, the electrolyte comprises viologen in both the anolyte and the catholyte (with bromide). In another example, the electrolyte comprises viologen (in the anolyte) and tetraalkylammonium with bromide (in the catholyte), wherein the tetraalkylammonium is used to achieve solid complexation of bromine in the activated carbon of the cathode. In a third example, a zinc bromine/tetraalkylammonium supercapacitor/battery hybrid is disclosed. Also disclosed is a corrosion resistant bipolar pouch cell that can be used with the electrolyte embodiments described herein.

19 Claims, 49 Drawing Sheets a. Positive current collector
b. Positive electrode
c. Separator
d. Negative electrode
e. Insulating plastic spacer
f. Heat seal
g. Negative current collector
h. Bipolar current collector

Related U.S. Application Data

(60) Provisional application No. 61/982,236, filed on Apr. 21, 2014.

(51) Int. Cl.

| | |
|---|---|
| *H01G 9/00* | (2006.01) |
| *H01G 9/10* | (2006.01) |
| *H01G 11/30* | (2013.01) |
| *H01G 11/62* | (2013.01) |
| *H01G 11/64* | (2013.01) |
| *H01G 11/68* | (2013.01) |
| *H01G 11/70* | (2013.01) |
| *H01G 11/78* | (2013.01) |
| *C07D 213/06* | (2006.01) |
| *C08K 5/19* | (2006.01) |
| *H01G 11/32* | (2013.01) |
| *H01G 11/02* | (2013.01) |
| *H01G 11/72* | (2013.01) |
| *H01G 11/04* | (2013.01) |
| *H01G 11/16* | (2013.01) |

(52) U.S. Cl.
CPC ............ *H01G 11/32* (2013.01); *H01G 11/62* (2013.01); *H01G 11/64* (2013.01); *H01G 11/72* (2013.01); *H01G 11/04* (2013.01); *H01G 11/16* (2013.01); *Y02E 60/13* (2013.01)

(58) Field of Classification Search
CPC ........ H01G 11/72; H01G 11/78; H01G 11/80; H01G 11/82; H01M 2/08; C07D 213/06; C08K 5/19; Y02E 60/13
See application file for complete search history.

(56) References Cited

U.S. PATENT DOCUMENTS

| | | | |
|---|---|---|---|
| 9,196,425 B2 | 11/2015 | Stucky et al. | |
| 2005/0058889 A1* | 3/2005 | Goishihara | H01M 4/04 429/94 |
| 2007/0158185 A1* | 7/2007 | Andelman | C02F 1/4691 204/229.7 |
| 2011/0116211 A1* | 5/2011 | Watanabe | H01G 9/016 361/502 |
| 2011/0287316 A1 | 11/2011 | Lu et al. | |
| 2014/0329126 A1* | 11/2014 | Ho | H01M 4/13 429/128 |
| 2015/0062777 A1 | 3/2015 | Stucky et al. | |

* cited by examiner

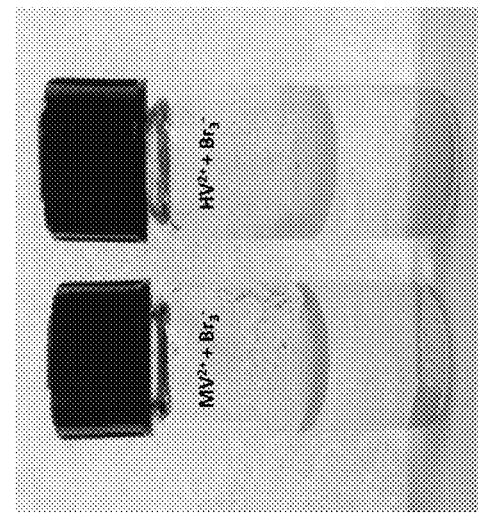
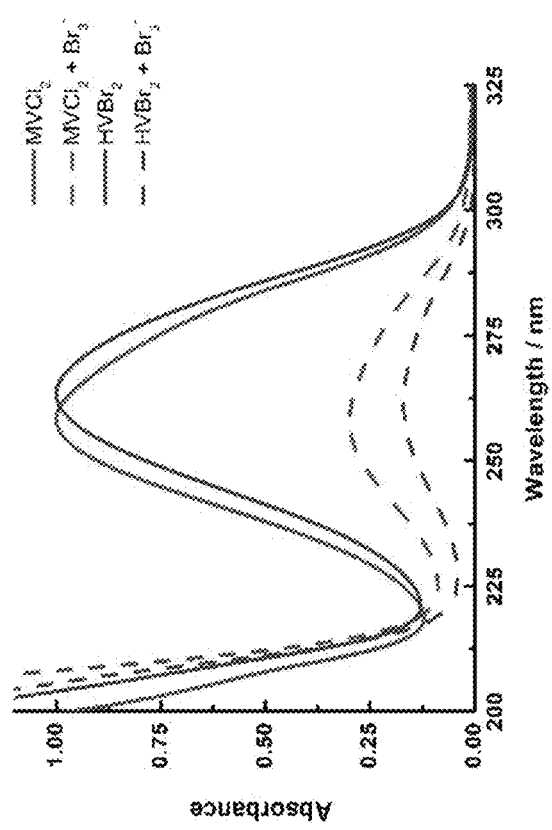
Figure 3(a)
Figure 3(b)

Figure 8

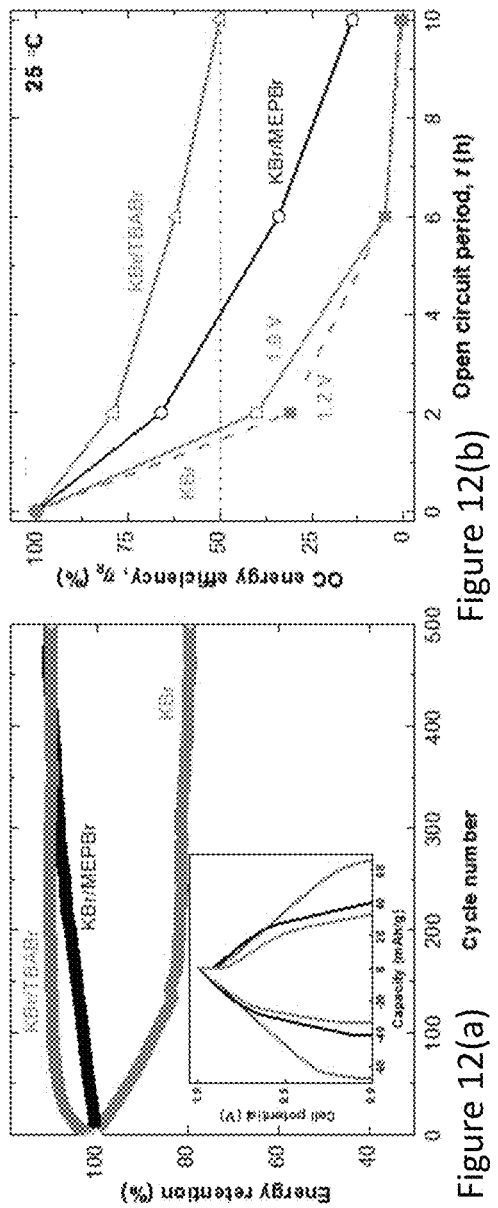
Figure 12(b)
Figure 12(a)
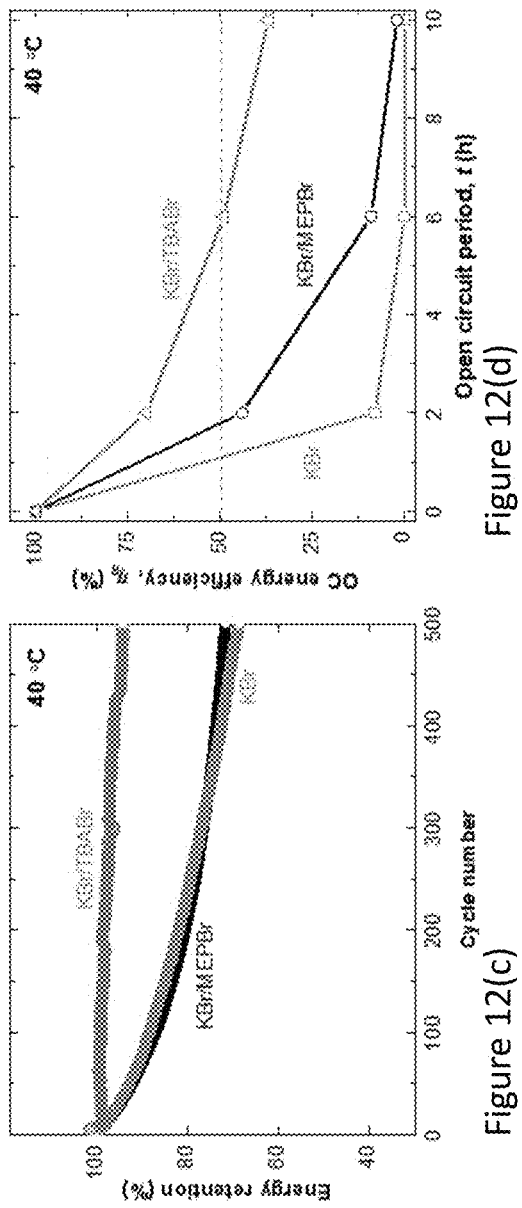
Figure 12(d)
Figure 12(c)

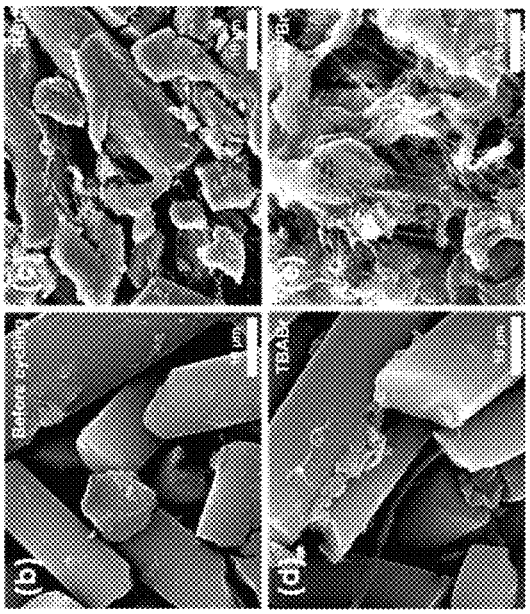
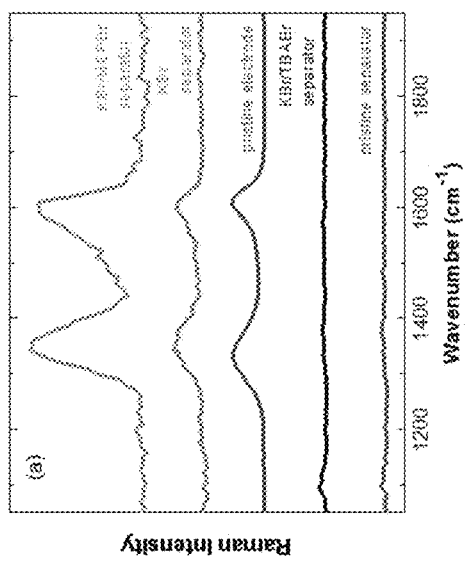
Figure 13(a)
Figure 13(b)
Figure 13(c)
Figure 13(d)
Figure 13(e)

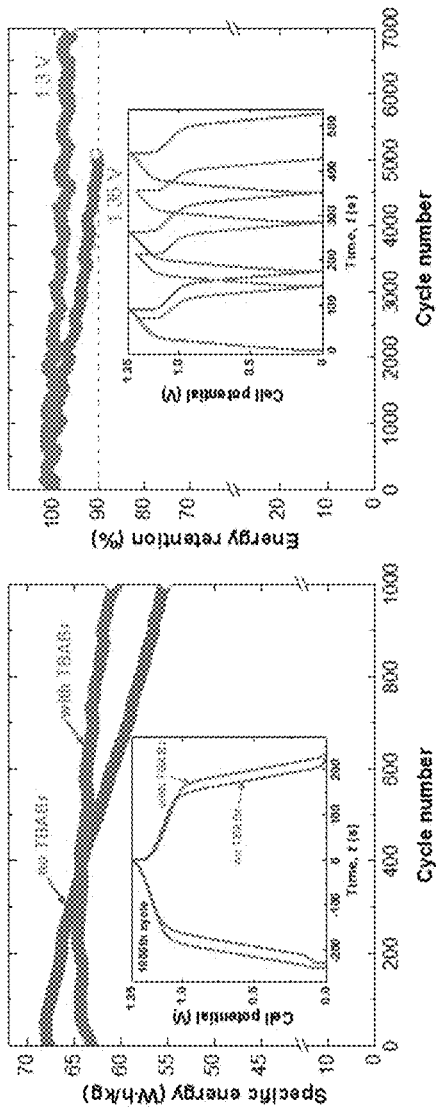
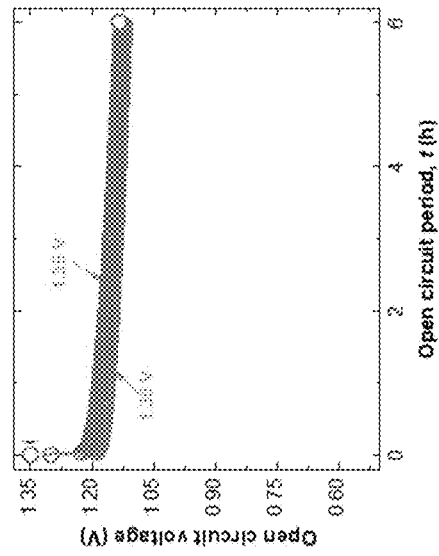
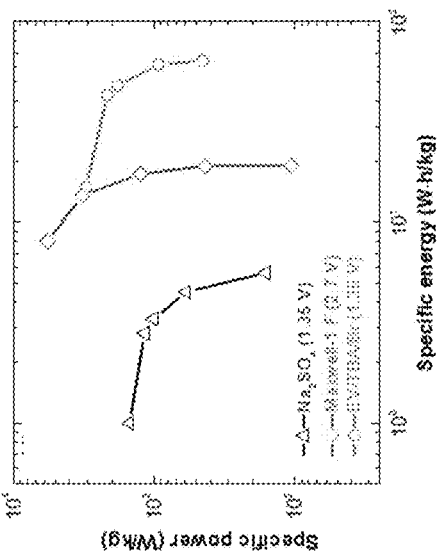
Figure 16(a)
Figure 16(b)
Figure 16(c)
Figure 16(d)

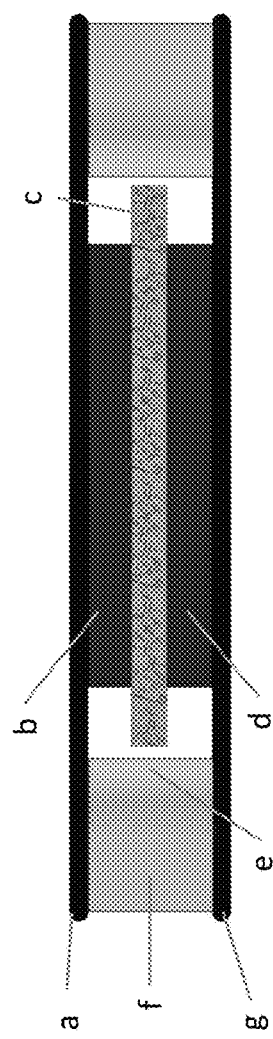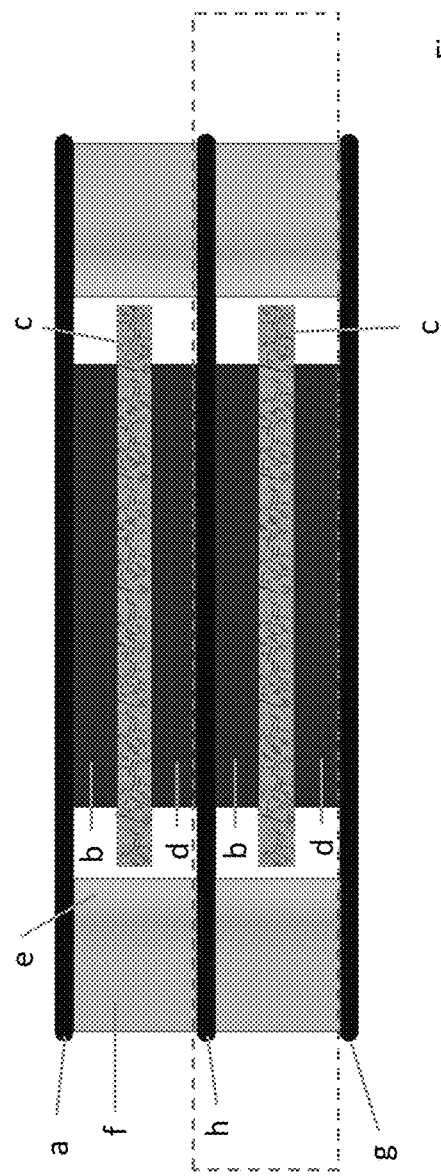
Figure 30(a)
Figure 30(b)
Repeated n ≥ 1 times
a. Positive current collector
b. Positive electrode
c. Separator
d. Negative electrode
e. Insulating plastic spacer
f. Heat seal
g. Negative current collector
h. Bipolar current collector

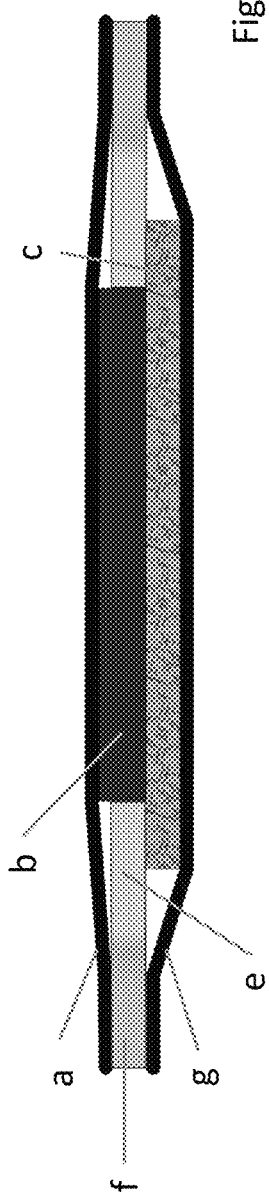
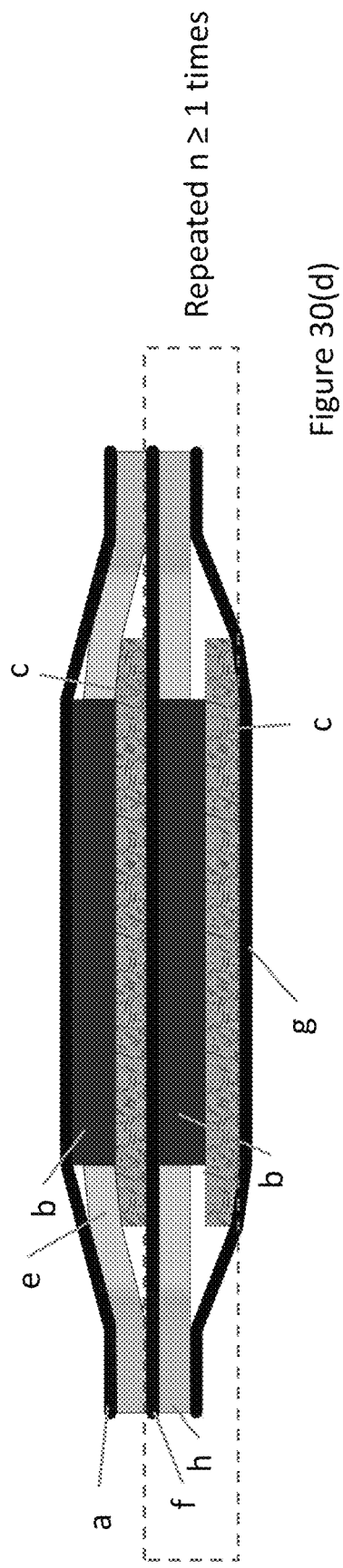
Figure 30(c)
Figure 30(d)
Repeated n ≥ 1 times
a. Positive current collector
b. Positive electrode
c. Separator
d. Negative electrode
e. Insulating plastic spacer
f. Heat seal
g. Negative current collector
h. Bipolar current collector a. Positive current collector
b. Positive electrode
c. Separator
d. Negative electrode
e. Insulating plastic spacer
f. Heat seal
g. Negative current collector
h. Bipolar current collector
i. Microporous polyethylene separator

STABLE BROMINE CHARGE STORAGE IN POROUS CARBON ELECTRODES USING TETRAALKYLAMMONIUM BROMIDES FOR REVERSIBLE SOLID COMPLEXATION

CROSS REFERENCE TO RELATED APPLICATIONS

This application is a continuation-in-part under 35 U.S.C. § 120 and § 365(c) of co-pending U.S. Utility patent application Ser. No. 14/692,695, filed Apr. 21, 2015, by Galen D. Stucky, Brian Evanko, Nicholas Parker, David Vonlanthen, David Auston, Shannon Boettcher, Sangeun Chun, Xiulei Ji, Bao Wang, Xingfeng Wang and Raghu Subash Chandrabose, entitled "ENERGY STORAGE DEVICE INCLUDING REDOX-ENHANCED ELECTROLYTE," (UC Ref 2014-716), which application claims the benefit under 35 U.S.C. Section 119(e) of U.S. Provisional Patent Application No. 61/982,236, filed May 21, 2014, by Galen D. Stucky, Brian Evanko, Shannon Boettcher, Sangeun Chun, Xiulei Ji, and Bao Wang, entitled "HIGH VOLTAGE REDOX ELECTROLYTES FOR ENHANCED ELECTROCHEMICAL CAPACITOR PERFORMANCE AND REDUCED SELF-DISCHARGE," Attorney's Docket No. 30794.548-US-P1 (2014-716);

all of which applications are incorporated by reference herein.

STATEMENT REGARDING FEDERALLY SPONSORED RESEARCH AND DEVELOPMENT

This invention was made with Government support under Grant No. DE-AR0000344, awarded by the U.S. Department of Energy (DOE). The Government has certain rights in this invention.

BACKGROUND OF THE INVENTION

1. Field of the Invention
This invention relates to energy storage devices.
2. Description of the Related Art
(Note: This application references a number of different references as indicated throughout the specification by one or more reference numbers in superscripts, e.g., [x]. A list of these different references ordered according to these reference numbers can be found below in the section entitled "References." Each of these references is incorporated by reference herein.)

Electric double-layer capacitors (EDLCs), interchangeably referred to as supercapacitors or ultracapacitors, are capable of storing and discharging energy quickly due to a physical ion adsorption/desorption mechanism in the Helmholtz layer.[1,2] Compared to EDLCs using non-aqueous electrolytes, EDLCs with nonflammable aqueous electrolytes are in principle safer, and provide higher power density due to their having a lower ionic resistance.[1,3-5] However, the energy density of aqueous EDLCs is limited by the narrow electrochemical potential window of water compared to counterparts with organic electrolytes or ionic liquids.[6-8] The grand challenge for aqueous EDLCs is to increase specific energy without compromising specific power and cycling stability. A number of hybrid and pseudocapacitive systems have been developed that utilize different charge storage mechanisms in addition to, and/or in place of, electric double-layer capacitance to increase energy density.[9-15]

One such approach to enhance the energy density is to replace the inert electrolytes of conventional EDLCs with redox-active electrolytes that enable faradaic charge storage.[16-23] High-energy redox electrochemical capacitors (ECs) must concurrently utilize a catholyte and an anolyte (dual-redox enhanced electrochemical capacitors; dual-redox ECs) to maximize faradaic energy storage.[19,23,25,26,36] Compared with the construction of nanostructured solid-state redox-active electrode materials, liquid-state redox-active electrolytes are easier to prepare and be scaled up, and should be compatible with the carbon electrodes that are currently mass-produced for commercial EDLCs.

In order to design redox-active electrolyte systems, redox couples should exhibit fast and reversible electron transfer and not engage in irreversible side reactions and/or degradation over repeated charge/discharge cycles. Additionally, the cross-diffusion of soluble redox couples that causes low Coulombic efficiency and fast self-discharge must be eliminated. The use of ion-selective membrane separators to mitigate self-discharge has been reported,[24] but such membranes are costly, and primarily for that reason are not practical for commercial applications. Electrostatic attraction has also been proposed as a mechanism to retain redox couples at the surface of oppositely charged electrodes, but was shown to have only a minor effect on the suppression of self-discharge rates.[25,26]

Halogens ($I^-$ and $Br^-$) are promising aqueous redox-active species as they are inexpensive, electrochemically reversible redox couples with high solubility.[22,25,27-31] In comparison to iodide, bromide has a higher standard reduction potential (0.81 V vs SCE; $E_{I_3^-/I^-}°=0.3$ V) that further increases energy density. However, this advantage is offset by the corrosive and volatile nature of bromine generated at the positive electrode. Furthermore, soluble $Br_3^-$ diffuses to the negative electrode, which causes low Coulombic efficiency and fast self-discharge, as well as possible irreversible oxidation or bromination of the anode or anolyte.[32,33] In aqueous bromine flow batteries, asymmetric quaternary ammonium salts such as methyl ethyl pyrrolidinium bromide (MEPBr; 1-ethyl-1-methylpyrrolidinium bromide) or methyl ethyl morpholinium bromide (MEMBr; 4-ethyl-4-methylmorpholinium bromide) are commonly used to complex $Br_2/Br_3^-$ as an oily-liquid phase.[34,35] This complexation reduces the reactivity and vapor pressure of bromine while maintaining a mobile, liquid state for flow-system compatibility. However, this approach does not address the cross-diffusion and poor Coulombic efficiency.[32] Standard bromine flow batteries avoid these limitations by storing the charged liquid complex in a separate tank away from the cell stack, but this practice is not feasible for non-flow systems, such as in redox-enhanced electrochemical capacitors (redox ECs). Alternatively, ion-exchange membrane separators can be used, but these materials are expensive and require addressing significant sealing challenges to be effective in a practical device. In short, a fundamental need is to store $Br_3^-$ in non-flow energy storage systems in a manner that (1) reduces the unwanted chemical reactivity and vapor pressure of bromine but at the same time (2) suppresses cross-diffusion and self-discharge by (3) a simple and affordable mechanism. Embodiments of the present invention satisfy this need.

SUMMARY OF THE INVENTION

The present disclosure reports on surprising and unexpected uses of viologen, tetraalkylammonium, and/or zinc in electrolytes for EDLCs.

In a first embodiment, the electrolyte includes a first redox couple comprising bromine and a second redox couple comprising a viologen. During charging, the electrolyte evolves into a catholyte including the first redox couple and an anolyte including the second redox couple. When charged, the charge is stored in faradaic reactions with the first and second redox couples in the electrolyte and in a double-layer capacitance of a porous carbon material that comprises at least one of the electrodes.

In various embodiments, the viologen has the structure:

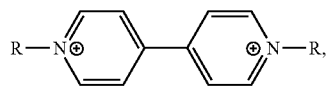

wherein R is an alkyl. Examples of the viologen anolyte include, but are not limited to, ethyl viologen, butyl viologen, pentyl viologen, hexyl viologen, and other viologens. It is preferable that the alkyl comprises at least 4 carbon atoms, in order to strongly adsorb to the carbon electrode when reduced.

In yet further embodiments, the catholyte also comprises a viologen. The viologen in the catholyte may be the same as, or different from, the viologen in the anolyte. Examples of the viologen in catholyte include, but are not limited to, hexyl viologen and pentyl viologen. In one or more examples, the viologen in the catholyte is a complexing agent that forms a complex with the bromine.

The present disclosure further describes, for the first time, tetrabutylammonium-induced, reversible solid complexation of the $Br^-/Br_3^-$ redox couple in aqueous redox ECs. Systematic studies show that this solid complex is retained in the pores of the high-surface-area carbon electrodes (without the use of an expensive ion-selective membrane to separate cell compartments) upon charging, suppressing cross-diffusion and preventing unwanted chemical reactivity that would cause electrode degradation, and thereby dramatically improving cycling stability and self-discharge relative to traditional oily-liquid-phase bromine complex. Furthermore, the present disclosure reveals the underlying cause of the irreversible capacity loss that occurs when the uncomplexed $Br^-/Br_3^-$ redox couple is used in aqueous redox ECs with activated carbon electrodes.

Building upon these findings, a high-performance and stable aqueous redox EC was designed. The compatibility and comparative $Br_3^-$ complexing capacity was investigated to demonstrate the utility of bromide catholyte and the complexation strategy in such a system. In one illustrative embodiment, the use of readily available tetrabutylammonium bromide as an additive, and a dual-redox EC that utilizes bromide and a highly soluble ethyl viologen (EV) as an anolyte, produced a specific energy of ~64 W·h/kg (at 1 A/g and normalized to the dry mass of both positive and negative electrode), representing a ~230% improvement over commercial non-aqueous electric double-layer capacitors. In addition, the EC comprising tetrabutylammonium bromide as an additive maintains stability over 7000 cycles.

In yet a further embodiment, the electrolyte includes any tetraalkylammonium bromide as described herein forming a solid complex with bromine. In yet a further embodiment, the second redox couple comprises zinc. In various implementations using zinc, the electrolyte does not need to include a viologen. Such an electrolyte may be used in supercapacitors or supercapacitor/battery hybrids.

In one or more embodiments wherein the electrolyte comprises a zinc halide, the energy storage device, comprises a cathode and an anode in contact with an electrolyte including zinc halide; and tetraalkylammonium complexing agent (e.g., tetrabutylammonium bromide or cetyltrimethylammonium bromide) on the cathode. During charging, the zinc from the zinc halide plates onto the anode and the halogen in the halide oxidizes so as to form a solid complex with the tetraalkylammonium on the cathode.

The present disclosure further describes an energy storage device comprising a pouch having a first wall and a second wall, the first wall and the second wall each including a thin (<100 μm) flexible current collector comprising an electrically conductive carbon-polymer composite. The device further comprises an electrically insulating plastic spacer, one or two electrodes, an electrolyte, and a separator inside the pouch; and a heat seal to join the first wall, second wall, and the plastic spacer, so that the electrode(s), the electrolyte, and the separator are sealed inside the pouch.

Typically, the plastic spacer is between the first wall and the second wall. The electrodes are on either side of the separator, between the separator and the walls. If there is only one electrode then one side of the separator is in direct contact with a wall. The electrolyte is between the first wall and the second wall, permeating the electrode(s) and separator. The carbon-polymer composite pouch cell is corrosion resistant, providing an alternative to metal current collectors that is compatible with corrosive aqueous electrolytes.

In one or more embodiments, multiple cells are stacked on top of one another in a series configuration to get higher voltages. In such an arrangement, the positive current collector of one cell and the negative current collector of the adjacent cell can be replaced by a single bipolar current collector made of the carbon-polymer composite. The bipolar pouch cell provides a practical method for implementing (e.g., large) supercapacitor/EDLC cells based on (1) a viologen bromide system (wherein viologen is used at the anode and cathode), (2) tetraalkylammonium solid complexation of bromine in activated carbon (wherein viologen is at the anode, tetraalkylammonium is at the cathode along with bromide), or zinc bromide/tetraalkylammonium systems (wherein zinc is at the anode, tetraalkylammonium and bromide are at the cathode).

BRIEF DESCRIPTION OF THE DRAWINGS

Referring now to the drawings in which like reference numbers represent corresponding parts throughout:

FIG. 3(a) plots UV-Vis of MV and HV with chemically generated $Br_3^-$. For ease of comparison, the observed absorbance is normalized; FIG. 3(b) is a visual comparison of MV and HV complex formation with chemically generated $Br_3^-$.

Figure 8:
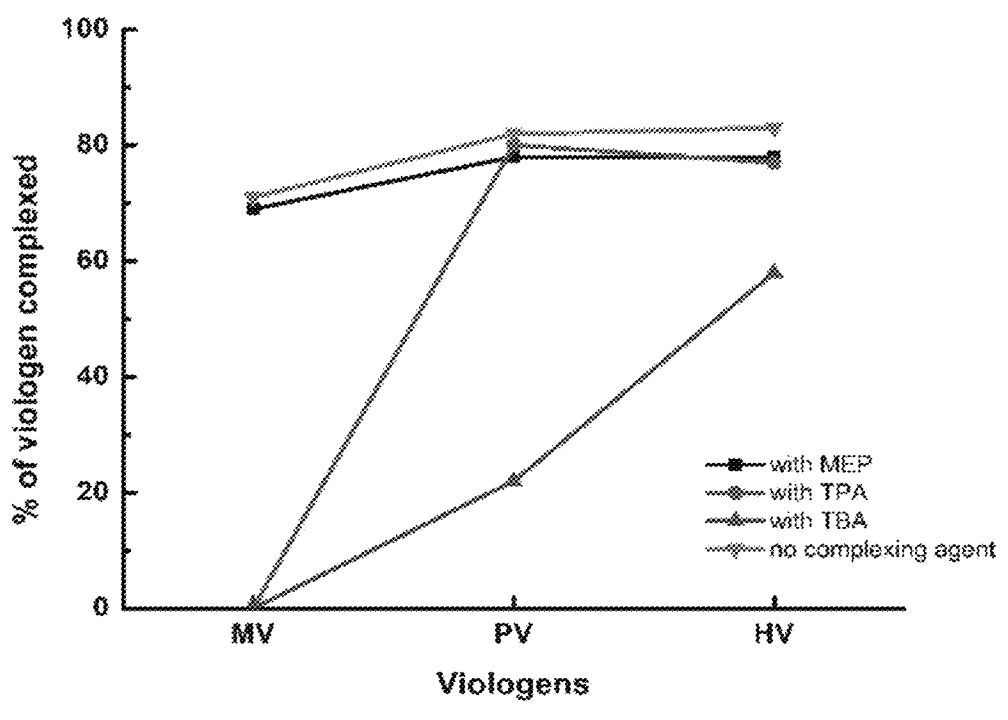

FIG. 8 shows competitive $Br_3^-$ complexing ability of quarternary ammonium salts (MEP, TPA, and TBA) with MV, PV, and HV.

FIGS. 12(a)-12(d) plot performance of two-electrode asymmetric cells constructed with aqueous electrolytes of 1.2 M KBr (blue curve), 1 M KBr/0.2 M MEPBr (black curve), and 1 M KBr/0.2 M TBABr (orange curve), respectively, the cells were charged/discharged at a rate of 2 A/g (based on the mass of positive electrode only) to 1 V, with a 4:1 negative to positive electrode mass ratio, FIG. 12(a) plots cycling stability of each cell tested at 25° C.; the inset shows two-electrode potential profiles vs capacity, FIG. 12(b) plots open circuit (OC) energy efficiency ($\eta_R$) for each cell at 25° C. Each data point was collected by charging the cell, allowing it to sit at open circuit for 2, 6, or 10 h, then discharging the cell completely. For the KBr electrolyte, self-discharge was tested for both a 1 V charge (solid blue) and a 1.2 V charge (dashed blue), FIG. 12(c) plots cycling stability of each cell tested at 40° C., and FIG. 12(d) plots $\eta_R$ at a given time for each cell at 40° C.

FIG. 13(a) plots Raman spectra of the separators after cycling, wherein Raman peaks for the non-cycled carbon electrode (green curve) are added to the plot for the comparison.

FIGS. 13(b)-13(e) are SEM images of positive electrodes, before cycling (FIG. 13(b), of an electrode from a KBr cell after cycling (FIG. 13(c)), of an electrode from a KBr/TBABr cell after cycling (FIG. 13(d)), and of an electrode from a KBr/MEPBr cell after cycling (FIG. 13(e)), FIGS. 14(a)-14(b) plot performance of 1.2 M $EVBr_2$/3 M NaBr cells, wherein FIG. 14(a) plots three-electrode GCD potential profiles for the positive electrode (orange curve), negative electrode (purple curve), and total cell (blue curve) cycled to 1.35 V at 1 A/g, during charging, the electrochemical behavior transitions from capacitive to faradaic at both electrodes, and FIG. 14(b) plots specific energy, cycling stability and Coulombic efficiency of an EV/Br two-electrode cell cycled to 1.35 V at 1 A/g.

FIGS. 16(a)-16(d) plot performance of a 1.2 M $EVBr_2$/0.12 M TBABr/2.88 M NaBr cell, wherein FIG. 16(a) plots specific energy and cycling stability of EV/Br cells with and without TBABr (the inset shows GCD profiles at the $1000^{th}$ cycle), FIG. 16(b) plots long-term cycling stability of the EV/TBA/Br cell cycled at 2 A/g to 1.3 V, and to 1.35 V (the inset shows GCD profiles for the last 3 cycles), FIG. 16(c) plots open circuit voltage for 6 h after charging the cell to 1.35 V (orange curve) and 1.3 V (blue curve), respectively, and FIG. 16(d) plots specific energy vs power of the EV/TBA/Br cell (orange curve) and its comparison to $Na_2SO_4$ (black curve) and commercial Maxwell (green curve) cells. Specific energy and power of all cells, including the commercial EDLC, were normalized to the dry mass of both positive and negative electrodes. Rate tests of the EV/TBA/Br cell were performed after the initial 1000 GCD cycles at 1 A/g.

FIGS. 30(a)-30(f) show example cross sections of different pouch cell geometries.

DETAILED DESCRIPTION OF THE INVENTION

In the following description of the preferred embodiment, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

Technical Description

The current disclosure provides an energy storage device including an EDLC having at least two electrodes in contact with a redox-enhanced electrolyte that comprises an integral active component for charge storage. For example, the redox-enhanced electrolyte can include two redox couples, such that there is a different one of the redox couples for each of the electrodes (e.g., positive and negative electrodes). By replacing an inert electrolyte with the redox-enhanced electrolyte, additional faradaic charge storage mechanisms can be added to the underlying capacitive ones, as discussed herein. The energy storage device of the present disclosure can increase capacity by utilizing previously "unused" electrolyte mass for energy storage, while maintaining the power and charge-discharge cyclability for appropriate redox-active couples. The energy storage device of the present application also includes aqueous electrolytes and less-expensive carbons, both of which can lower the costs relative to non-aqueous systems.

The EDLC of the present disclosure can provide a redox-enhanced electrolyte including two redox-couples that can significantly improve the energy density of the EDLC. In an example, when charged, a first redox-couple of the electrolyte can be adsorbed on a first electrode and a second redox-couple of the electrolyte can be adsorbed on a second electrode, therefore preventing rapid self-discharge. The EDLC of the present disclosure can retain the key advantages of EDLCs while incorporating Faradaic energy-storage without using ion-selective membrane separators. In an example, the EDLC of the present disclosure can exhibit energy densities from 10 to 65 Wh/kg (based on total electrode mass) and stable capacities for greater than 7,000 cycles. Theoretically, this could range from 5-100 Wh/kg.

Figure 2:
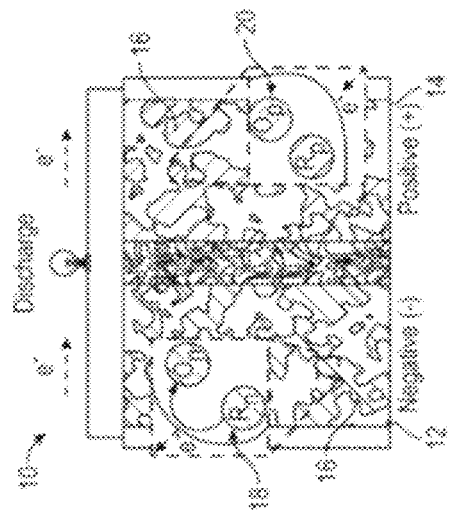
FIG. 2 illustrates an energy storage device during discharging, in accordance with at least one example.
Figure 1:
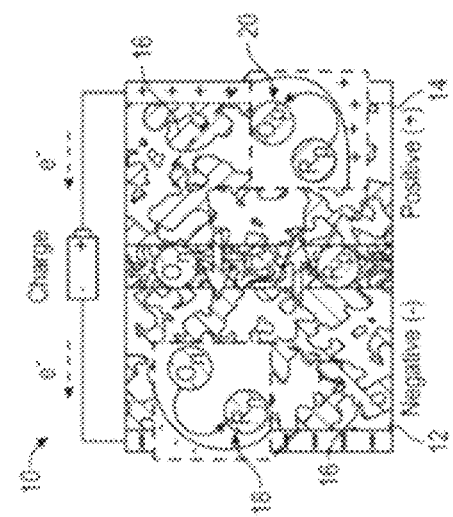
FIG. 1 illustrates an energy storage device during charging, in accordance with at least one example.

The redox-enhanced electrolyte can be a mixed solution including the two redox couples, which integrate both Faradaic and capacitive energy storage in the same device. The electrodes can become polarized when charged and retard diffusion of the oppositely-charged redox ions to mitigate self-discharge, such that the EDLC does not need an ion-selective membrane as a separator. During charging, the redox-enhanced electrolyte evolves into both a catholyte including a first redox couple and an anolyte including a second redox couple (as shown in FIGS. 1 and 2. The EDLC of the present disclosure is fundamentally different form previous devices, including pseudo-capacitors, batteries and Nafion-containing capacitors.

Prior to applying a charge to the electrodes, the redox-enhanced electrolyte includes a first redox couple and a second redox couple mixed together. However, once a charge is applied to the electrodes, a portion of the charge is transferred to the first redox couple and the second redox couple. As discussed herein, when the charge is transferred to the first and second redox couples, the solubility of the redox couples change, such that they adsorb on their respective charged electrode surface. In other words, when charged, an anolyte including a first redox couple is formed and adsorbed on the surface of a negative electrode and a catholyte including a second redox couple is formed and adsorbed on the surface of a positive electrode. As used herein, "adsorbed" can be defined as the adhesion of ions or molecules to a surface and pores of carbon electrodes, which creates an insoluble film of the adsorbate on the surface of the adsorbent. Above, the word catholyte is synonymous with "reduced form of the redox couple undergoing redox reactions at the positive electrode—a species that is oxidized during charge and reduced during discharge" and anolyte is synonymous with "oxidized form of the redox couple undergoing redox reactions at the negative electrode—a species that is reduced during charge and oxidized during discharge". Catholyte and anolyte can also refer to each redox couple, and do not necessarily refer to only one oxidation state of the couple.

FIG. 1 illustrates an energy storage device 10 during charging and FIG. 2 illustrates the energy storage device 10 during discharging, in accordance with at least one example. The energy storage device 10 can include at least two electrodes, for example, a negative electrode 12 and a positive electrode 14 (referred to herein collectively as "electrodes 12, 14").

In an example, the electrodes 12, 14 can include a porous material. For example, the electrodes 12, 14 can include one or more of, but are not limited to, activated carbons, carbide derived carbons, carbon nanotubes, mesoporous carbons, graphenes, reduced graphene oxides, metal oxides, and conducting polymers. In one example, the electrodes 12, 14 can include activated carbon. In an example, the electrodes 12, 14 can have a porosity within a range of about 300 square meter per gram ($m^2/g$) to about 3000 $m^2/g$. For example, the electrodes 12, 14 can have a porosity within a range of about 1500 $m^2/g$ to about 2500 $m^2/g$, such as 1600 $m^2/g$, 1700 $m^2/g$, 1800 $m^2/g$, 1900 $m^2/g$, 2000 $m^2/g$, 2100 $m^2/g$, 2200 $m^2/g$, 2300 $m^2/g$, and 2400 $m^2/g$. Because the redox-enhanced electrolyte contributes substantially to the charge storage capacity of the device and the surface of the carbon participates in the absorption phenomena that prevents self-discharge, carbons for redox-EDLCs can include both reasonably large surface areas but also large pore volumes and thus lower overall densities than those typically used for traditional non-redox EDLC devices.

The electrodes 12, 14 can include other components such as binders, conductive additives, and porogens. In an example, the binders can be selected from, but not limited to, polytetrafluoroethylene (PTFE), polyvinylidene difluoride (PVDF), and poly-ionic liquids. In an example, the conductive additives can be selected from, but not limited to, acetylene black, graphene, reduced graphene oxide, and carbon nanotubes.

As shown in FIGS. 1 and 2, the EDLC 10 can include a redox-enhanced electrolyte 16 including a first redox couple 18 and a second redox couple 20. As discussed herein, the redox-enhanced electrolyte 16 can be a single electrolyte that upon charging can evolve into both an anolyte and a catholyte such that a first redox couple 18 is positioned along a surface of a first electrode 12 and the second redox couple 20 is positioned along a surface of the second electrode 14. The first redox couple 18 is labeled On/Rn (e.g., anolyte) and can be used at the negative electrode 12. The first redox couple 18 can be reduced upon charging, and oxidized upon discharge. The second redox couple 20 is labeled Op/Rp (e.g., catholyte) and can be used at the positive electrode 16. The second redox couple 20 can be oxidized upon charging and reduced upon discharge.

As discussed herein, the redox-enhanced electrolyte 16 can be aqueous, organic, or an ionic liquid and include the first redox couple 18 and the second redox couple 20. The first redox couple 18 for the negative electrode 12 can have standard potentials at or slightly more-cathodic than the hydrogen evolution potential, as well as high solubility and solution compatibility with the catholyte. To minimize or prevent rapid self-discharge, the first redox couple 18 can have a positive charge and physically adsorb on the negative electrode 12 (e.g., activated carbon) following charging.

The second redox couple 20 for the positive electrode 14 can have a reduction potential near, or slightly more positive/anodic than, the oxygen evolution potential to maximize energy density, as well as high solubility and solution compatibility with the anolyte. To minimize or prevent rapid self-discharge, the second redox couple 20 can have a negative charge and physically adsorb on the positive electrode 14 (e.g., activated carbon) following charging.

In an example, the first redox couple 18 can include a viologen and the second redox couple 20 can include a halide (e.g., bromide). In an example, the first and second redox couples 18, 20 do not comprise a metal. The metal-free redox couples are advantageous because they can be less expensive, easier to recycle, do not form dendrites, and are less environmentally harmful. The first redox couple 18 and the second redox couple 20 can be chosen such that the first and second redox couples 18, 20 operate at a different potential.

Viologens are derivatives of 4,4'-bipyridyl. An example of the dicationic 4,4'-bipyridinium portion of a viologen is shown below.

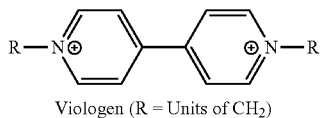

Viologen (R = Units of CH$_2$)

Examples of this viologen are methyl viologen (R=methyl), ethyl viologen (R=ethyl), benzyl viologen (R=benzyl), and pentyl viologen. These viologens have been isolated as salts of the chloride (Cl$^-$), bromide (Br$^-$), acetate (CH$_3$CO$_2^-$) tetrafluorborate (BF$_4^-$), perchlorate (ClO$_4^-$), triflurormethanesulfonate (CF$_3$SO$_3^-$), tetraphenylborate (BPh$_4^-$), and hexaflurophosphate (PF$_6^-$), to name a few. Each of redox couples for methyl, ethyl, heptyl, and benzyl are stable in neutral conditions. The SCE is the standard calomel electrode.

In an example, the first redox couple 18 can include one of methyl viologen and heptyl viologen. The standard potentials for methyl and heptyl viologens are at or slightly more-cathodic than the hydrogen evolution potential. In an example, a concentration of the first redox couple 18 can be within a range from about 0.1 molar (M) to about 5 M, such as 0.1 M.

In one example, the second redox couple 20 can include bromide (Br$^-$), which is generally inexpensive and highly soluble (greater than 1 M). Further, aqueous reduction potential of bromide is located above the thermodynamic oxygen evolution potential. In an example, a concentration of the second redox couple 20 can be within a range of about 0.1 M to about 5M, such as about 0.4 M to about 1 M.

The EDLC of the present disclosure can retain the key advantages of EDLCs while incorporating Faradaic energy-storage without using ion-selective membrane separators. In an example, the EDLCs of the present disclosure can deliver power densities >3 kW/kg, based on mass of electrodes and electrolyte, which sets them apart from many energy storage technologies. Conventional EDLCs can have a voltage that varies linearly with the state of charge, so the galvanostatic charge-discharge curves are triangular, which can be undesirable for many applications. The ELDCs of the present disclosure exhibit EDLC behavior initially, then transition to battery like behavior at higher voltages, delivering a desirable steady voltage. Together, these properties can provide the high power density of supercapacitors along with the constant potential and high energy density of batteries.

1. First Example: Mechanism of Reversible Solid Complex Formation on Both Cathode and Anode Like the viologens, bromide has proven an efficient catholyte in electrochemical energy storage systems, particularly in aqueous flow batteries. However, since the evolution of bromine gas is toxic and corrosive, quaternary ammonium salts are frequently used in bromine flow batteries to complex bromine/Br$_3^-$, reducing the activity and vapor pressure.

Because of the structural similarity between these complexing agents and viologens, the present disclosure describes (1) a viologen anolyte that may also participate in the complex formation with Br$_3^-$ at the cathode, and (2) each viologen having different length of alkyl substituents will complex with Br$_3^-$ at varying degree of interaction and adsorption to the electrode. The inventors suspect MV will complex Br$_3^-$ less efficiently due to its shorter, less hydrophobic, substituent R (=methyl) in aqueous environments. The degree of complexation between HV and MV with chemically generated Br$_3^-$ was investigated through UV-Vis. (FIG. 3(a)). As expected, UV-Vis results reveal that ca. 15% more of HV complexed/precipitated with Br$_3^-$ than MV.

The inventors postulate that strong adsorption of HV$^{2+}$·.2Br$_3^-$ to the cathode as a solid complex enables suppression of the reactivity and diffusion of bromine/Br$_3^-$ as well as improves electrochemical reversibility of the bromide redox couple. This may explain why the HV/Br cell is stable while the MV cell is not.

Figure 4:
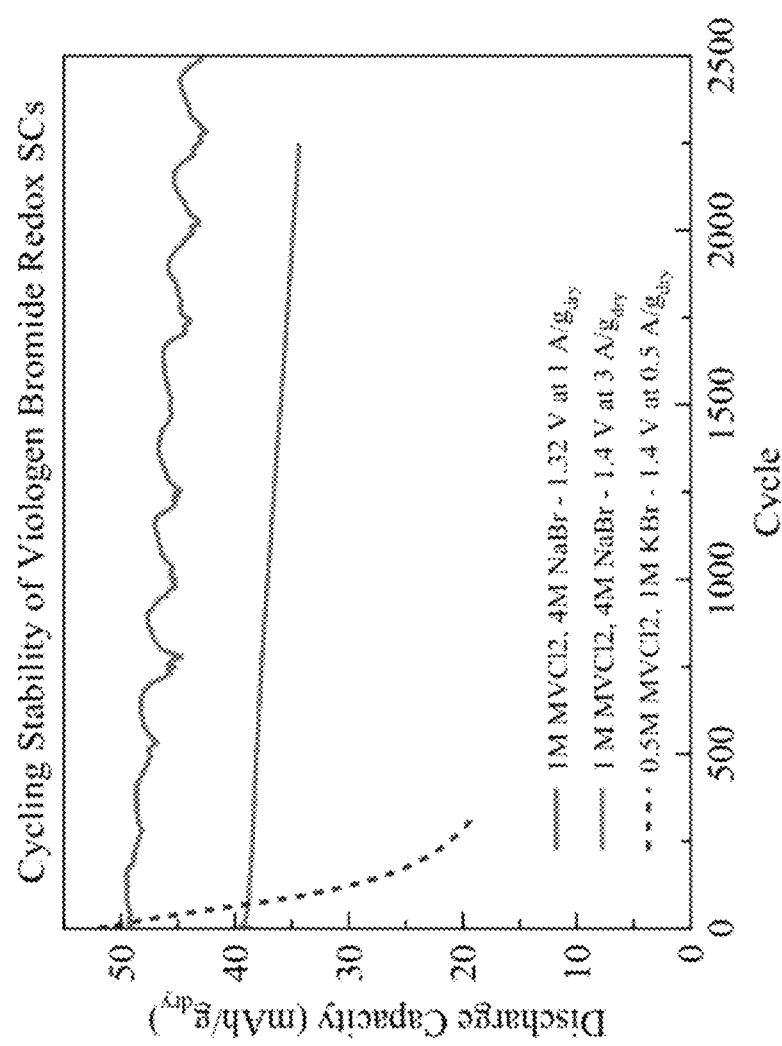
FIG. 4 plots galvanostatic charge/discharge cycling with $MVCl_2$ and NaBr.
Figures 5A, 5B:
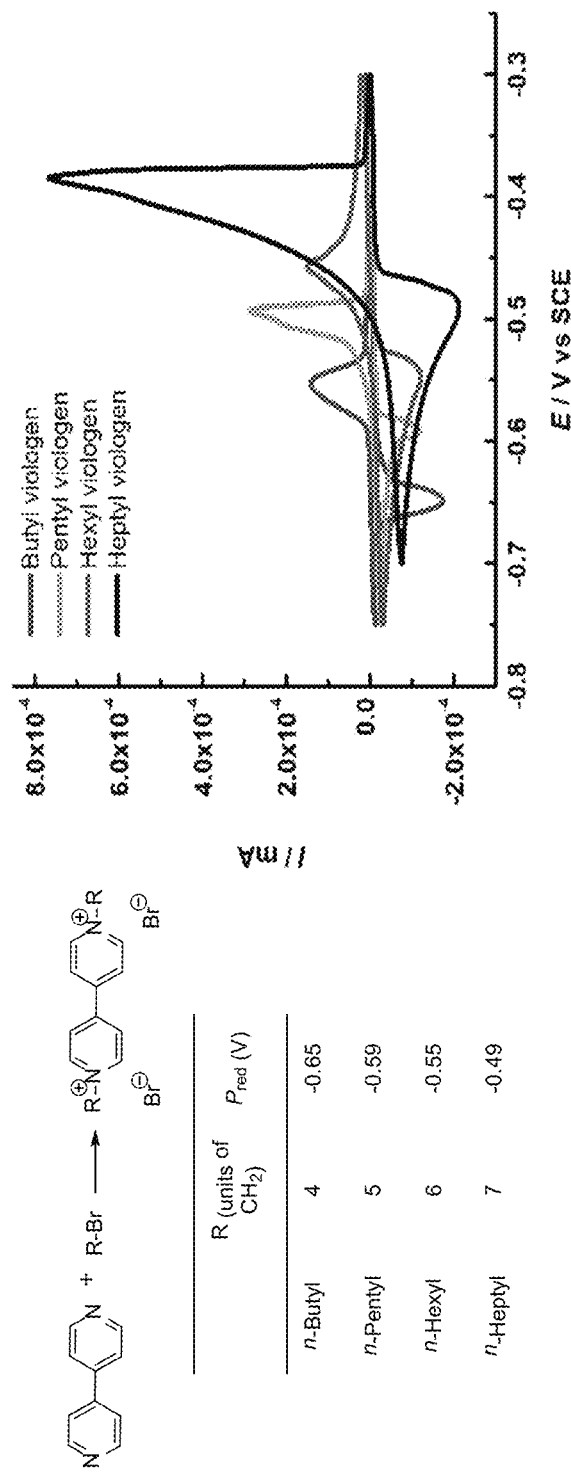
FIG. 5(a) illustrates synthesis of viologens and FIG. 5(b) plots cyclic voltammetry of each viologen.

As described herein, the previously unstable MV/Br system was tested in order to confirm the above described rationale (but with modifications that reflect the rationale). A MV/Br cell with excess bromide (4 times the MV concentration) was constructed and the concentration of MV was increased. In addition, the state of charge was reduced by operating the cell to 1.32 V instead of 1.4 V (as done previously). These operating conditions greatly facilitate the formation, complexation, and adsorption of Br$_3^-$ to the cathode. Original capacity fade with the MV/Br system was characterized by a 60% loss over 300 cycles. However, much improved stability (10% capacity loss over 2000 cycles) was observed when the cell was operated to 1.32 V with excess concentration of MV and Br$^-$ (see FIG. 4). The results presented herein with the newest MV/Br cell supports the rationale described herein for the operating mechanism of viologen bromide system.

As noted previously, the degree of adsorption of charged redox product through complexation should also contribute to the difference in self-discharge between MV and HV systems. Previously, the retarded self-discharge for the halides could not be explained purely by electrostatics, and was attributed to physical adsorption of Br$_3^-$ within the activated carbon surface, preventing cross diffusion. The present disclosure now suggests that it is actually the HV$^{2+}$ dication that holds Br$_3^-$ better at the cathode through film formation. Together with the film-forming property of HV$^+$. with Br$^-$ at anode, the charged products HV$^+$. and Br$_3^-$ are all efficiently retained at the surface, inside the pores of the electrodes, and thus provide exceptionally low self-discharge and high coulombic efficiency.

Thus, the study presented herein suggests that the successful operating mechanism of the HV/Br system is actually attributable to two electroprecipitation processes occurring simultaneously at both electrodes. Through electroprecipitation, each ion acts as a charge-storing redox couple at one electrode and as a complexing agent at the other electrode (Scheme 1).

Scheme 1. Operating mechanism of HV/Br system through reversible insoluble complex formation at both electrodes.

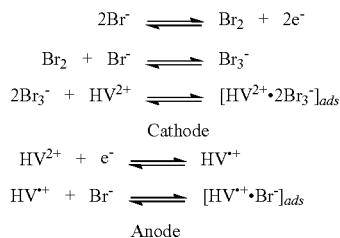

2. Second Example: Pentyl Viologen as an Anolyte

For redox ECs, higher redox active electrolyte concentrations are needed to maximize faradaic energy storage. The free volume in the porous carbon electrodes and the separator determines the volume of electrolyte available. This volume, along with the concentration of the redox-active electrolytes, determines the maximum possible number of ions available for faradaic charging. Consequently, better device performance requires a more concentrated electrolyte to minimize electrolyte mass but still maintain a large reservoir of each redox couple.

In order to efficiently replace sparingly soluble HV for the redox EC, the substitute viologen must (1) be easy to synthesize, (2) have high solubility (>1 M) in the oxidized dication state (for energy density), (3) precipitate as a solid film when reduced to the cation radical at anode (for better Coulombic efficiency and self-discharge), and (4) form an insoluble complex with $Br_3^-$ at cathode (for stability, Coulombic efficiency and self-discharge). These criteria are challenging because long hydrophobic alkyl chains necessary for (3) and (4) work against (2) in an aqueous system.

As shorter alkyl groups do not form films upon charging, a series of alkyl substituted viologens with chain lengths R>4 were synthesized. Hexyl viologen (R=6) was excluded from further studies because it does not exhibit good solubility (<0.5 M) in the presence of NaBr. Surprisingly, however, butyl viologen (BV, R=4) and pentyl viologen (PV, R=5) exhibit remarkable solubility (>1.5 M), and form insoluble films when reduced to the radical cation. Thus, BV and PV were further investigated for $Br_3^-$ complexing ability through UV-Vis experiments.

Figure 6:
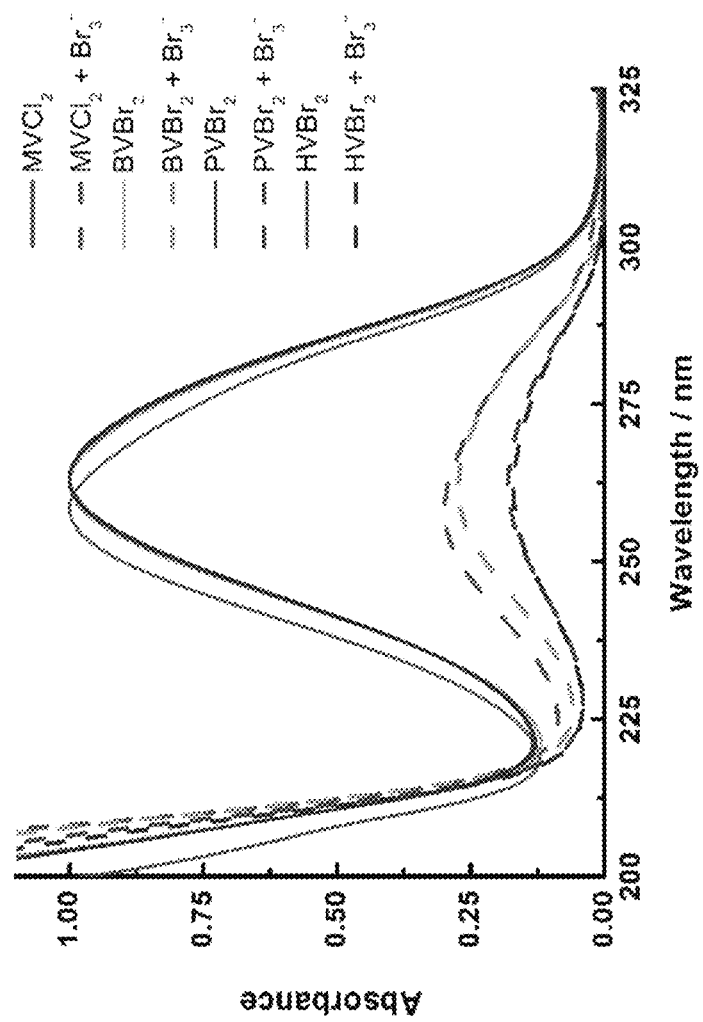
FIG. 6 plots UV-Vis with viologens and chemically generated $Br_3^-$ (20 mM of viologen and 40 mM of $Br_3^-$).
Figure 7C:
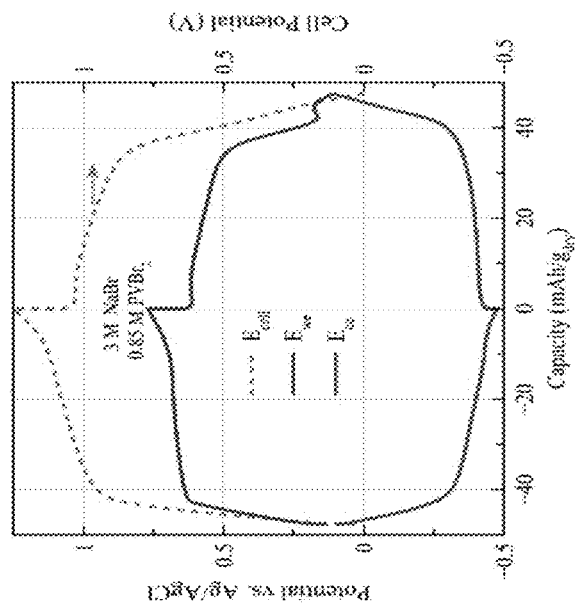
FIGS. 7(a)-7(c) plot the galvanostatic charge/discharge profiles (dashed green lines) of the PV/Br redox couples for cell testing up to 1.15 V (FIG. 7(a)), 1.2 V (FIG. 7(b)), and 1.25 V (FIG. 7(c)); the positive electrode (solid blue) and the negative electrode (solid red), respectively, are referenced to the centrally placed SCE.
Figure 7B:
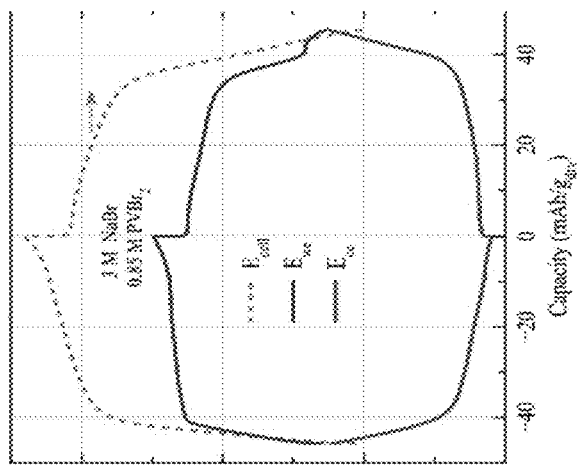
Figure 7A:
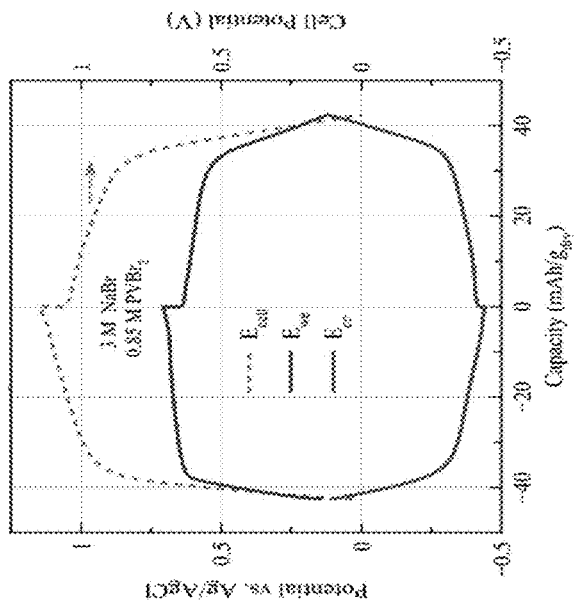

As illustrated in FIG. 6, PV complexes with $Br_3^-$ as efficiently as HV. PV was selected for the anolyte as it (1) exhibits remarkable solubility (>1.5 M), (2) forms an insoluble film when reduced to the radical cation, and (3) has competitive $Br_3^-$ complexing ability as compared to HV. In addition, the standard reduction potential of PV is 0.1 V more cathodic than that of HV, so it is expected to span a wider voltage range than the previous 1.2 V set for HV/Br system.

A cell with 0.85 M PV/3 M NaBr electrolyte was tested by galvanostatic charge/discharge cycling. The cell runs stably at 1.15V for over 1000 cycles, but with a limitation: when operating potential increases to 1.2V, the iR drop increased and the cell started fading. In addition, an unexpected hump around 0.25V during discharge was observed at cathode. This behavior became more distinctive when the cell was operated at 1.25V or higher potentials.

These interesting shape changes when SOC increases to 1.2 V and 1.25 V may be caused by the following scenarios. Firstly, a solid complex presents in high quantity and gradually blocks the pores in the carbon, thus increasing the cell resistance. Secondly, increased demand for $PV^{2+}$ at the negative electrode causes diffusion of $PV^{2+}$, leading to an insufficient amount of complexing agent for $Br_3^-$ at the positive electrode. As the concentration of $PV_2^+$ is decreased the equilibrium will shift, and the relative concentration of the ion pair complex will decrease accordingly.

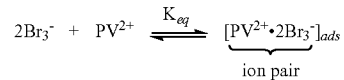

As literature reports that strong adsorption improves reversibility of bromine reduction, slowed kinetics can be expected when complex formation is suppressed. Overpotential with bromide redox reaction and larger iR drop are expected. When the operating potential increases, most of the potential increases are indeed reflected at the positive electrode with larger iR drop, although there is an excess of bromide redox active electrolytes that otherwise could have maintained plateau more at positive. This supports the rationale presented herein.

Interestingly, performance degradation is mostly not permanent. When the cell potential was held at 0V for 2 h and resumed charge/discharge cycling, 99% of the original capacity was re-generated.

3. Third Example: Additional Complexing Agent a. Overview

Based on results from the PV cell, the inventors realized that the viologen/bromide system is not yet fully utilized. Approximately 20% of redox active viologen is being consumed at the cathode for complexation. Consequently, less PV is available for faradaic reactions and capacity is not maximized. In order to supplement any shortage of complexing agent when the state of charge is increased, embodiments of the present invention utilize an additional $Br_3^-$ complexing agent. There are well known $Br_2/Br_3^-$ complexing agents, e.g., methyl ethyl morpholinium bromide (MEM) and methyl ethyl pyrrolidinium bromide (MEP), being used for redox flow batteries. However, as opposed to redox flow battery applications where strong adsorption might be detrimental to movement of redox active electrolyte in the system, specific adsorption of redox couples on the electrode surface is critical for redox-EC operation. Considering how strongly $Br_3^-$ adsorbs to the electrode surface affects the overall performance of the viologen bromide cell, embodiments of the present invention applied the following selection criteria for an alternative complexing agent in the redox EC described herein. Specifically, the complexing agent (1) should not participate redox reaction at anode, (2) should have stronger complexing power for $Br_3^-$ than PV, preferably the complex formed should exist in solid form, and (3) its complex should be significantly smaller than $PV^{2+} \cdot 2\ Br_3^-$.

Inspired by the discovery reported in the reversible electrochromism applications using aqueous systems of tetrabutylammonium bromide, embodiments of the present invention incorporated tetraalkylammonium salt as a complexing agent in a supercapacitor. In contrast to the complexing agent used for redox $Br^-$ flow battery, it was discovered that certain tetraalkylammonium bromide possessing carbon numbers more than 10 facilitated complex formation in a solid form. In addition, amphiphilic quaternary ammonium salt complex was shown to adsorb well to hydrophobic carbon electrodes and decrease charge transfer resistance for bromide oxidation in aqueous electrolytes. Thus certain tetraalkylammonium salts were considered an ideal candidate for supercapacitor applications as described herein.

Readily available and water soluble tetraalkylammonium bromide salts ($R_4N^+Br^-$, where R=propyl, butyl, and pentyl, respectively) were selected. These quaternary ammonium salts were tested first for competitive adsorption vs PV on the activated carbon (AC) as to avoid using additional complexing agent that comes at the expense of sacrificing surface for PV during electrode preparation process. Based on an adsorption test on AC between PV and a series of tetraalkylammonium salts, UV data reveals that tetrapentylammonium salt adsorbs to the surface of AC more strongly than redox active PV. Thus, tetrapentylammonium was excluded for further testing.

The complexing ability of tetrabutylammonium bromide (TBABr) and tetrapropylammonium bromide (TPABr) with $Br_3^-$, in comparison to PV, was tested. Surprisingly and unexpectedly, tetrabutylammonium bromide (TBABr) was found to have higher complexing ability with $Br_3^-$ than the TPABr and viologens (that were also tested). Presence of TBABr dropped to almost ca. 60% of the PV complexed with $Br_3^-$. This screening process led to the identification of TBABr as a promising additional complexing agent for redox EC. In contrast, MEP doesn't have strong complexing ability over any viologens.

b. Further Studies of the Properties of $Br_3^-$ Complexing Agents

In order to further support the efficient use of the $Br^-/Br_3^-$ redox couple for aqueous redox ECs, two differently-structured quaternary ammonium salts were selected and compared as complexing agents for $Br_3^-$ (complexing agent refers to $Br_3^-$ complexing agent throughout). Asymmetric cyclic methyl ethyl pyrrolidinium bromide (MEPBr), a commonly used complexing agent for aqueous bromine flow batteries, forms a separate oily-phase with $Br_3^-$ while the symmetric and more hydrophobic tetrabutylammonium bromide (n-$Bu_4$NBr; TBABr) is known to form a solid complex.[34,37] Presented herein are studies of how each complexing agent affects the overall performance of the redox ECs, relative to a control system without either additive.

Figures 9A, 9B, 9C:
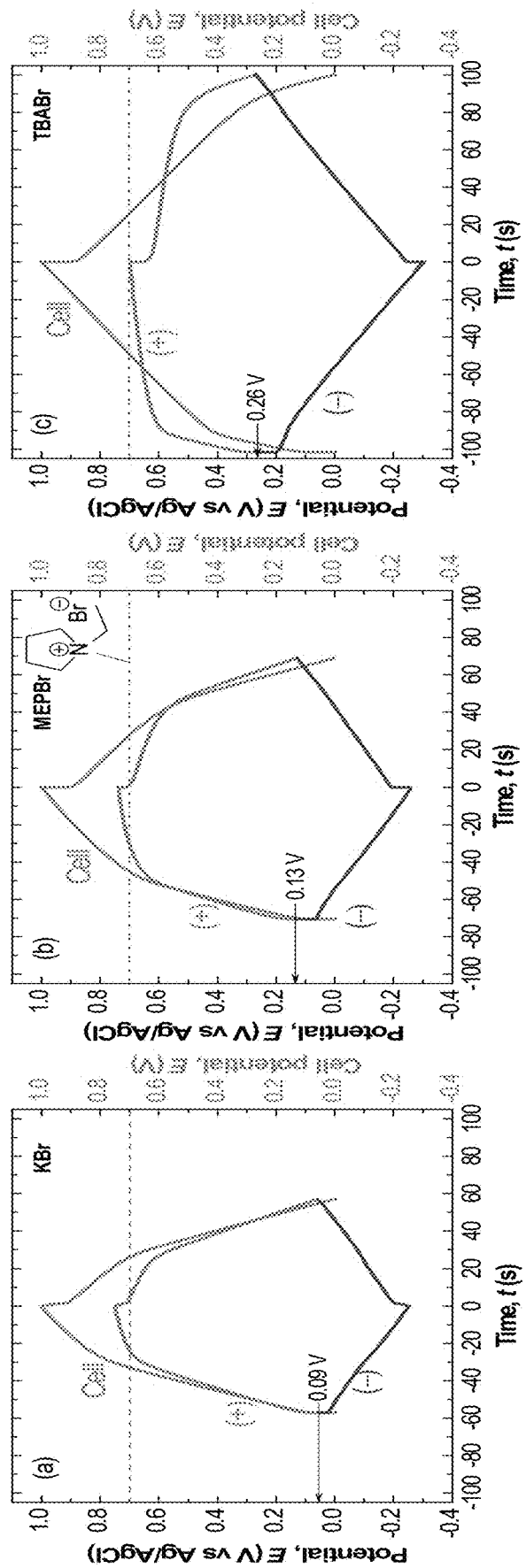
FIGS. 9(a)-9(c) plot the galvanostatic charge/discharge potential profiles of the asymmetric cells (blue curves) divided into contributions from the positive electrode (orange curves) and the negative electrode (purple curves), referenced to the centrally placed Ag/AgCl reference electrode. The cells were charged/discharged at a rate of 2 A/g (based on the mass of positive electrode only) to 1 V, with a 4:1 negative to positive electrode mass ratio; the aqueous electrolytes were 1.2 M KBr (FIG. 9(a), 1 M KBr+0.2 M MEPBr (FIG. 9(b)), and 1 M KBr+0.2 M TBABr (FIG. 9(c)).

Three asymmetric EC cells were constructed, all utilizing the $Br^-/Br_3^-$ redox couple at the positive electrode, with (1) no complexing agent (1.2 M KBr electrolyte), (2) methyl ethyl pyrrolidinium bromide (MEPBr; 1 M KBr+0.2 M MEPBr), and (3) tetrabutylammonium bromide (TBABr; 1 M KBr+0.2 M TBABr), respectively. The negative counter electrode was purely capacitive and oversized to increase capacity so that the positive electrode could reach the Br oxidation potential with a total applied cell voltage of 1 V. The influence of each complexing agent on the electrochemical behavior of the bromide catholyte in redox ECs was determined by galvanostatic charge/discharge (GCD) cycling tests of each asymmetric cell in a three-electrode configuration (FIGS. 9(a)-9(c)).

Figure 17:
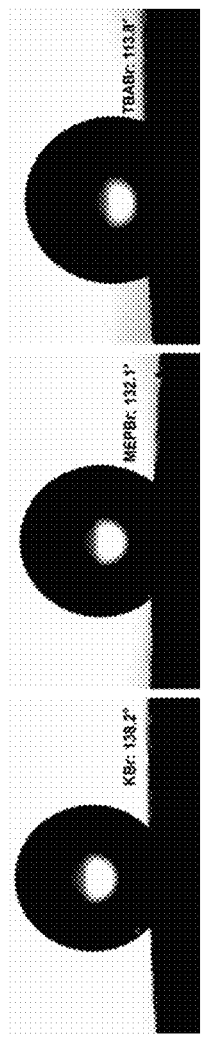
FIG. 17 illustrates a contact angle of test electrolyte on the surface of a porous activated carbon pellet, showing (left) aqueous KBr solution droplet, (middle) aqueous MEPBr solution droplet, and (right) aqueous TBABr solution droplet.

All cells show electrochemical behavior that transitions from capacitive to faradaic energy storage at the positive electrode (orange curve), indicating oxidation of $Br^-$ to $Br_3^-$, and only a capacitive (linear potential vs time/charge) response at the negative electrode (purple curve) during charging. Notably, there are differences when TBABr is present as a complexing agent as compared to the KBr and KBr/MEPBr cells. For example, a greater potential of zero charge (PZC) was observed for the KBr/TBABr cell (0.26 V) compared to the KBr (0.09 V) and KBr/MEPBr (0.13 V) cells. The more positive PZC with KBr/TBABr electrolyte allows bromide oxidation to occur earlier in the charging stage and increases the $\Delta V$ for the capacitive negative electrode, which translates to greater faradaic charge storage at the positive electrode before the arbitrary cell cutoff potential of 1 V is reached (FIGS. 9(a)-9(c); orange curves). Considering the amphiphilic nature of the tetrabutylammonium cation ($TBA^+$),[38,39] the inventors reason that TBABr acts as a surfactant and $TBA^+$ adsorbs at the porous carbon electrodes. To verify this hypothesis, contact-angle measurements were conducted. The contact angle for the carbon electrode with a droplet of aqueous TBABr solution is ~24° smaller compared to a droplet of aqueous KBr solution (138°; FIG. 17). This surfactant behavior may increase wettability of hydrophobic electrodes, and thus facilitate infiltration of hydrophilic bromide catholyte.[39]

Figures 18A, 18B:
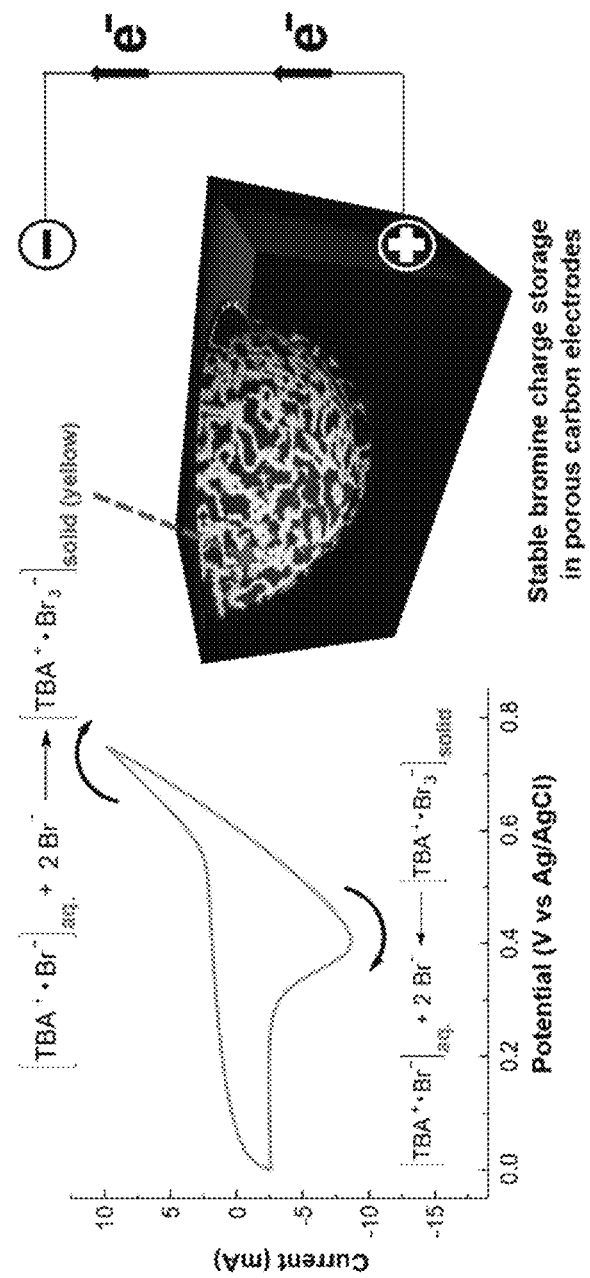
FIG. 18(a) is a cyclic voltammogram of 1 M KBr/0.2 M TBABr for a scan rate of 10 mV/s, wherein an activated carbon pellet pasted on the carbon cloth served as working electrode and a Pt wire as counter electrode (as reference, an Ag/AgCl electrode was used).
FIG. 18(b) shows schematic illustration of stable bromine charge storage in porous carbon electrodes.

The present disclosure notes that the onset point of the faradaic plateau at the positive electrode is a function of the complexing agent used. The horizontal grey dashed line drawn at 0.7 V in FIGS. 9(a)-9(c) makes apparent the largest negative shift in the $Br^-/Br_3^-$ redox potential for the KBr/TBABr cell. Additional cyclic voltammetry shows a redox potential that is consistent with above GCD potential profile result, as well as a reversible redox reaction in the presence of TBABr (FIG. 18(a)).

Figure 10A:
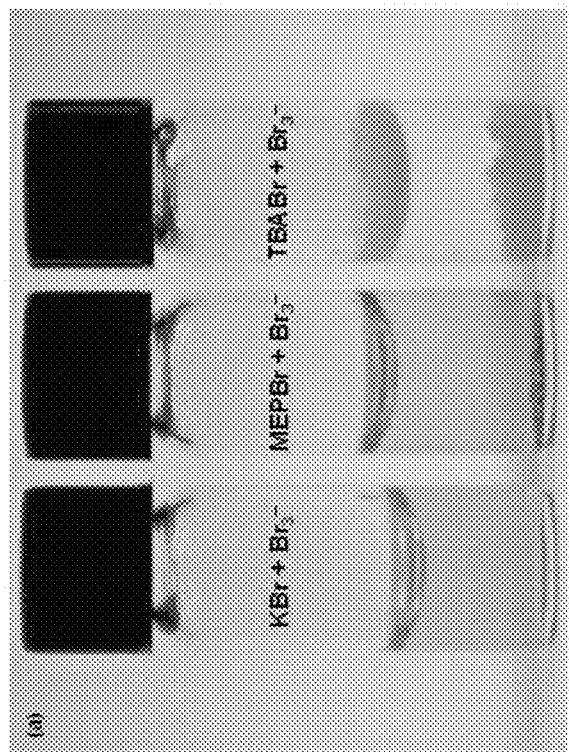
FIG. 10(a) shows complexation of chemically generated $Br_3^-$ by the addition of potassium bromide (left), MEPBr (middle), and TBABr (right).
Figure 10C:
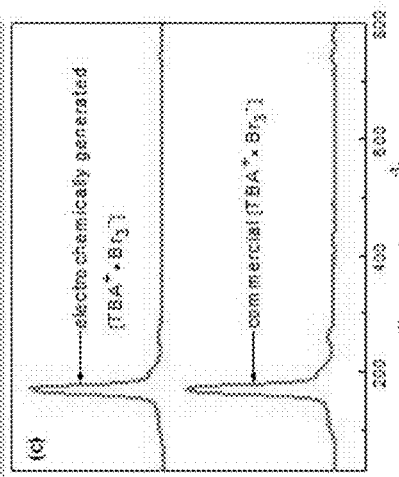
FIG. 10(c) shows Raman spectra of the electrochemically generated [$TBA^+$.$Br_3^-$] solid complex (blue curve) and commercial [$TBA^+$.$Br_3^-$] solid complex (orange curve).
Figure 10B:
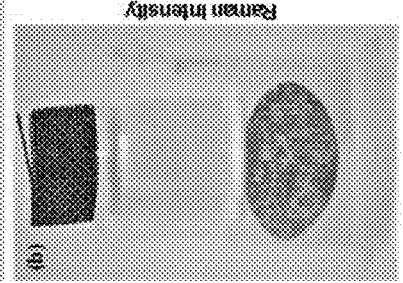
FIG. 10(b) shows an electrochemically generated [$TBA^+$.$Br_3^-$] solid complex by controlled potential electrolysis.

The observed electrochemical behavior can be explained by the reversible formation of [$TBA^+ \cdot Br_3^-$] solid complex that decreases the $Br_3^-$ concentration at the interface between the electrolyte and the high-surface-area electrode. Both chemical (FIG. 10(a)) and electrochemical (FIG. 10(b)) methods confirm the generation of a [$TBA^+ \cdot Br_3^-$] solid complex. The image (FIG. 10(a); right vial) visually shows that after complexation induced by $TBA^+$, $Br_3^-$ is almost entirely removed from the solution. Notably, the solutions with MEPBr (middle vial) and KBr (left vial) retain a yellow tint, demonstrating that a significant concentration of $Br_3^-$ remains dissolved due to insufficient complexation by $MEP^+$ (and $K^+$, respectively). FIG. 10(b) shows electrochemical generation of a solid complex on the surface of a carbon cloth by passing anodic current in a KBr/TBABr electrolyte. The Raman spectrum taken of this solid exhibits an intense band at 169 $cm^{-1}$, which corresponds to symmetric stretching vibration of $Br_3^-$,[40,41] and its spectrum is identical to the Raman spectrum of commercial [$TBA^+ \cdot Br_3^-$] solid complex (FIG. 10(c)). Further characterization of the electrochemically generated [$TBA^+ \cdot Br_3^-$] solid complex in an aqueous system is well-documented elsewhere.[37]

Strong adsorption of the charged products within the electrodes has been found to be an effective mechanism to prevent cross-diffusion in a full cell.[26] The present disclosure hypothesizes that the complexation strategy described herein may suppress cross-diffusion even more effectively if the [$TBA^+ \cdot Br_3^-$] solid complex is retained in the pores of the high-surface-area carbon electrodes, instead of being formed and precipitating to the bulk solution upon charging. In order to investigate this hypothesis, controlled potential electrolysis with 1 M KBr/0.2 M TBABr solution was performed with an activated porous carbon pellet as the working electrode (denoted as electrolyzed C pellet) to provide a relevant, yet extreme charged state. As a control, an identical activated carbon pellet (denoted as the control C pellet) was separately prepared and infiltrated with same electrolyte solution through repeated vacuum/$N_2$ steps.

Figure 11A:
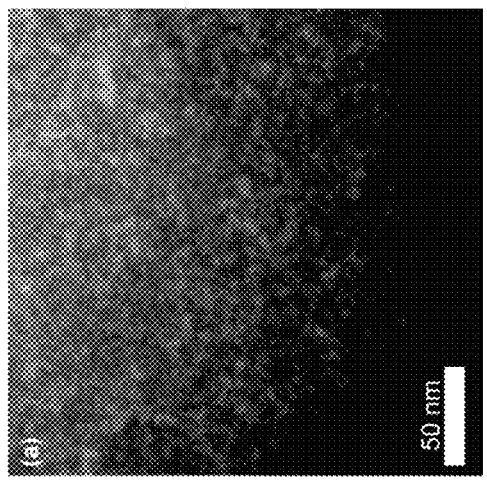
FIGS. 11(a)-11(b) show scanning transmission electron microscopy (STEM) images of electrolyzed C pellet (FIG. 10(a)) and the control C pellet (FIG. 10(b)), collected by a high-angle annular dark-field (HAADF) detector. Sample preparation steps including controlled potential electrolysis are detailed in the experimental section.
Figure 11B:
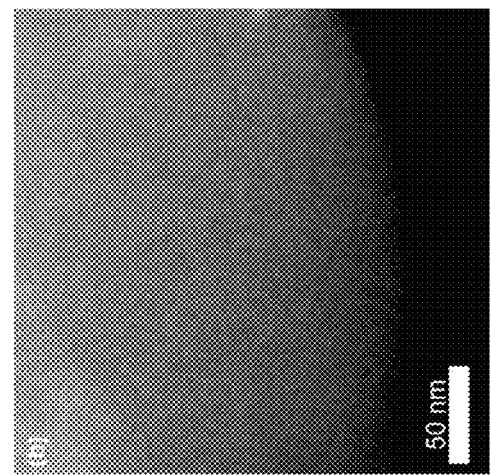
Figure 19:
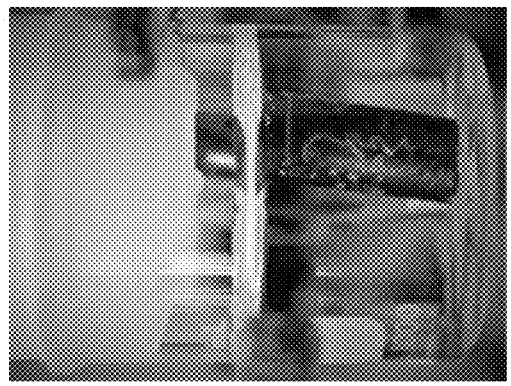
FIG. 19 shows electrochemical generation of a [$TBA^+$.$Br_3^-$] solid complex. Controlled potential electrolysis with 1 M KBr/0.2 M TBABr solution was performed with a non-porous graphite rod as working electrode, a Pt wire as the counter electrode, and an Ag/AgCl reference electrode.

Both carbon surfaces were analyzed by scanning TEM (STEM) with the signal being acquired using a high-angle annular dark-field detector (HAADF-STEM). In this imaging mode, the signal contrast scales linearly with sample thickness, and as the square of average atomic number (Z) of atoms in the sample.[42,43] Therefore, for the sample analysis presented here, the higher average atomic number of the bromine-containing [$TBA^+.Br_3^-$] solid complexes compared to that for porous carbon ensures that such complexes confined in the pores appear as bright regions in the image (Z-contrast imaging). FIG. 11(a) shows a scanning TEM (STEM) image of the electrolyzed C pellet. The material displays clear contrast with nm-scale bright clusters that correspond to concentrations of the element Br, which EDX analysis confirms (Table S2). In contrast, the control C pellet shows no high-contrast spots (FIG. 11(b)), and no Br signal was detected by EDX (Table S2). This control image suggests that Br from KBr/TBABr solution is removed during washing steps, and that the bright regions in FIG. 11(a) are mainly due to signals detected from collecting electrons scattered by the insoluble bromide-containing [$TBA^+.Br_3^-$] complex. These data thus show that the [$TBA^+.Br_3^-$] solid complex generated in-situ during electrolysis is contained in the pores. This complexation approach combined with porous carbon electrodes being used for EDLCs may lead to enhanced stability and slower self-discharge of the bromide-based redox ECs, without using ion-exchange membranes. The present disclosure notes that if a non-porous electrode is used, precipitation of the [$TBA^+.Br_3^-$] solid complex occurs, which would cause irreversible capacity loss (FIG. 19).

In order to test stability and self-discharge rates, asymmetric cells were constructed in the two-electrode cell configuration with a paper separator. In cycling stability tests, the KBr cell lost ~20% of its specific energy over 500 cycles. In contrast, the KBr/TBABr and KBr/MEPBr cells show no fading over the course of 500 cycles, and produce ~80% and ~40% higher energy density compared to the KBr cell, respectively (FIG. 12(a)). Large differences between the cells are further evident from self-discharge tests. The self-discharge rate determined by the open circuit energy efficiency, $\eta_R$, of the KBr/TBABr cell was substantially lower than that for KBr and KBr/MEPBr cells, retaining 50% of its energy after 10 h at open circuit, $\eta_R(10\ h)=50\%$, compared to $\eta_R(10\ h)$ of only 1% and 14% for the KBr and KBr/MEPBr cells, respectively (FIG. 12(b)). Importantly, when the KBr cell was charged to 1.2 V to attain a higher capacity, which is closer to that of the KBr/TBABr cell, an even faster self-discharge rate was observed (FIG. 12(b), solid blue vs dashed blue). This result implies that the self-discharge problem with uncomplexed $Br^-/Br_3^-$ redox couple is worsened at higher states of charge, limiting its application in high-performance redox EC devices. The problems with cycling stability and self-discharge are much aggravated at 40° C. for the KBr and KBr/MEPBr cells relative to the KBr/TBABr cell, suggesting that the increased diffusivity of soluble $Br_3^-$ at high temperatures accelerates the redox shuttle self-discharge mechanism (FIGS. 12(c) and 12(d); results for self-discharge tests from 0° C. to 40° C. are summarized in Table S3).

These studies demonstrate that charge retention of bromide catholyte, and the stability and self-discharge performances, depend on whether $Br_3^-$ is uncomplexed, complexed with $MEP^+$ (liquid state), or complexed with $TBA^+$ (solid state). Our results suggest that [$TBA^+.Br_3^-$] solid complex generated within the electrode pores suppresses cross-diffusion of oxidized bromide and lowers the self-discharge rate. Meanwhile MEPBr, a common complexing agent for bromine flow batteries, barely shows improvement over a cell without a complexing agent. The molecular structure of $MEP^+$, which lacks hydrophobic substituents, appears to provide insufficient complexation/precipitation with $Br_3^-$,[37] leaving high concentrations of free $Br_3^-$ in the electrolyte solution (picture in FIG. 10(a)).

Figure 20:
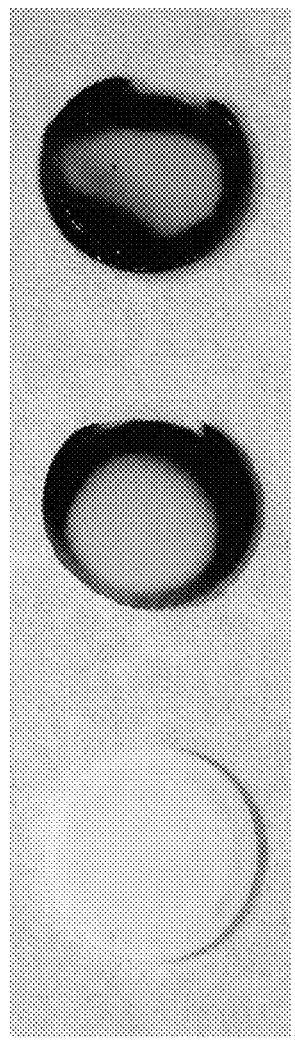
FIG. 20 shows separators (Whatman™ #1 filter paper) after GCD cycling, showing (left) a separator from an asymmetric KBr/TBABr cell; (middle) separator from an asymmetric KBr/MEPBr cell; and (right) separator from asymmetric KBr cell.
Figure 21B:
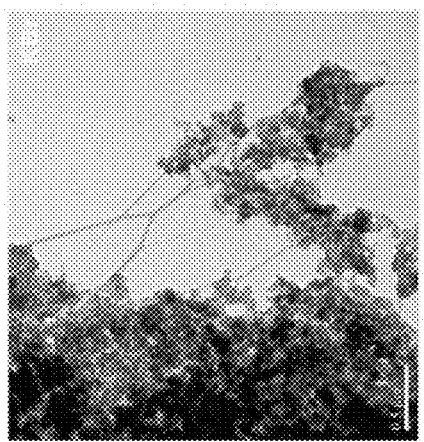
FIG. 21(a) is a transmission electron microscope (TEM) image showing the positive electrode before cycling (for comparison) and FIGS. 21(b)-21(d) are TEM images of the positive electrodes after GCD cycling, for an electrode from a KBr cell (FIG. 12(b)), an electrode from a KBr/TBABr cell (FIG. 21(c)), and an electrode from KBr/MEPBr cell (FIG. 21(d)).
Figure 21D:
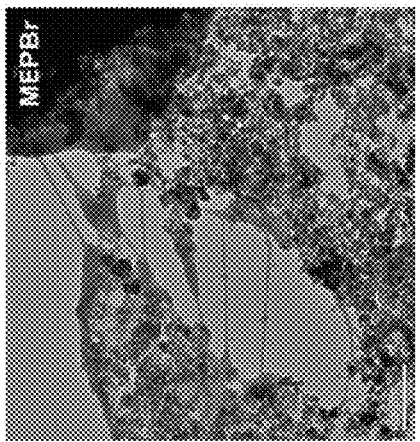
Figure 21A:
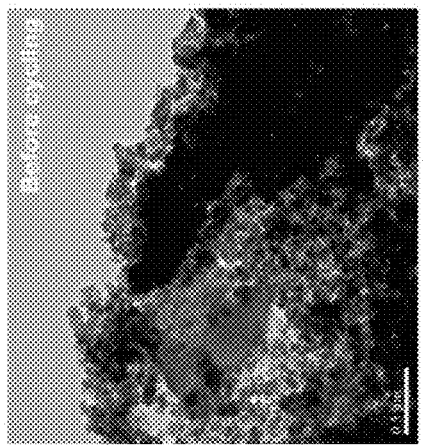
Figure 21C:
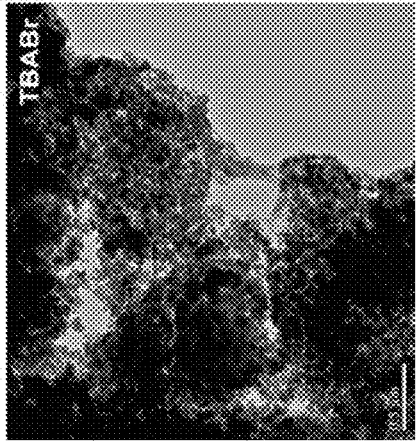

The question as to whether the decrease in specific energy observed for KBr and KBr/MEPBr cells is temporary due to reversible shuttling/diffusion effects or irreversible fading from chemical reactions was addressed by disassembling tested cells and assessing changes to the structure/morphology of the filter paper separator and carbon-electrode cell components. The separator from the KBr/TBABr cell appeared identical to the pristine paper separator before cycling, while the separators from the other cells are covered with a black solid (see pictures in FIG. 20). Raman spectra collected of the separator from the KBr/TBABr cell shows no clear peaks, and are identical to the Raman spectrum obtained from a pristine separator (FIG. 13(a)). However, Raman spectra of the separators from the KBr and KBr/MEPBr cells show peaks at approximately 1340 $cm^{-1}$ and 1610 $cm^{-1}$ which can be assigned to the D band and G band, respectively, of activated carbon.[44] The same peaks are observed for the non-cycled carbon electrode, indicating that the black solid observed in the separator was shed from the electrode. A control experiment where a pristine separator is soaked in $Br_2/Br_3^-$ solution (that mimics the charged state of the cell) demonstrated no color change of the separator in the absence of the carbon electrode.

Electron microscopy showed that the electrode exhibited little morphology change when cycled in a KBr/TBABr cell (FIG. 13(d)). In contrast, cracks and partial pulverization of carbon particulates are observed on the electrode surface after cycling in KBr (FIG. 13(c)) and KBr/MEPBr electrolytes (FIG. 13e), providing evidence of carbon electrode degradation and its subsequent deposition onto the separator (TEM images of the positive electrodes after cycling in FIGS. 21(a)-21(d). Elemental analysis by EDX of the positive electrodes from the KBr and KBr/MEPBr cells after cycling further confirm decreased carbon content (relative to F in the inert PTFE binder) compared to the electrode before cycling (Table S4).

Based on the experimental results, the present disclosure proposes that electrochemical intercalation induced by reactive bromine/polybromide causes permanent electrode degradation with time and thus irreversible fading of the KBr and KBr/MEPBr cells.[45,46] When $TBA^+$ is present, the concentration of non-complexed $Br_2/Br_3^-$ is significantly reduced, thereby slowing irreversible side reactions and largely preventing electrode degradation upon repeated charge/discharge cycles. This $TBA^+$-induced solid complexation suppresses the permanent capacity loss mechanism. Overall, these results show an efficient way to utilize the bromide catholyte with readily available TBABr, the simple addition of which simultaneously addresses the capacity loss as well as self-discharge problems for static bromide-enhanced redox ECs.

c. Design of a High-Performance Viologen/Br Dual-Redox EC with the Addition of Tetrabutylammonium Complexing Agent For maximum faradaic energy storage, redox ECs should utilize redox-active electrolytes at both the positive electrode (catholyte) and negative electrode (anolyte) concurrently (dual-redox enhanced electrochemical capacitors; dual-redox ECs). Illustrative embodiments of the present invention choose viologen (V) as a model anolyte to match the redox activity of the bromide catholyte and test the utility of tetrabutylammonium complexing agent in a full cell. For the V/Br systems, (1) cycling stability largely depends on effective bromine storage in the positive electrode,[36] (2) only viologens with hydrophobic substituents, e.g., pentyl (PV)[36] or heptyl viologen (HV),[26] can function as an efficient $Br_3^-$ complexing agent, limiting the capacity for faradaic energy storage due to their low solubility (e.g., <0.2 M for HV), and thus (3) it is desirable to enhance energy density by using highly soluble viologens to increase the available concentration of anolyte while finding other means to complex $Br_3^-$ and maintain cycling stability.

Figure 22C:
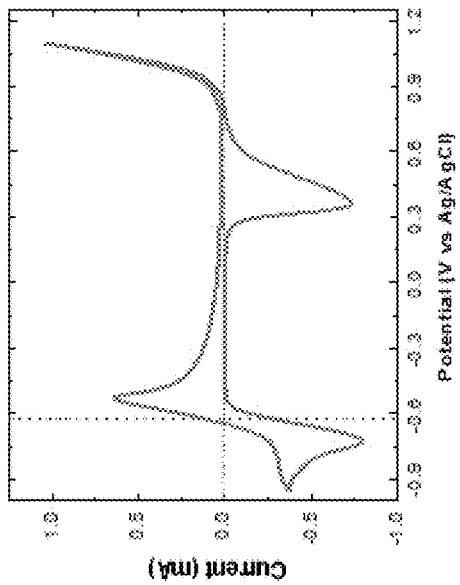
FIGS. 22(a)-22(c) are cyclic voltammograms of 0.1 M $EVBr_2$ (FIG. 22(a)) and 0.1 M $EVBr_2$/0.1 M NaBr (FIGS. 22(b) and 22(c), wherein the data in FIG. 22(b) was obtained by scanning from 0 V to −0.95 V (purple curve) and 0 V to +1.1 V (orange curve), separately, and the data in FIG. 22(c) was obtained by scanning over the full range of +1.1 V to −0.95 V (scan rate: 20 mV/s); glassy carbon served as the working electrode and a Pt wire served as the counter electrode. As reference, an Ag/AgCl electrode was used.
Figure 22B:
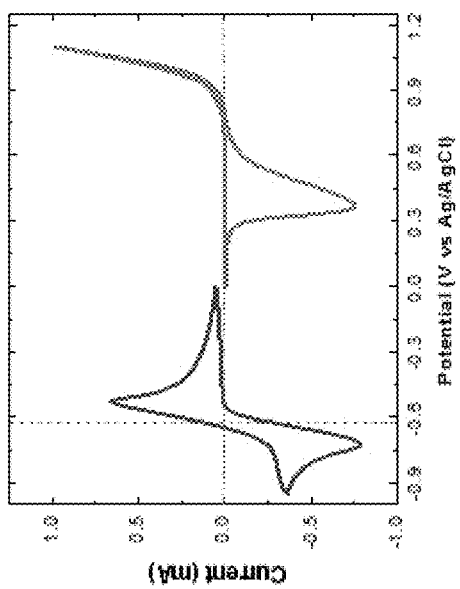
Figure 22A:
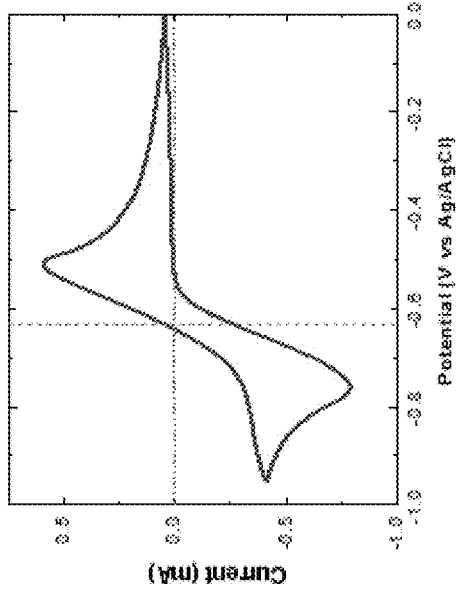

The present disclosure envisioned that addition of TBABr to V/Br electrolytes should (1) suppress the fading mechanism at the positive electrode and (2) enable the use of more-soluble, short-alkyl-chain viologens at the negative electrode, in order to (3) maintain cycling stability while producing high energy density in a single device. To verify these hypotheses, readily available ethyl viologen (1,1'-diethyl-4,4'-bipyridinium dibromide; EV) was selected as an anolyte due to its high solubility (>2 M) and the stability of $EV^{2+}/EV^{+}$ redox couple in aqueous electrolytes.[47] Additionally, $EVBr_2$ shows good solution compatibility with a bromide catholyte (e.g., NaBr) in an analytical voltammetry cell (FIGS. 22(a)-22(c)).

Figure 14A:
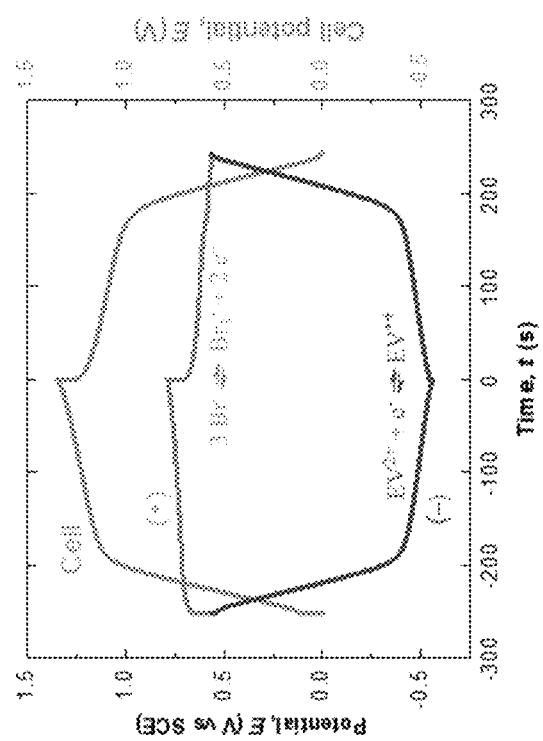
Figure 14B:
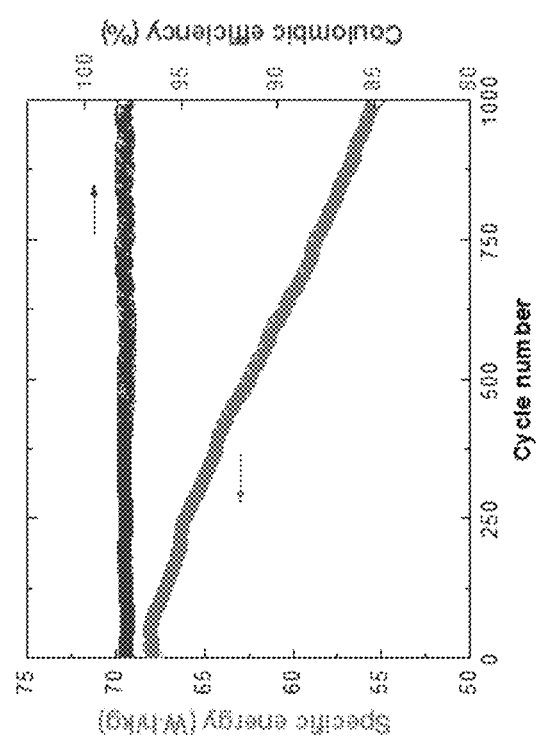

First, a control cell with a readily soluble 1.2 M $EVBr_2$/3 M NaBr electrolyte, without additional complexing agent, was assembled and tested. Three-electrode GCD profiles show dual faradaic responses at both positive and negative electrodes, corresponding to $Br^-$ oxidation to $Br_3^-$ and $EV^{2+}$ reduction to $EV^{+}$, respectively, upon charging (FIG. 14(a)). This cell produced a specific energy of ~68 W·h/kg at 1 A/g, but the cell capacity faded and only retained 82% of the initial energy over 1000 cycles (FIG. 14(b)). This poor cycle life confirms that short-alkyl-chain viologens do not effectively retain reactive $Br_2/Br_3^-$, which decreases cell stability. To improve the cycle life of EV/Br redox ECs, electrolyte design must utilize a $Br_3^-$ complexing agent that has stronger $Br_3^-$ complexing capacity than EV.

The degree of (solid) complexation of TBABr with $Br_3^-$, relative to EV, was tested by determining how much EV precipitates from an aqueous $Br_3^-$ solution with and without this complexing agent additive. The amount of precipitated EV was indirectly quantified by measuring the concentration of the remaining viologen in solution with ultraviolet-visible spectroscopy (UV-vis).

Figure 15:
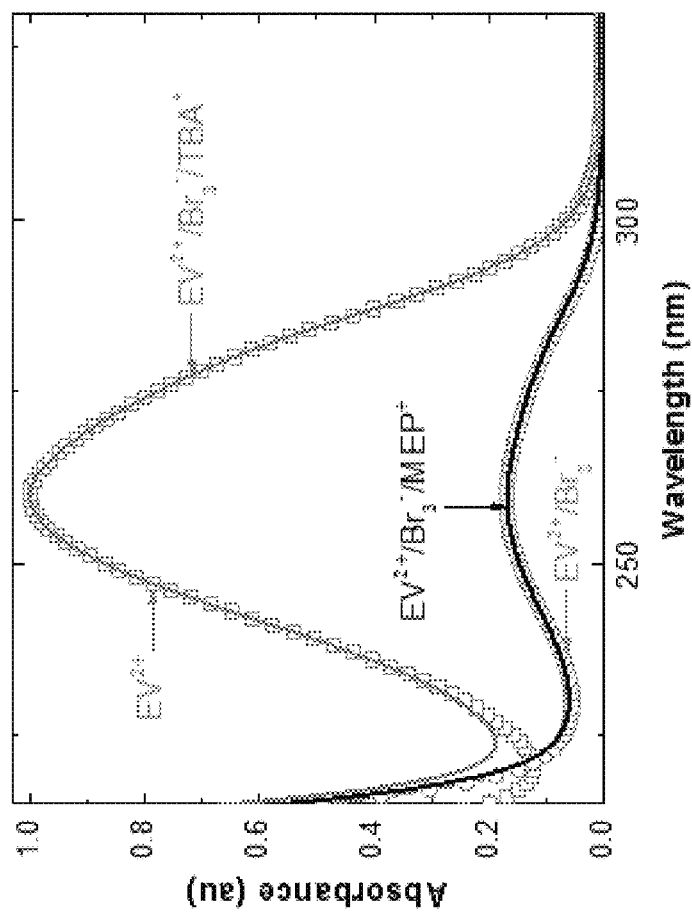
FIG. 15 plots UV-vis absorption spectra quantifying the concentration of $EV^{2+}$ remaining dissolved in the supernatant without $Br_3^-$ ($EV^{2+}$; blue open-square curve), with the addition of $Br_3^-$ ($EV^{2+}$/$Br_3^-$; blue open-circle curve), with $Br_3^-$ and TBABr ($EV^{2+}$/$Br_3^-$/$TBA^+$; orange solid curve), and with $Br_3^-$ and MEPBr ($EV^{2+}$/$Br_3^-$/$MEP^+$; black solid curve), respectively, wherein the spectra are normalized to the absorption maxima of the $EV^{2+}$ ($\lambda_{max}$=260 nm) (experimental details for the UV-vis measurements are in the experimental section).

FIG. 15 shows that the addition of $Br_3^-$ decreased the concentration of EV dissolved in the solution by ca. 83% due to precipitation of the nominally [$EV^{2+}$·$2Br_3^-$] solid complex (EV'; blue open-square curve vs $EV^{2+}/Br_3^-$; blue open-circle curve), which still leaves substantial free, non-complexed $Br_3^-$ present in the solution, causing the poor cycling life of the EV/Br cell. Importantly, when TBABr was added together with $Br_3^-$ and EV, EV remained completely dissolved ($EV^{2+}$; blue open-square curve vs $EV^{2+}/Br_3^-$/TBA$^+$; orange solid curve). These UV-vis results suggest that TBABr has a greater $Br_3^-$ complexing capacity than $EV^{2+}$ and that [TBA$^+$·$Br_3^-$] solid complex is preferentially formed. Notably, MEPBr, a common $Br_2/Br_3^-$ complexing agent for aqueous flow battery systems, does not induce any solid complexation/precipitation with $Br_3^-$ in the presence of $EV^{2+}$ ($EV^{2+}/Br_3^-$; blue open-circle curve vs $EV^{2+}/Br_3^-$/MEP$^+$; black solid curve), which correlates with the poor stability and fast self-discharge results obtained for the previous asymmetric KBr/MEPBr cell. This relative interaction strength, i.e., MEP$^+$<$EV^{2+}$<TBA$^+$, is consistent with previous findings that indicate hydrophobicity enhances solid complexation,[36,37] and suggests that TBABr should be a suitable complexing agent for EV/Br dual-redox ECs.

A two-electrode cell with a 1.2 M $EVBr_2$/2.88 M NaBr/0.12 M TBABr electrolyte (i.e., 10 mol % addition of TBABr based on the molar concentration of $EVBr_2$), paper separator, and symmetric activated carbon electrodes (areal mass loading of 12.7 mg/cm$^2$) was assembled and tested by GCD. The concentration of EV and Br were set at 1.2 M and 3 M, respectively, for the comparison with standard EV/Br cell, and 10 mol % addition of TBABr ensures that this electrolyte concentration is readily soluble, thus providing simple solution preparation and lower viscosity. The cell (denoted as EV/TBA/Br) produced ~64 W·h/kg at 1 A/g with ~97% Coulombic efficiency and a high energy efficiency of ~84% when charged/discharged between 0 V and 1.35 V. Most importantly, the specific energy of the cell degraded by only ~3% over 1000 cycles compared to 18% capacity loss of the cell without TBABr cycled under the same conditions (FIG. 16(a)). For the long-term cycling test, the EV/TBA/Br cell maintained stability with 90% energy retention over 5000 cycles (charge/discharge at 2 A/g) and exhibited ~4% degradation over an additional 7000 cycles when operated from 0 V to 1.3 V at the same current density (FIG. 16(b)). This stability increase shows that the superior performance of short-alkyl-chain viologens can be maintained without sacrificing lifetime through the addition of TBABr. Furthermore, the EV/TBA/Br cell shows good self-discharge characteristics with η$_R$ (6 h)=53% when charged to 1.3 V and η$_R$ (6 h)=45% when charged to 1.35 V. For these two conditions the open circuit voltage losses are only 13% and 16%, respectively, comparable to other redox ECs with costly ion-selective membrane separators (FIG. 16(c); Table 1). The Ragone plot in FIG. 16(d) shows that the EV/TBA/Br cell provides a power performance higher than 3 kW/kg while still retaining ~15 W·h/kg energy density. This cell's energy, power, stability, and self-discharge performance are compared with previous reports of aqueous redox ECs in Table 1. To provide further performance comparison, an aqueous EDLC (1 M $Na_2SO_4$ electrolyte) and a commercial non-aqueous EDLC (BCAP0001 P270 T01, Maxwell Technologies) were tested as control/comparison devices. FIG. 16(d) shows that the EV/TBA/Br cell produced specific energy well above the 1 M $Na_2SO_4$ cell (black curve) at all power rates. Compared to the commercial non-aqueous cell, this cell delivered as high as ~250% increased specific energy over a wide range of power rates up to ~3 kW/kg. Overall, these results further demonstrate that the EV/TBA/Br redox EC system substantially improves energy as well as power densities of aqueous EDLCs by adding dual faradaic reactions at both the positive and negative electrodes, without negatively impacting cycle life.

TABLE 1

Comparison of the (selected) previous reports of aqueous redox ECs

| Electrode | Redox electrolyte | Specific energy at W/kg (or A/g) | Cycling stability | Separator | Self-discharge rate | Ref. |
|---|---|---|---|---|---|---|
| AC | $SnSO_4$/ $VOSO_4$ | 75 Wh/kg (at 0.055 A/g) | 85% (4500 cycles) | Anion exchange membrane | 1.4 V→1.16 V (10 h) | 19 |
| AC | $EVBr_2$/ TBABr/ NaBr | 64 Wh/kg (at 1 A/g) | 90% (5000 cycles to 1.35 V) 96% (7000 cycles to 1.3 V) | Filter paper | 1.35 V→1.13 V (6 h) | this work |
| AC | $SnF_2$/ $VOSO_4$/ $H_2SO_4$ | 46 Wh/kg (at 1 A/g) | 80% (6500 cycles) | Anion exchange membrane | 1.4 V→1.2 V (10 h) | 23 |
| Reduced GO | KI/ KOH | 44 Wh/kg (at 0.83 A/g) | ~80% (5000 cycles) | polypropylene | Not available (N/A) | 31 |
| Functionalized CNT | KBr/ $Na_2SO_4$ | 28.3 Wh/kg (at 372 W/kg) | 86.3% (10000 cycles) | Cation exchange membrane | N/A | 28 |
| AC | $K_3Fe(CN)_6$ | 28.3 Wh/kg (at 0.05 A/g) | 80% (9000 cycles) | Cation exchange membrane | 0.8 V → 0.65 V (10 h) | 21 |
| AC | $EVBr_2$/ $H_2SO_4$ | 23 Wh/kg (at 0.25 A/g) | No degradation (1000 cycles) | polypropylene | N/A | 47 |
| graphene hydrogel | hydroquinone/ $H_2SO_4$ $CuSO_4$/ $H_2SO_4$ | 8.9 Wh/kg$^a$ (at 252 W/kg$^a$) 6.7 Wh/kg$^a$ (at 360 W/kg$^a$) | 80% (1,000 cycles) ~99% (1,000 cycles) | Nafion ® 117 membrane porous cellulose acetate | 0.8 V → 0.3 V (~1.5 h) 49%$^a$ of initial energy (1 h) | 24 |

Note:
The data are arranged by descending specific energy reported without considering rates. (GO: graphene oxide; CNT: carbon nanotube)
$^a$The values are not explicitly reported in the paper, and estimated numbers are from the previously reported literature.[26]

d. Pentyl Viologen, TBABr, and NaBr System

Testing of a comprising an electrolyte consisting of 1M $PVBr_2$, 0.1M TBABr, and 3M NaBr, wherein TBABr was used as an additive, produced a specific energy of 43 Wh/kg while maintaining stability, retaining >95% of energy density over 4000 cycles. In addition, still great suppression of self-discharge was obtained despite having a large concentration of complexes at the electrode surface (83% energy retention after 6 h open circuit).

To demonstrate the symmetric nature of the device and the mobility of the redox couples, the inventors reversed the polarity of the cell and ran the same cycling tests. The performance is notably unchanged even though the device is being operated "backwards."

Figure 23A:
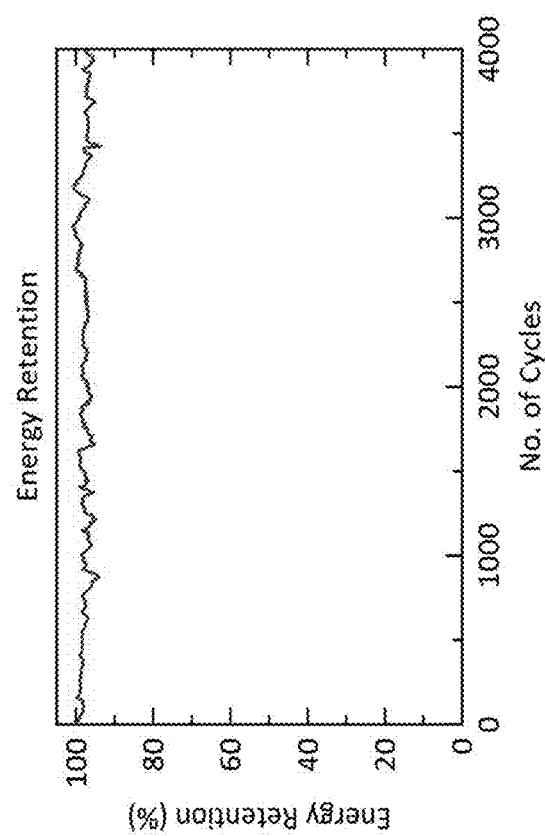
FIG. 23(a) plots galvanostatic cycling of a PV/TBABr/NaBr cell with a whatman separator (charged/discharged at a rate of 1 A/g).

FIG. 23(a) plots galvanostatic cycling of PV/TBABr/NaBr cell with Whatman separator; charged/discharged at a rate of 1 A/g.

Figure 23B:
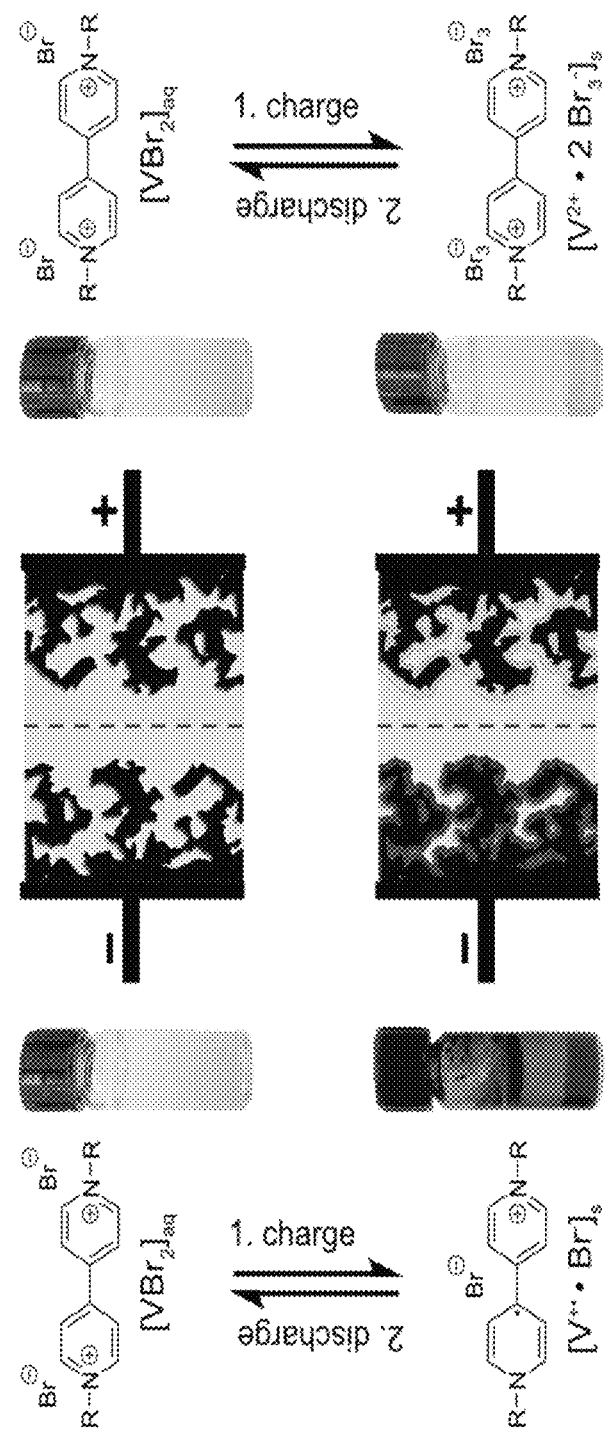
FIG. 23(b) is a summary of the viologen bromide system, illustrating a single electrolyte is used with a non-ion-selective separator, where anolyte and catholyte are fully mixed and fully compatible. By optimizing the functional group, a solid complex is reversibly electroprecipitated at each electrode to improve cycling stability and decrease self-discharge. The redox couples come from a single organic salt that dissociates into anionic and cationic species, each of which acts as a charge-storing redox couple at one electrode and as a complexing agent at the other electrode.
Figure 23D:
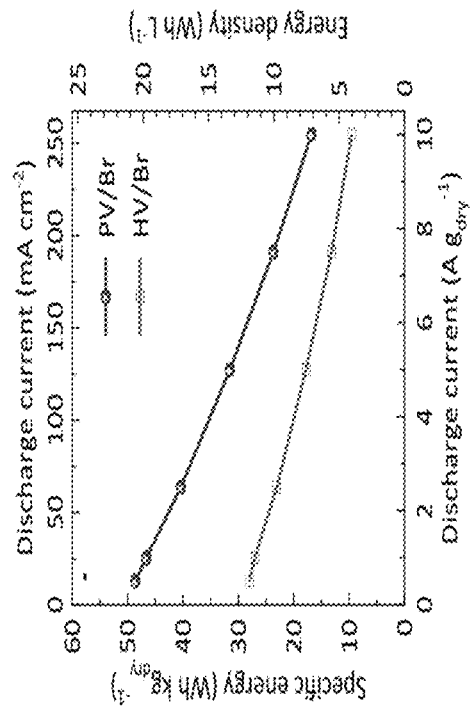
FIGS. 23(c)-23(f) plot performance of a 1 M $PVBr_2$/3 M NaBr cells, showing, in FIG. 23 (c) GCD potential profiles for the cathode (red curve), anode (blue curve), and total cell (green curve), FIG. 23(d) specific energy of PV/Br and HV/Br cells at different discharge rates, FIG. 23 (e) energy retention is 97% over 10,000 cycles at 2.5 $A/g_{dry}$ with 99.9% coulombic efficiency, and FIG. 23(f) stable cycling with the leads switched every 200 cycles, repeatedly reversing the polarity. Additionally these cells retain more than 75% of initial discharge energy after 6 hours at open circuit.
Figure 23F:
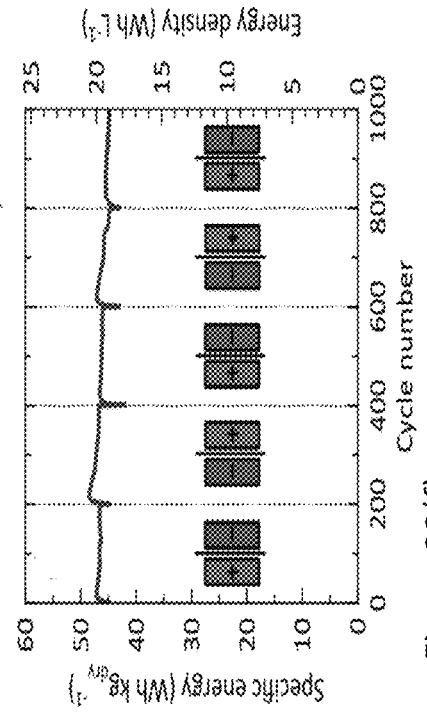
Figure 23C:
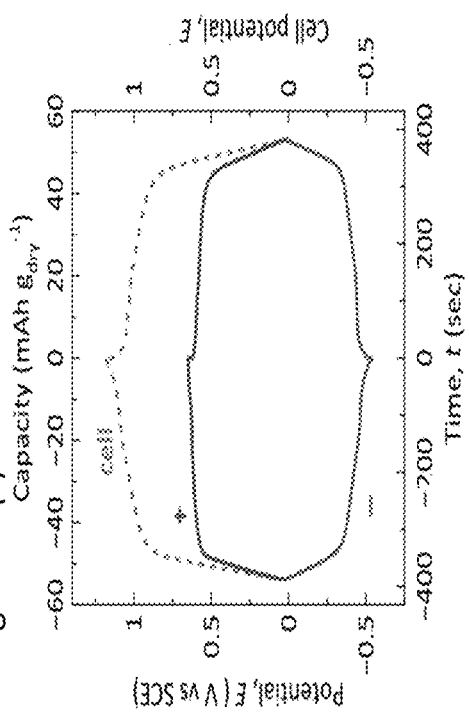
Figure 23E:
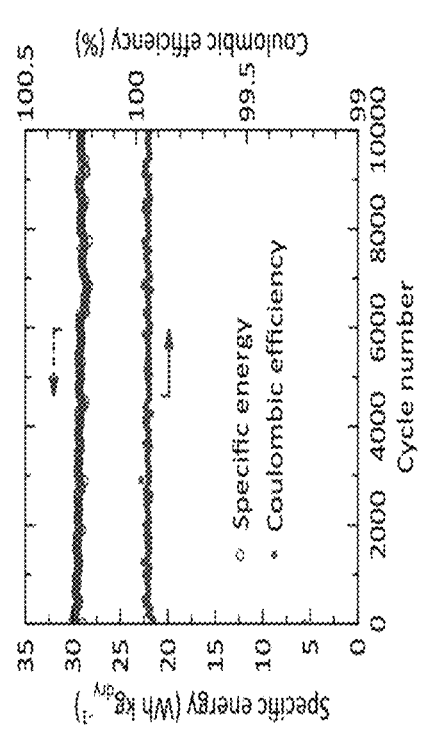

The performance of the n-alkyl viologen redox-ECs was optimized. The mechanism responsible for the stability of heptyl viologen bromide Gen II chemistry was formalized by the inventors'. This "dual redox couple counterion-induced reversible complexation" mechanism is summarized in FIG. 23(b). Surprisingly and unexpectedly, with an optimized pentyl viologen bromide electrolyte (1 M PV/3 M NaBr), the slow self-discharge and excellent cycling stability of heptyl viologen electrolyte and the high specific energy of the methyl viologen electrolyte could be simultaneously realized in a single system. FIGS. 23(e)-(f) illustrate the performance of the optimized pentyl viologen chemistry.

In summary, the present disclosure reports on a novel paradigm shift for the conventional use of a mobile, liquid state to complex $Br_3^-$ and a fundamentally different and unexpected solution for complexing/storing $Br_3^-$ in aqueous redox ECs. The present disclosure demonstrates with microscopic-level evidence that reversible solid complexation of $Br^-/Br_3^-$ redox couple induced by tetrabutylammonium bromide effectively stores reactive and diffusive bromine within the pores of the carbon electrodes. This mechanism suppresses unwanted chemical reactivity and cross-diffusion of $Br_2/Br_3^-$ that results in improved cycling stability and self-discharge rates of redox ECs. As illustrated herein, this fundamental understanding of chemical and electrochemical processes at the electrolyte/electrode interface is used to develop a high-performance dual-redox EC.

Specifically, this fundamental understanding of the electrolyte chemistry has led to an improved system highlighting the use of newly synthesized pentyl viologen ($PVBr_2$) with the addition of tetrabutylammonium bromide (TBABr) as an additive complexing agent. Pentyl viologen combines the stability of heptyl viologen with the solubility of methyl viologen while TBABr provides additional $Br_3^-$ complexing power at cathode. Current system produces record high of 43 Wh/kg with good stability and self-discharge rate This dual-redox EC, which integrates TBABr with an ethyl or pentyl viologen anolyte and a bromide catholyte, produces a record specific energy with stable cycling at high power levels: Addition of tetrabutylammonium surprisingly and unexpectedly improves all aspects of device performance including stability, energy and power density without adding complexity to the fabrication process. The system can be assembled without a dry room or glove box, uses aqueous electrolyte with readily available salts, and has a cost-effective paper separator that avoids the use of expensive ion-selective membranes. These attributes address hurdles to practical commercialization, and low costs of production may be possible. The systematic approach presented herein to efficiently utilize bromide catholyte and design of a high-performance dual-redox EC should be informative and promise to be readily applicable for a wide variety of energy storage applications, especially for the science of hybrid electrochemical capacitors (e.g., bromide catholyte at positive electrode with faradaic battery-type or pseudocapacitive negative electrode).

4. Fourth Example: Bipolar Pouch Cell

Figure 24:
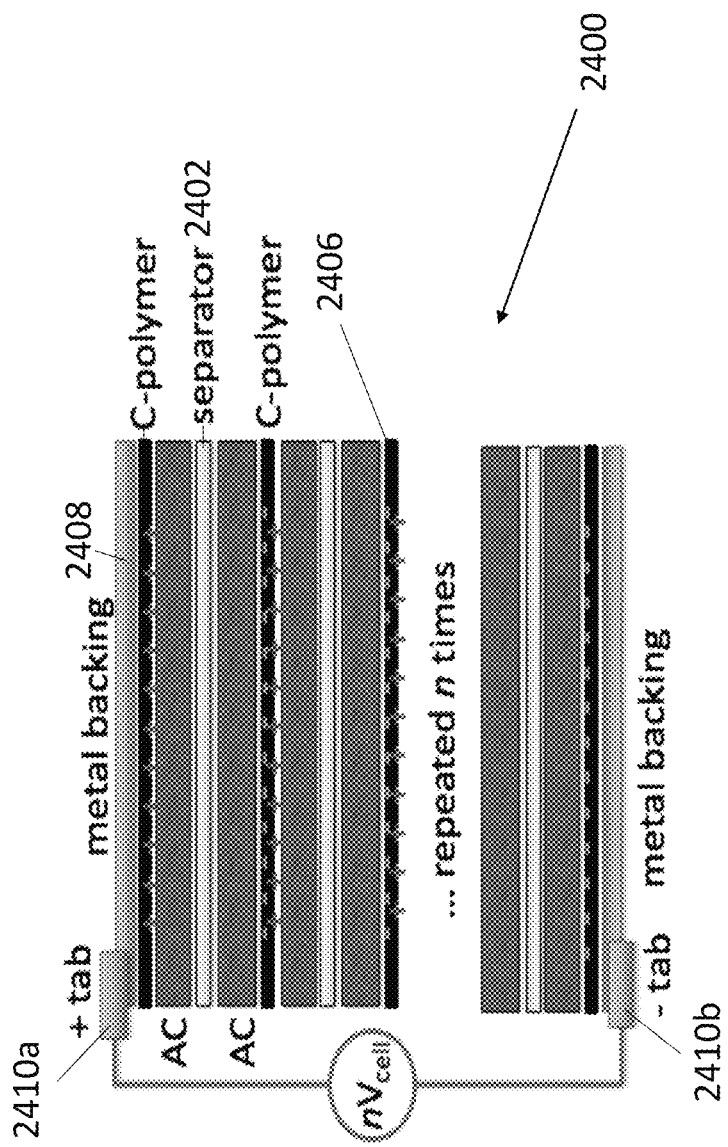
FIG. 24 shows a bipolar pouch cell design for n cells in series.

Only carbon-based current collector materials have sufficient corrosion resistance for many aqueous electrolytes, including viologen bromide systems, but the conductivity of these materials is too low for a conventional spirally wound cell. FIG. 24 illustrates a new bipolar cell design to address this problem. In this design, multiple cells 2400 comprised of activated carbon (AC) electrodes, an electrolyte, a separator 2402, carbon polymer (C-polymer) composite current collectors 2406 are stacked in a series configuration and current only travels a short distance through the carbon-polymer (C-polymer) composite current collectors 2406 between cells, minimizing the total resistance. The voltage of the series stack ($nV_{cell}$) is equal to the voltage $V_{cell}$ of a single cell multiplied by the number n of cells in the stack. The current collectors between individual cells are bipolar, because one current collector is serving as a positive current collector of one cell and a negative current collector of the adjacent cell. The current collectors on the top and bottom of the stack are not bipolar. Also shown are metal backing 2408 and positive (+) and negative (−) tabs or contacts 2410a, 2410b.

Carbon has the additional advantage of better contact resistance with electrode materials due to the lack of a metal oxide passivation layer. It also suppresses hydrogen and oxygen evolution due to large kinetic overpotentials, which in some systems will effectively widen the practical electrochemical stability window of aqueous electrolytes. The use of carbon as a current collector is well-explored. Expanded graphite foil has been shown to be a suitable current collector for aqueous supercapacitors, but one drawback is its porous structure, which makes it permeable to electrolyte. Carbon paper has also been used, but is too fragile for practical use. To get around these problems in flow batteries and fuel cells, electrolyte-impermeable and mechanically strong thermoplastic/carbon composite current collectors are used. However, these materials are thick, rigid plates with flow channels incorporated, making them unattractive for use in compact, portable cells. In non-flow systems, thin, flexible, lightweight carbon/plastic composites would be preferable. The present disclosure has identified a commercially available candidate current collector material known as Caplinq Linqstat XVCF. This is a 70 micrometer thick flexible film of carbon black-impregnated polyethylene (CB-PE) manufactured for antistatic packaging applications with a sheet resistance of 75-500Ω/□. The material costs <$1.6/m$^2$, has high mechanical strength and is heat-sealable. These attributes mean that a single low-cost material can serve simultaneously as a mechanical support, bipolar current collector, and seal.

Figure 25:
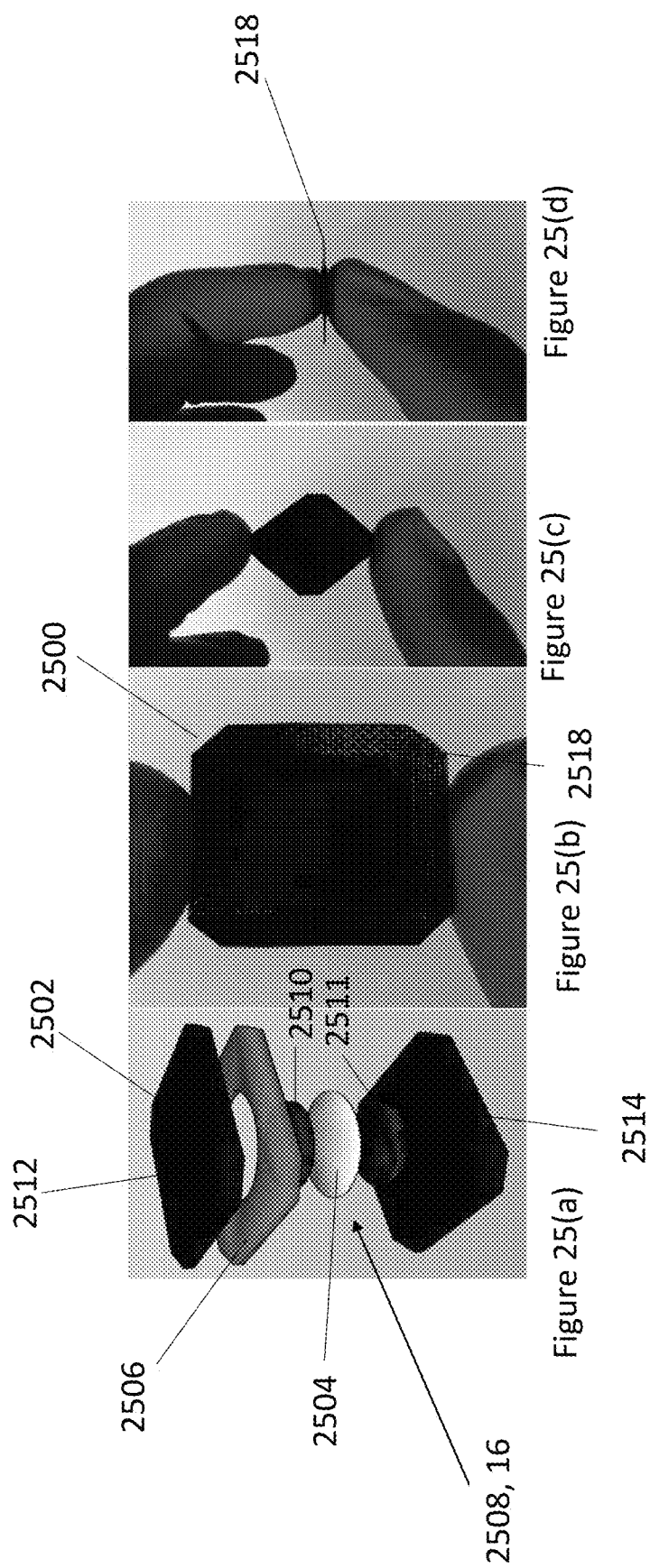
FIGS. 25(a)-25(d) show a pouch cell with carbon black-impregnated polyethylene (CB-PE) current collectors. The current collectors are separated by non-conducting polyethylene and the edges of the cell are heat-sealed.

The first step in realizing this design was assembling a single-cell pouch using the CB-PE film. The resulting pouch device 2500 is shown in FIGS. 25(a0-25(d), and comprises current collectors 2502 (comprising CB-PE film), a separator 2504, a plastic spacer 2506, an electrolyte 2508, and electrodes 2510 and 2511 on either side of the separator. The walls 2512, 2514 of the pouch 2500 include the current collectors 2502 and are sealed to the insulating plastic spacer 2506 with a heat-seal 2518, so that the electrodes 2510 and 2511, the electrolyte 2508, and the separator 2504 are sealed within the pouch 2500.

Figure 26:
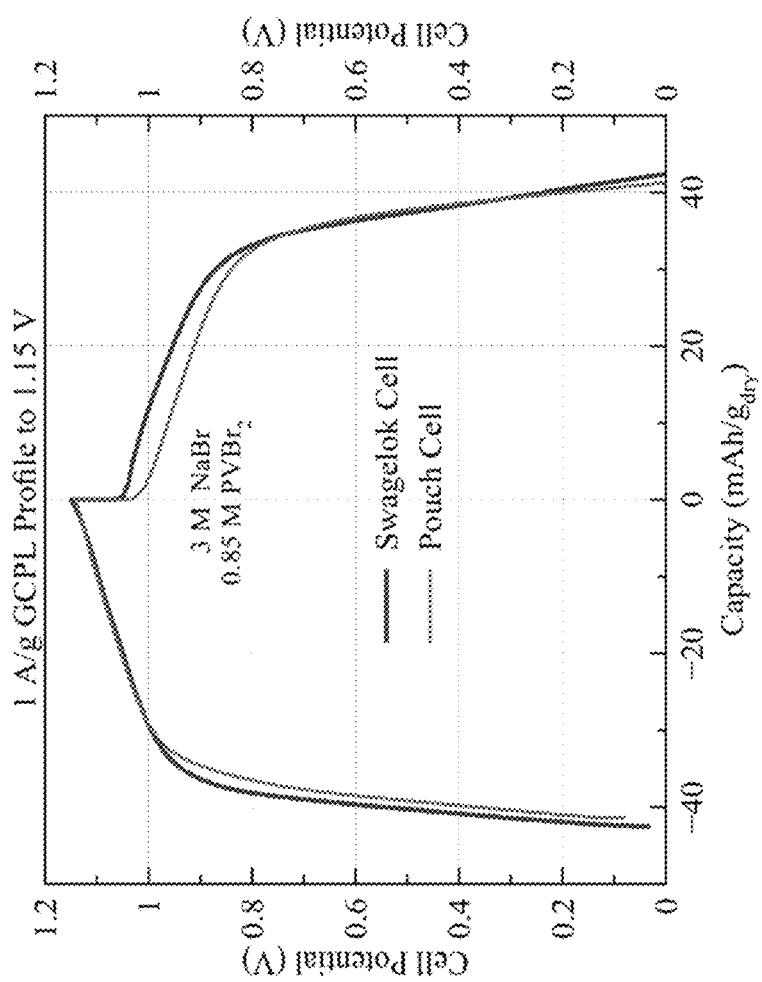
FIG. 26 shows galvanostatic cycling profiles at 1 $A/g_{dry}$ for a cell with 3 M NaBr/0.85 M $PVBr_2$ electrolyte in a glassy carbon Swagelok cell and in a PE-CB pouch cell.
Figure 27:
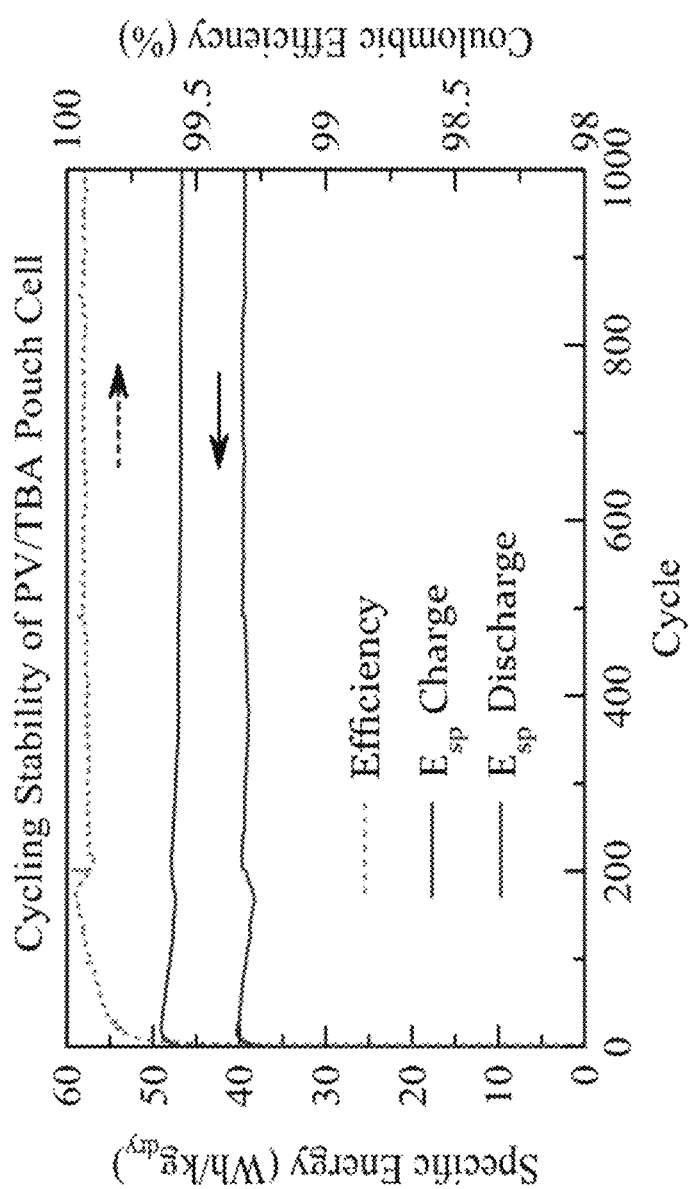
FIG. 27 plots cycling stability for the PE-CB pouch cell with 0.85 M $PVBr_2$/0.1 M TBABr/3 M NaBr electrolyte cycled at 1 $A/g_{dry}$ to 1.25 V.

The device shows very similar performance to the same chemistry in a glassy carbon Swagelok cell, as illustrated in FIG. 26, and high stability, as illustrated in FIG. 27.

Figure 28B:
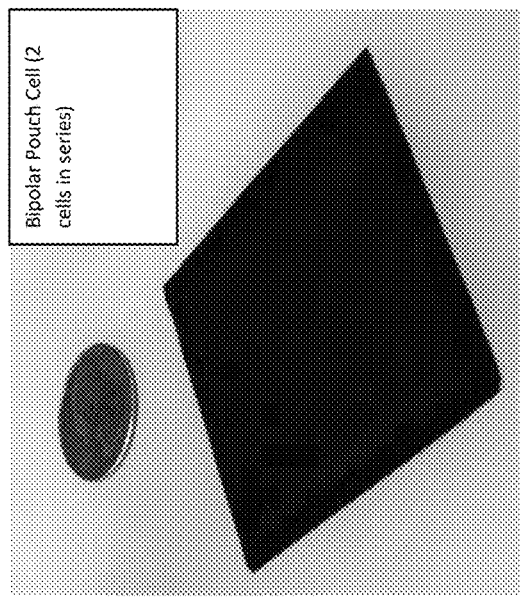
FIGS. 28(a)-28(d) are schematics for a bipolar pouch cell (FIG. 28(a)) with CB-PE composite current collectors and the concept reduced to practice with large square electrodes instead of a small circular stack (FIG. 28(b)).
Figure 28A:
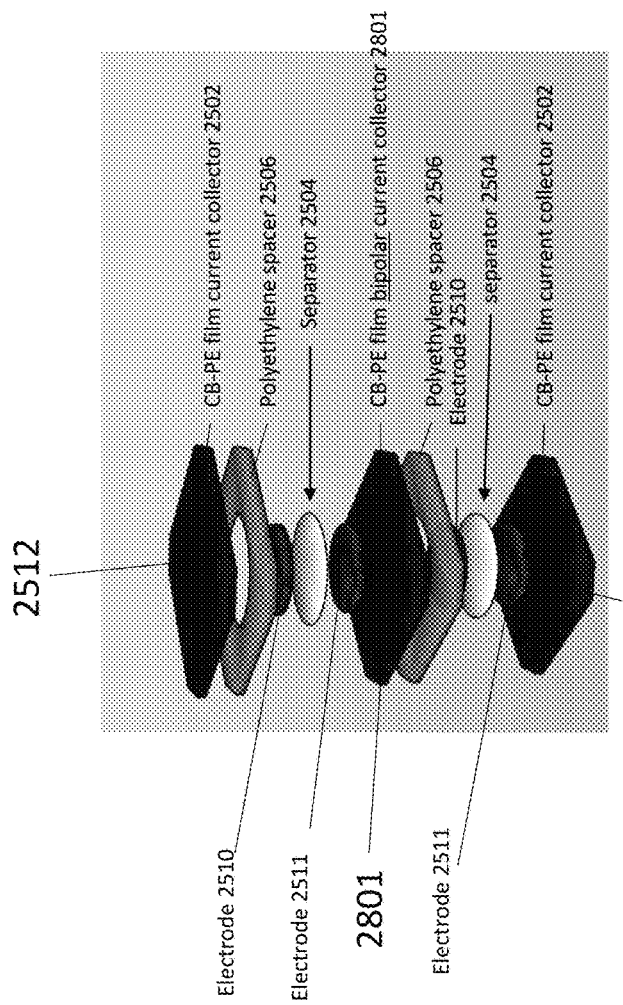
Figure 28D:
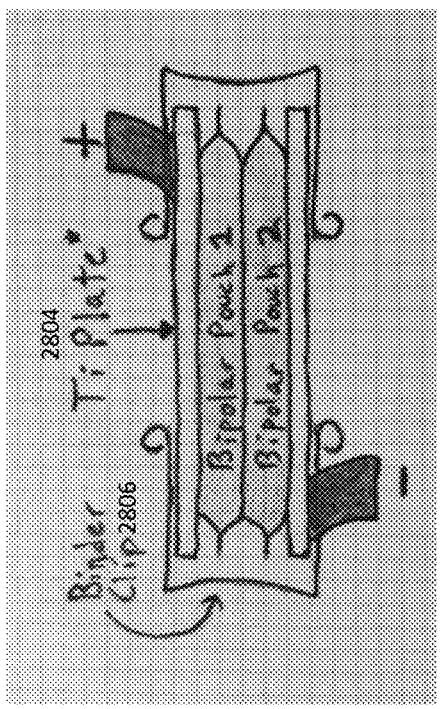
Figure 28C:
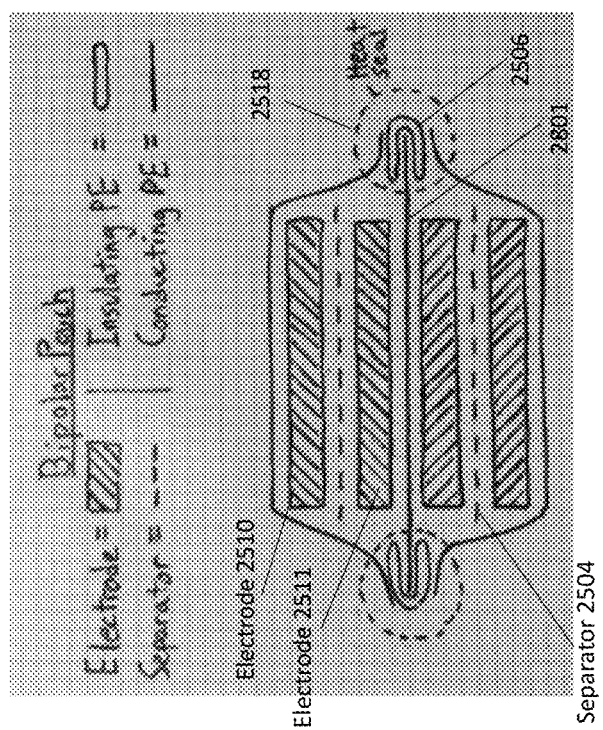

FIG. 28(a) illustrates constructing a series stack of 2 of the individual cells from FIGS. 25(a)-25(d) so that the middle current collector 2801 is bipolar. FIG. 28(b) shows a larger version of cell in FIG. 28(a) where the electrodes 2510, 2511 are squares measuring 4 cm by 4 cm instead of small 1 cm OD circles. FIG. 28(c) shows a cross-sectional view of the inside of the bipolar pouch cell from FIG. 28(b), further illustrating the conducting polyethylene (PE) 2801 and the insulating polyethylene 2506. Individual bipolar pouch cell stacks could comprise any number of series-connected cells, and are not limited to just two cells, as shown in simplified form in FIG. 24. Finally, FIG. 28(d) illustrates how multiple (in this case 2) bipolar pouch cell stacks 2500 can be stacked (resulting in this case in a total of four cells in series). Pressurizing the stack between two external metal plates 2804 (e.g., titanium plates) using springs or binder clips 2806 makes a device that can charge to 4.8 V (1.2 V per cell×4 cells). Also shown are positive (+) and negative (−) tabs or contacts.

Figure 29B:
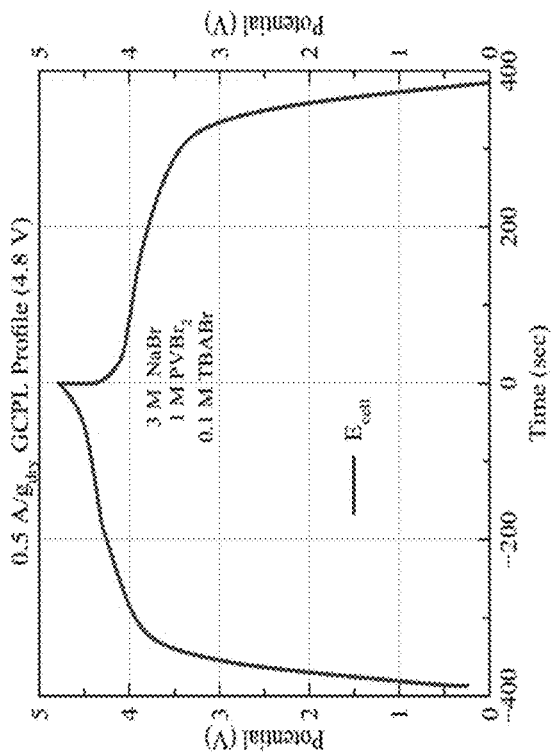
FIGS. 29(a)-29(b) plot specific charge/discharge energy and Coulombic efficiency normalized to electrode mass (FIG. 29(a)) and typical galvanostatic charge/discharge potential profile (FIG. 29(b)) for a PE-CB pouch cell with 1 M $PVBr_2$/0.1 M TBABr/3 M NaBr electrolyte cycled at 0.5 $A/g_{dry}$ to 4.8 V.
Figure 29A:
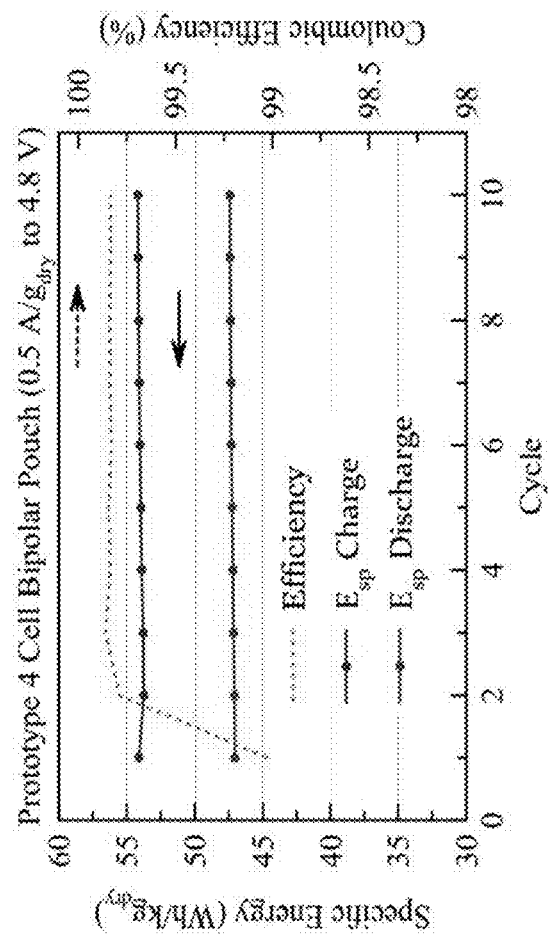

Typical galvanostatic cycling data and a charge/discharge potential profile are shown in FIGS. 29(a)-29(b).

Figure 30E:
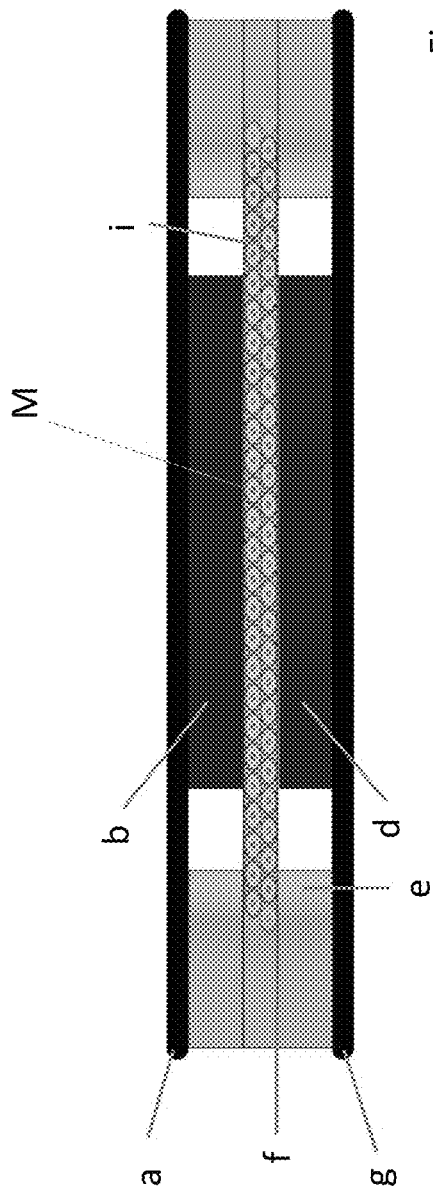
Figure 30F:
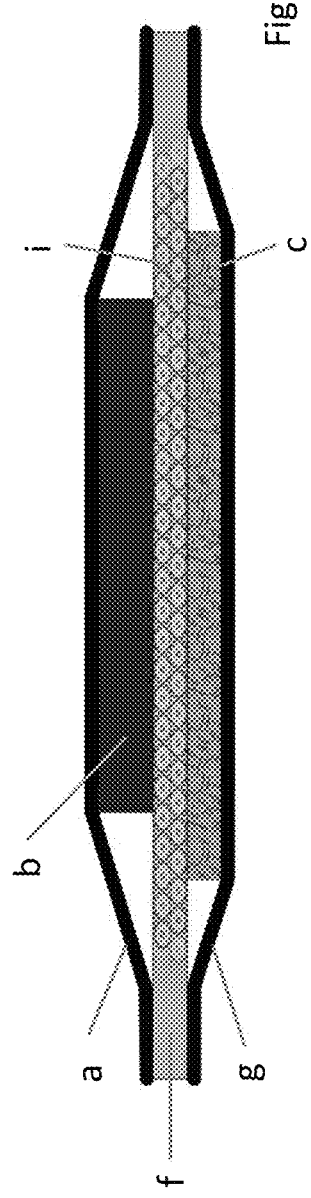

FIGS. 30(a)-30(f) show example cross sections of different pouch cell geometries, wherein one or more of the pouch cell geometries comprise positive current collector a, positive electrode b, separator c, negative electrode d, insulating plastic spacer layer e, heat seal f, negative current collector g, bipolar current collector h, and in the case of FIGS. 30(e) and 30(f), microporous polyethylene separator i. The cells inside the pouches could be circular, square, or any desired geometric shape.

a. Pouch Embodiment 1: Pouch Cell for Viologen Bromide Type System

FIG. 30(a) (single cell) and FIG. 30(b) (multiple cell stack) show typical cross sections of pouch cells for a viologen bromide system which have both a positive and a negative electrode. Here the separator is larger than the electrodes but smaller than the aperture of the insulating plastic spacer. This geometry could work with any battery or supercapacitor that has solid positive and negative electrodes and solid active materials, a redox-active electrolyte, or a combination of the two.

b. Pouch Embodiment 2: Pouch Cell for a Zinc Bromine Type System

FIG. 30(c) (single cell) and FIG. 30(d) (multiple cell stack) show typical cross sections of a pouch cells for zinc bromine systems, which have only a positive electrode (the negative electrode is eventually deposited as zinc metal from the electrolyte inside the separator). Here the separator is larger than the positive electrode and larger than the aperture of the insulating plastic spacer, but still smaller than the heat-sealed perimeter of the cell. This partial overlap of the separator by the spacer helps prevent zinc metal dendrites from growing around the edge of the separator. Such an overlap could be used in the example illustrated in FIG. 30(a) as well, but is less necessary in the case of viologens or other battery or supercapacitor systems.

The pouch embodiment illustrated in FIG. 30(a) comprises thick insulating plastic spacers while the pouch embodiment illustrated in FIG. 30(b) comprises thin plastic spacers, but the thick and thin spacers could be interchanged between the two designs. Thin spacers cause the current collectors to deform more to meet for the heat seal, therefore thicker spacers may be preferable for stacks of large numbers of cells. Thick spacers keep the current collectors flatter and more parallel so that the outermost current collectors do not have to bend as dramatically.

Multiple cell stacks could mean 2 cells in series to 10's of cells in series. As discussed herein (see e.g., FIG. 28(d)), multiple pouches each comprising multiple stacked cells can also be connected together in parallel or series configurations in a larger final battery pack.

c. Pouch Embodiment 3

FIG. 30(e) shows how the separator c and insulating plastic spacer e could be integrated into one component by using a microporous polyethylene separator i. The micropores M of the polyethylene collapse in the region of the heat-seal, making that region impermeable to electrolyte and serving the same function typically addressed by the plastic spacer. This design provides a simplified construction, better separation of the two sides of the cell, and better mechanical properties. It may also enable the use of binder-less electrode slurries that fill the entirety of the two separated sealed compartments, instead of typical freestanding electrode films/pellets that must be solid to avoid flowing around the edge of the separator and shorting the cell.

d. Pouch Embodiment 4

FIG. 30(f) shows the microporous polyethylene separator concept adapted for a zinc bromine system, where instead of a negative electrode d there is a second separator c with large porosity to provide volume for the zinc metal to deposit into.

Only single cells are shown in pouch embodiments 3 and 4; however, pouch embodiments 3 and 4 may also be adapted to multi-cell stacks as in pouch embodiments 1 and 2.

The outer surfaces of the positive and negative current collectors can be covered in a conductive grease and contacted with metal foils or metal plates acting as terminals to an external circuit. External pressure can optionally be applied to the entire stack to improve electrical contact at all of the interfaces.

TABLE 2

Comparison of bipolar pouch and commercial supercapacitor

|  | Bipolar Pouch Prototype | Commercial Supercapacitor |
| --- | --- | --- |
| Electrolyte | Aqueous (2.5 V) | Organic (2.7 V) |
| Dimensions | H: 2.5 mm; W/L: 40 mm | H: 40 mm; OD: 18 mm |
| Mass | 6 g | 13 g |
| Volume | 4 cm$^3$ | 10 cm$^3$ |
| Energy | 48 mWh | 51 mWh |
| Specific Energy | 8 Wh/kg (12 Wh/L) | 3.9 Wh/kg (5.1 Wh/L) |
| Specific Power | 1 kW/kg (1.5 kW/L) | 3 kW/kg (4 kW/L) |
| Temperature | −5° C. to 55° C. | −40° C. to 65° C. |

5. Fifth Example: Aqueous Bromide Redox-ECs with a Zinc Metal Anode

Figure 31:
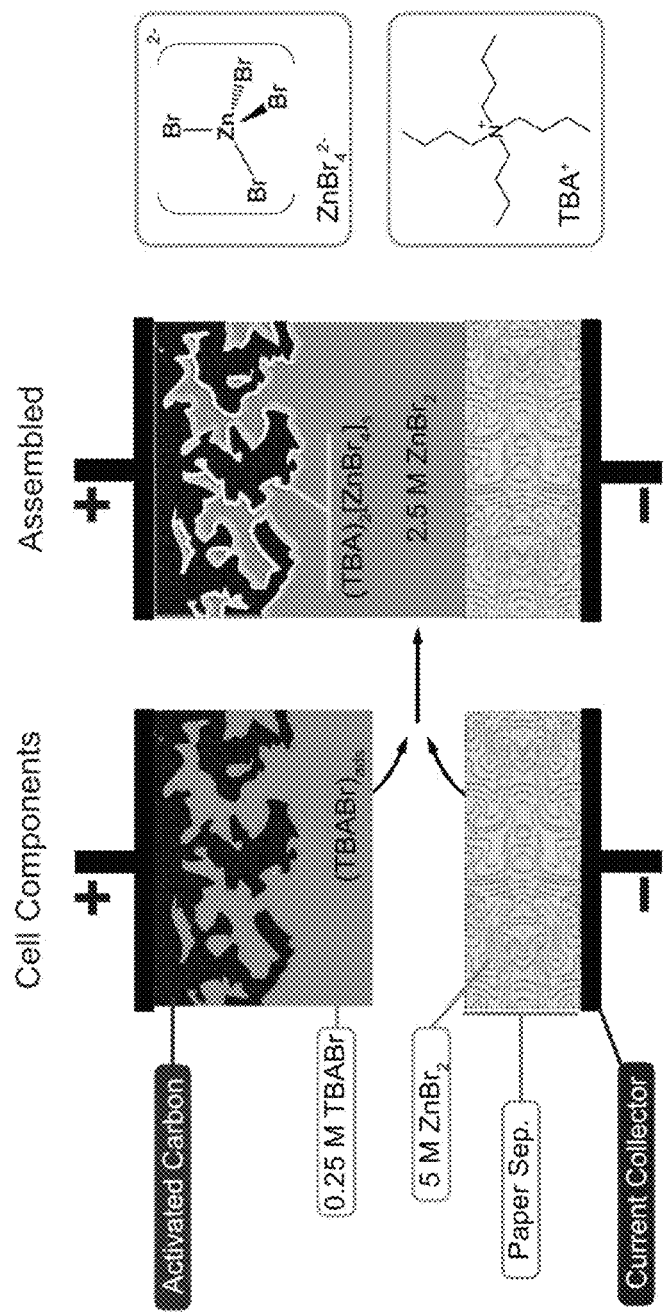
FIG. 31 illustrates zinc bromine redox-EC cell construction. The activated carbon is pre-soaked in a TBABr solution to pre-adsorb complexing agent at the surface. Then the electrode is contacted with a zinc bromide electrolyte and assembled into a cell with a paper separator.

The TBABr complexing agent paired with activated carbon and the bromide/tribromide redox couple makes a very stable and energy-dense aqueous cathode that functions well with all viologens investigated thus far. To see if this cathode could be more broadly useful, the cathode was paired with a zinc metal anode instead of an activated carbon/viologen anode. Zinc is an ideal anode because it operates in the same mildly acidic pH range, is low cost, has an extremely cathodic standard reduction potential (−0.76 V vs. SHE), and possesses a very high overpotential for hydrogen gas evolution. Although zinc bromine flow batteries often use quaternary ammonium complexing agents to sequester Br$_3$, the strong complexing agents like TBABr will not work with a traditional zinc bromine battery because the tetrabromozincate ion, $[ZnBr_4]^{2-}$, will form and precipitate as an insoluble complex with TBA$^+$ out of solution. To solve this issue, the inventors pre-adsorbed the TBABr complexing agent to the activated carbon by soaking the positive electrode in a solution of ~0.25 M TBABr (FIG. 31). The soaked electrode is then put into contact with a paper separator saturated with ≥5 M ZnBr$_2$. As the ZnBr$_2$ diffuses into the electrode, the (TBA)$_2$[ZnBr$_4$] solid complex forms and precipitates out of solution, adsorbing as thin film on the activated carbon surface. The full cell assembly consists of a 280 μm-thick Norit A Supra activated carbon positive electrode and a 180 μm-thick Whatman #1 paper separator between two current collectors. The typical final electrolyte is ~2.5 M ZnBr$_2$ with 1 wt. % PEG$_{200}$ (200 MW polyethylene glycol) additive to suppress zinc dendrite growth. In some cells an additional 0.5 M concentration of NaBr is added as a supporting electrolyte.

Figure 32:
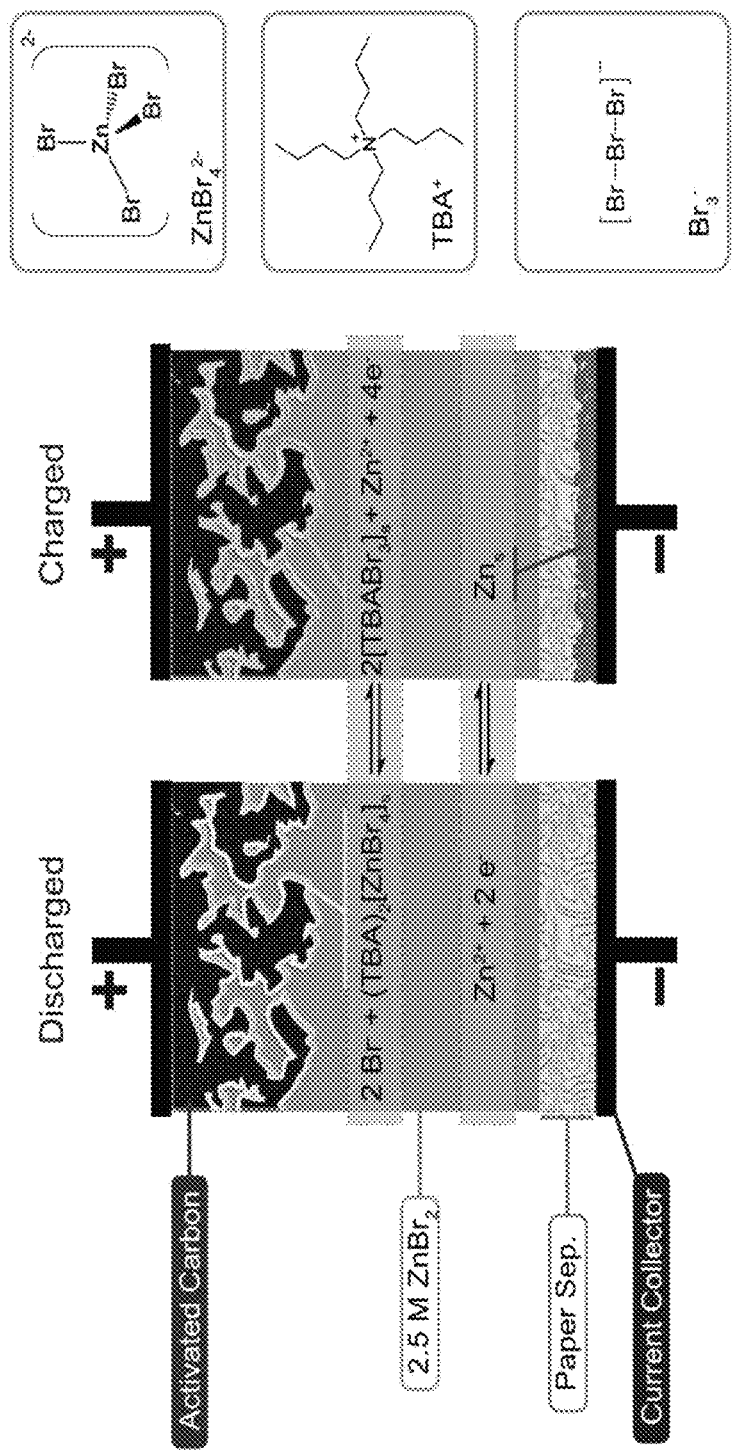
FIG. 32 illustrates the zinc bromine redox EC mechanism. With this chemistry, zinc is reversibly plated at the negative electrode and bromide is reversibly oxidized to tribromide and complexed into an insoluble solid with $TBA^+$ at the positive electrode.
Figure 33:
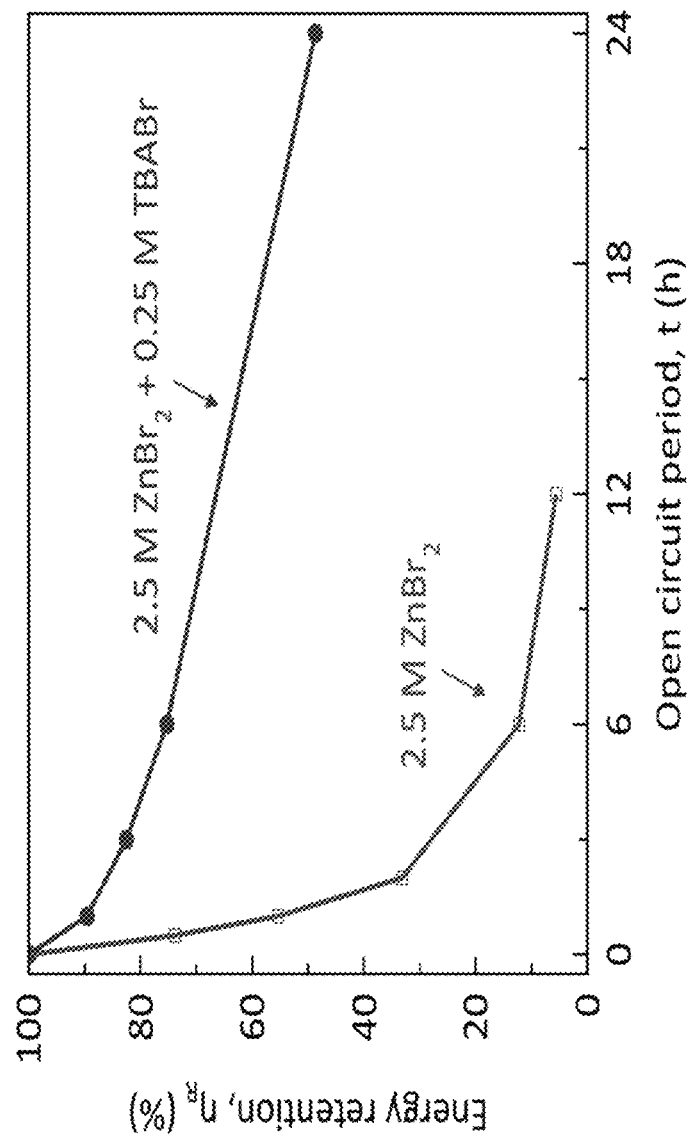
FIG. 33 illustrates self-discharge with and without TBABr. The fraction of the initial discharge energy retained after different periods at open circuit is much higher for cells with TBA complexing agent than for equivalent cells with no complexing agent.

While charging, bromide is oxidized to tribromide at the positive electrode, which complexes with TBA$^+$ and forms a solid at the electrode surface. This can also be seen as the tribromide anion replacing the tetrabromozincate anion in the solid complex. There is no need for an activated carbon negative electrode because zinc is plated directly from the electrolyte as a solid metal deposit on the negative current collector, filling the porous separator with zinc metal. Both of these processes are reversed upon discharge of the cell (FIG. 32). The solid complexation of tribromide by TBA$^+$ dramatically slows self-discharge compared to a ZnBr$_2$ cell without TBABr due to suppression of cross-diffusion (FIG. 33).

Figure 34:
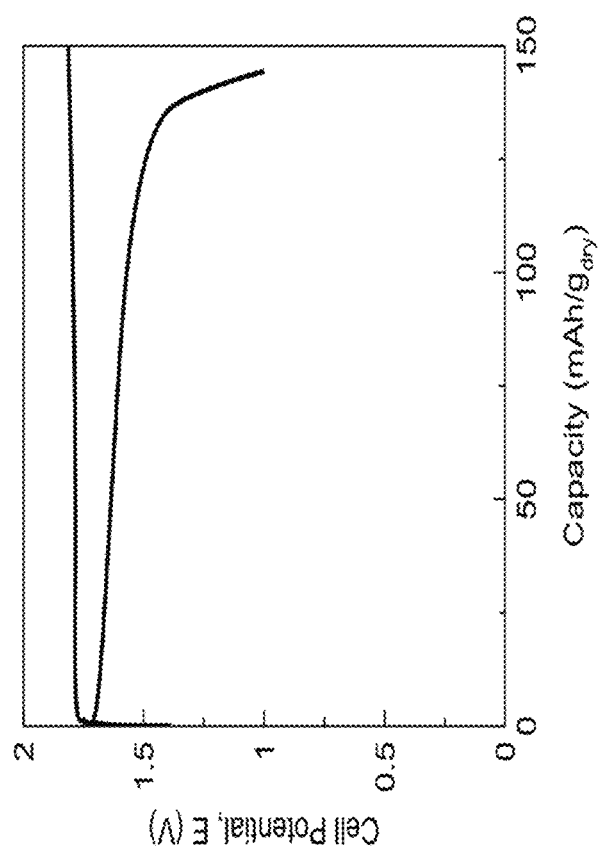
FIG. 34 illustrates typical galvanostatic potential profile for a $ZnBr_2$ cell. In this cell, the positive electrode is pre-soaked in 0.25 M TBABr and then both the separator and electrode are saturated with electrolyte containing 2.5 M $ZnBr_2$, 0.5 M NaBr, and 1 wt. % $PEG_{200}$. The cell charges to nearly 1.8 V at 1 A/g before cutoff at 150 mAh/g. The resulting charge/discharge plateaus are very flat, characteristic of the zinc bromine cell chemistry.
Figure 35:
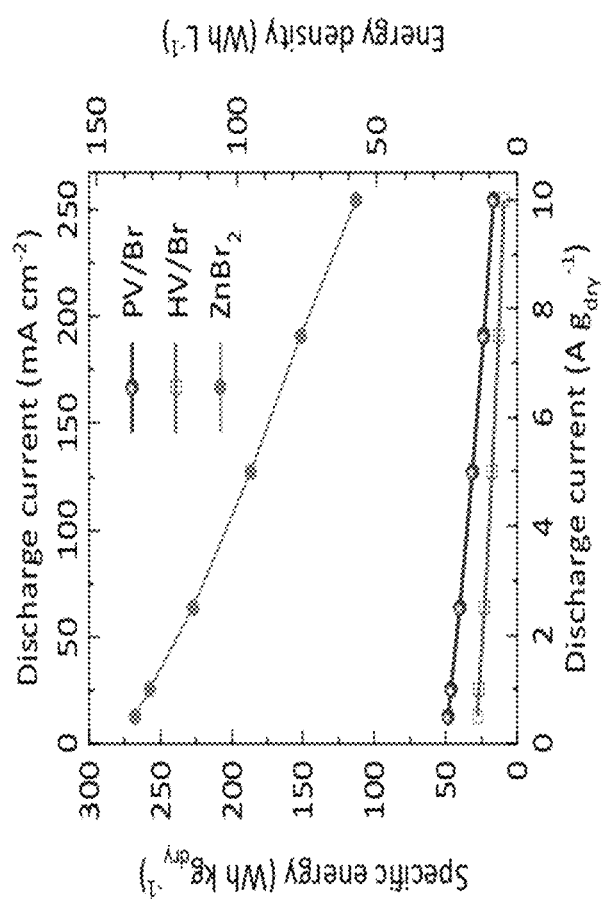
FIG. 35 shows discharge rate tests. Heptyl viologen, pentyl viologen, and zinc bromine cells are charged at 10 $mA/cm^2$ and discharged at different rates. Specific energy is normalized to the dry mass of the activated carbon electrode(s).
Figure 36:
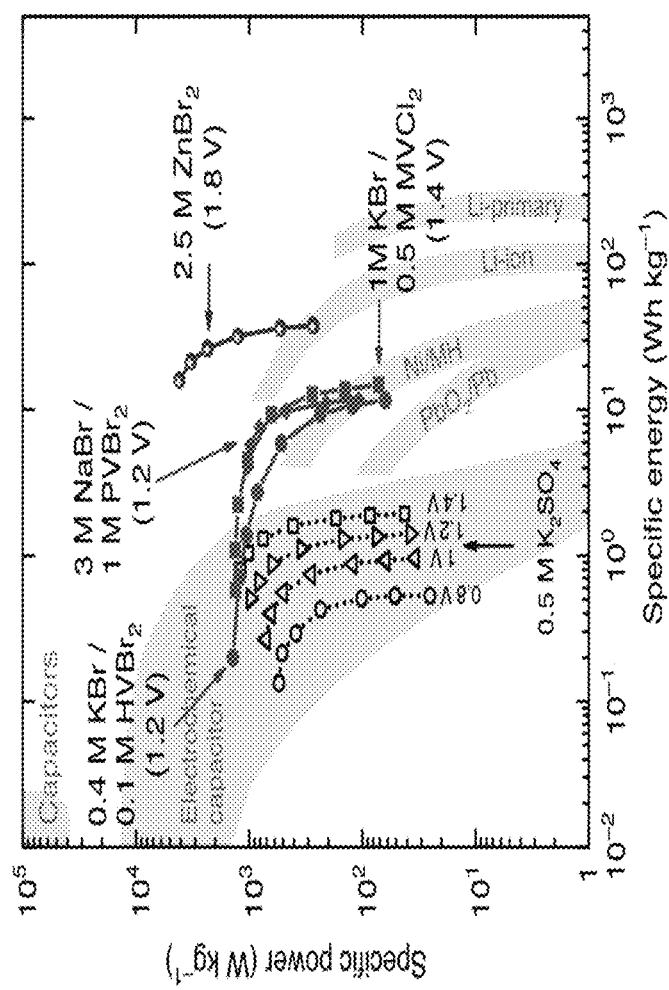
FIG. 36 shows a discharge Ragone Plot. Specific energy and power are normalized to the mass of the activated carbon electrodes and electrolyte for viologen cells and to the mass of the activated carbon electrode, separator, and electrolyte for the zinc bromine cell.

The zinc bromine cells constructed according to the methods described herein are typically charged by galvanostatic cycling at 1 A/g to a capacity of 100 or 150 mAh/g, based on the mass of the carbon electrode. They are discharged to a cell voltage of 1 V. The zinc bromide chemistry, compared to the viologen systems, is less redox-EC and more battery. A typical galvanostatic cycling with potential limitation (GCPL) profile, shown in FIG. 34, has exceptionally flat charge/discharge plateaus, a low iR drop, and coulombic efficiencies of 96-98%. The high 1.8 V potential of this chemistry is excellent for aqueous electrolytes and ~50% higher than that of the viologen systems. Due to the large capacity and high operating potential, the system exhibits excellent specific power and specific energy. To measure energy-power performance, a series of discharge rate tests was performed at discharge currents ranging from 1 A/g$_{dry}$ to 20 A/g$_{dry}$ (FIG. 35). The zinc bromine cells have only one electrode, so a discharge current of 20 A/g$_{dry}$, for example, is plotted as 10 A/g$_{dry}$ for comparison with viologen cells that contain two electrodes, since the areal current density is equivalent. The same data were also normalized to the mass of the wet cell stack including electrode, electrolyte, and separator and compared to that of viologen cells in FIG. 36. Although the ZnBr$_2$ devices cannot be charged as quickly as viologen redox-ECs, the maximum discharge energy and discharge power are significantly higher (40 Wh/kg$_{wet}$ and 4 kW/kg$_{wet}$, respectively).

Figure 37:
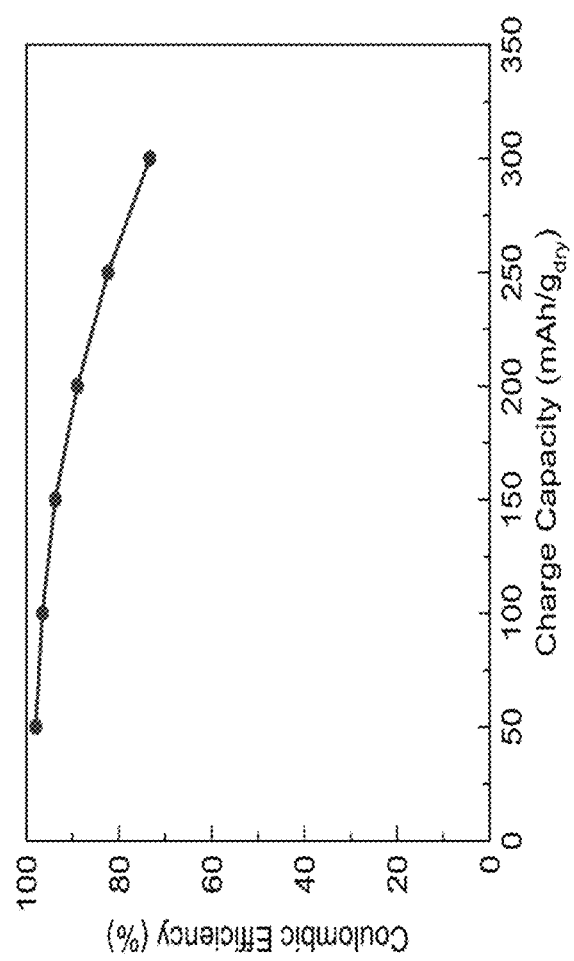
FIG. 37 plots coulombic efficiency versus charging capacity. For a cell with a 0.25 M TBABr pre-soaked electrode and a 2.5 M $ZnBr_2$ (with 1 wt. % $PEG_{200}$) electrolyte cycled at 0.5 A/g, Coulombic efficiency decreases substantially when the cell is overcharged, due to a finite quantity of complexing agent.
Figure 38:
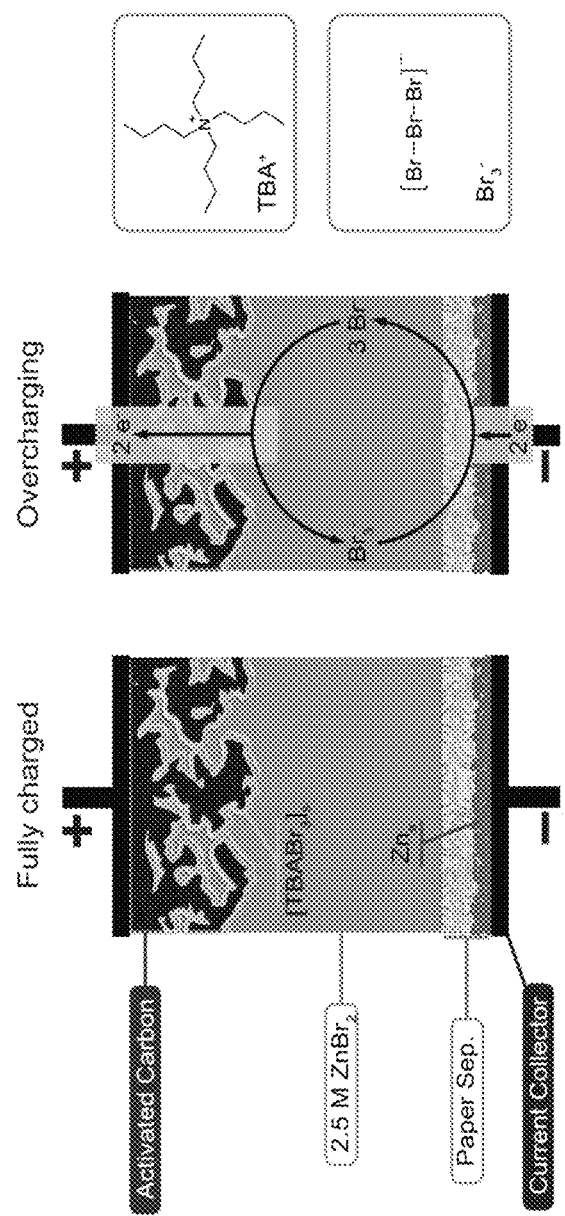
FIG. 38 shows overcharging $ZnBr_2$ Cells. Overcharging the $ZnBr_2$ chemistry causes a bromide/tribromide redox shuttle to develop, which creates a temporary internal short circuit to prevent overvoltage and protect the electrodes and electrolyte from degradation.

The ZnBr$_2$ cells have finite complexing agent, so when they are overcharged and all of the TBA$^+$ is utilized in TBABr$_3$ solid complexation, additional Br$_3^-$ can escape the positive electrode uncomplexed and diffuse across the cell where it is reduced back to Br, causing Coulombic efficiency to decrease as charging capacity increases (FIG. 37). Fortunately, this process is non-destructive. In fact, the development of this redox-shuttle is useful for when multiple cells are connected in series. If one cell in a series stack becomes overcharged, it will enter a condition where the Br$^-$/Br$_3^-$ redox shuttle develops and forms a temporary internal short circuit until the other cells in the stack reach the same fully charged state (FIG. 38).

Figure 39A:
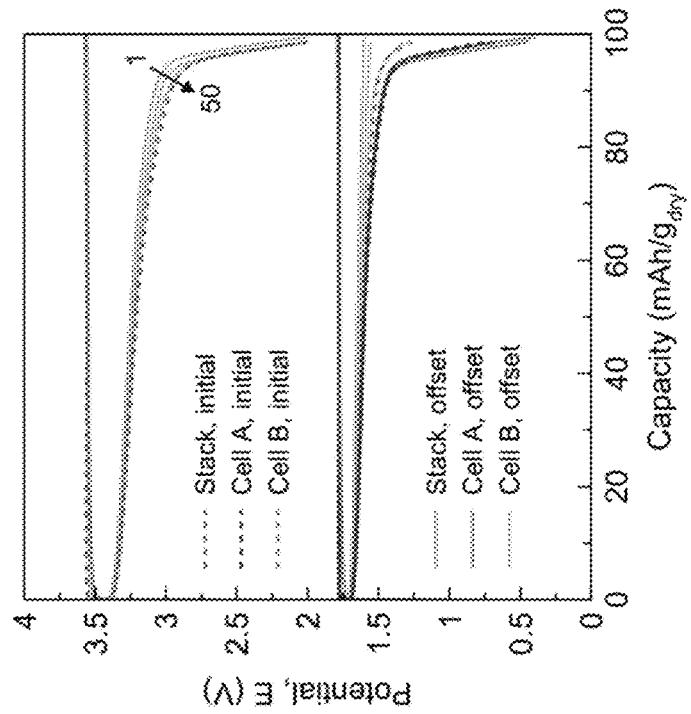
FIGS. 39(a)-39(b) shows self-balancing of series-connected $ZnBr_2$ Cells. Two cells, A and B, connected in series are cycled and the stack potential is measured between the counter electrode (CE) and working electrode (WE). The reference electrode (Ref) placed at the Cell A/Cell B junction enables the individual cell potentials to be measured as well. (left) A typical galvanostatic charge/discharge profile is shown for Cell A, Cell B, and the series AB stack for the $100^{th}$ cycle. (right) Cycles 1, 25 and 50 after the cells are intentionally offset (Cell A initially fully discharged and Cell B pre-charged to 50 mAh/g) so that Cell B is overcharging on each subsequent cycle show the profiles re-converge due to self-balancing in the cell stack.
Figure 39B:
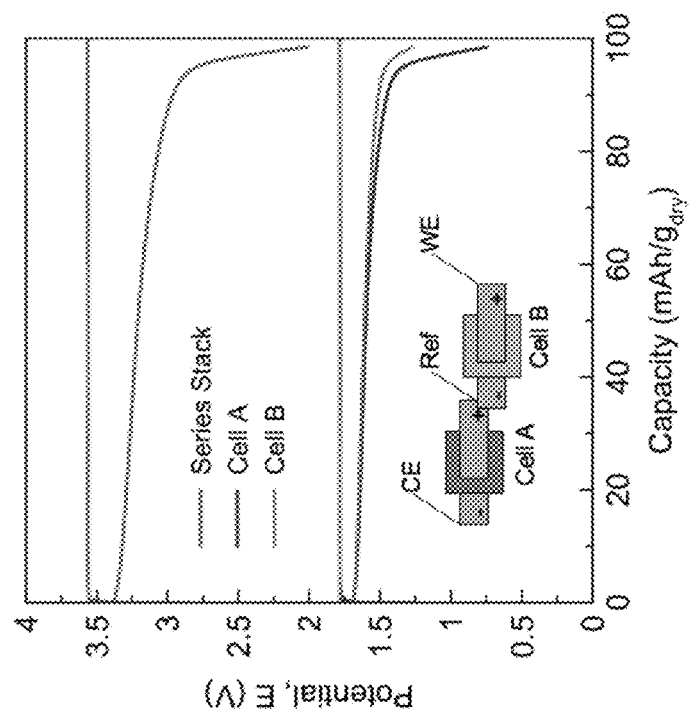

Therefore, the chemistry has a built-in mechanism for self-balancing that does not require water splitting (gassing) that would typically be used for a lead-acid battery, or a battery management system (BMS) that would typically be used for lithium-ion packs. To show experimentally that series-connected cells can stay balanced, two individual cells were connected and cycled together at 1 A/g to 100 mAh/g, as shown in FIGS. 39(a)-39(b). The cells stayed balanced over 100 cycles, with each cell completing the faradaic plateau at the end of every discharge. The cycling test was then repeated with the cells intentionally offset (Cell A initially fully discharged and Cell B pre-charged to 50 mAh/g) so that Cell B was overcharged on each subsequent cycle. Over the course of 50 cycles, the cells re-balanced, the potential profiles returned to their initial equilibrium state, and cycling continued normally.

Figure 40:
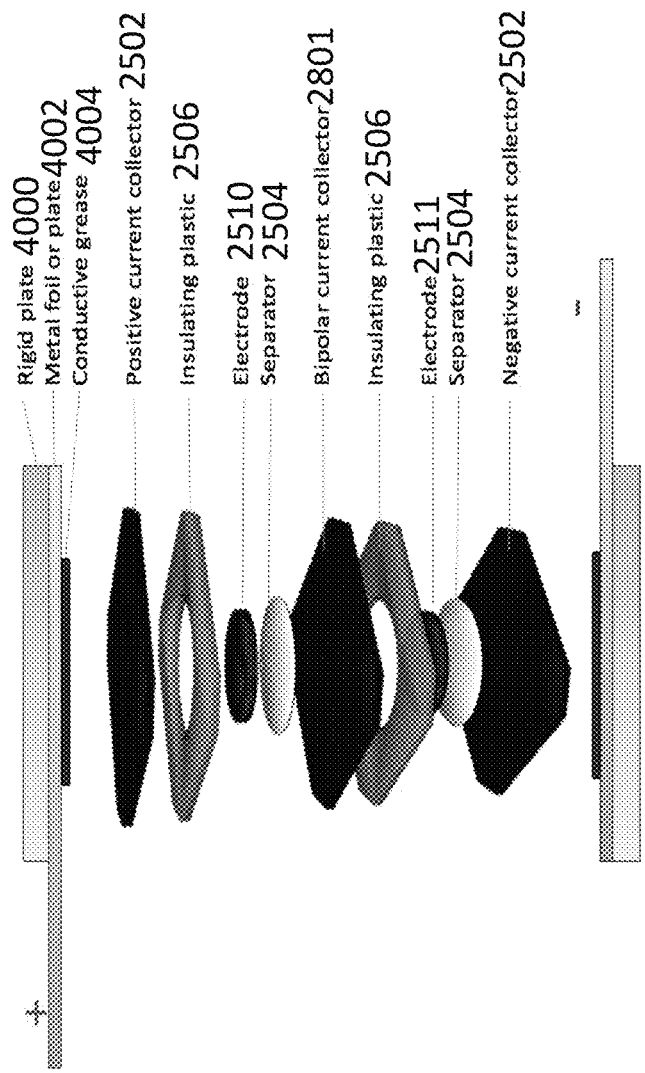
FIG. 40 is a schematic of a bipolar stack of $ZnBr_2$ pouch cells. Exploded view of the components used to construct a bipolar cell stack in a CB-PE composite pouch format. The insulating plastic (polyethylene) and the CB-PE current collectors (carbon black/polyethylene composite) are joined after assembly by heat sealing the cells' edges. Although not diagrammed, the electrodes are pre-soaked in 0.25 M TBABr and separators and electrodes are saturated with electrolyte containing 2.5 M $ZnBr_2$ and 1 wt. % $PEG_{200}$. External pressure is applied to the entire assembly by binder clips or similar compressive springs.
Figure 41:
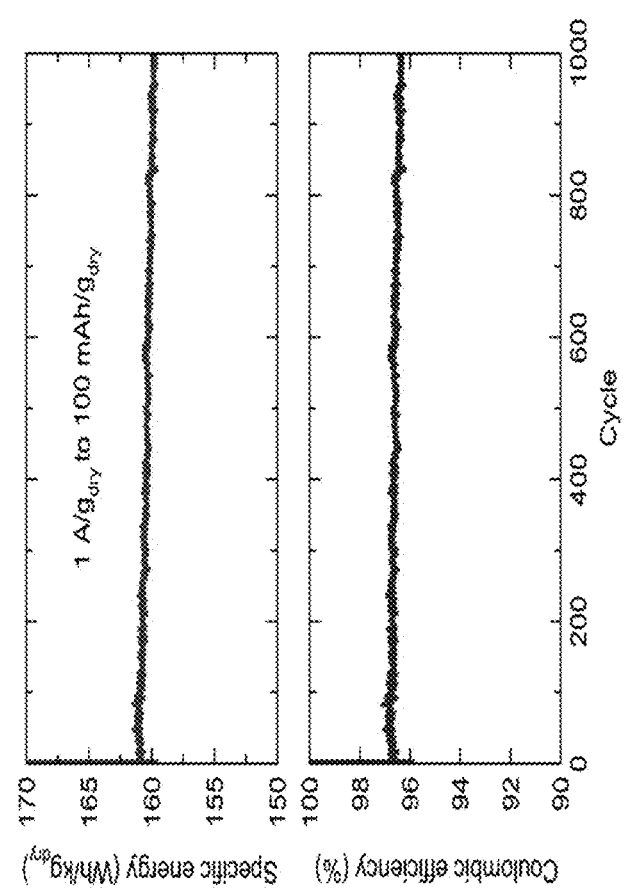
FIG. 41 shows cycling stability of the bipolar stack. When charged to 100 mAh/g, the stack delivers a specific energy of 160 Wh/kg, normalized to the mass of the carbon electrodes, and a Coulombic efficiency of 96.5%. After 1000 cycles, the stack retains 99% of its initial energy.

A bipolar pouch comprised of two cells was next constructed using zinc bromine chemistry to investigate cycling stability in a system more complex than individual cells. The exploded view of the cell components before heat-sealing and compression is shown in FIG. 40. FIG. 40 illustrates the device comprises rigid plate 4000, metal foil or plate 4002, conductive grease 4004, positive and negative current collectors 2502, insulating plastic 2506, electrodes 2510, 2511, separators 2504, and bipolar current collector 2801. The positive (+) and negative (−) terminals are also shown. After assembly, the stack was cycled at 1 A/g to a capacity of 100 mAh/g. The system showed excellent stability, with approximately 99% capacity retention over 1000 cycles (FIG. 41).

Figure 42:
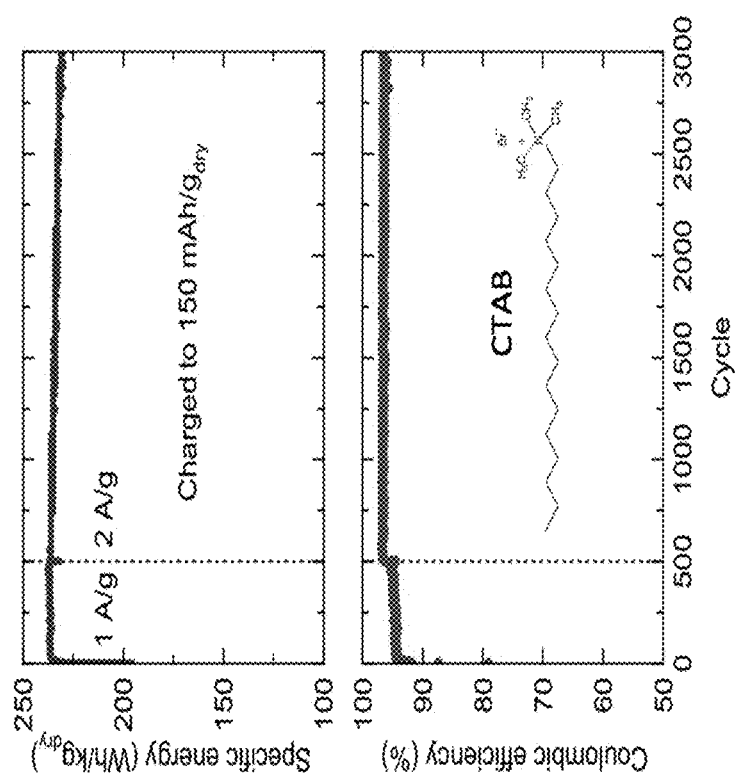
FIG. 42 shows cycling stability of the CTAB/$ZnBr_2$ cell. A cell with a 0.25 M CTAB pre-soaked electrode and a 2.5 M $ZnBr_2$ (with 1 wt. % $PEG_{200}$) electrolyte shows stable cycling at different operating conditions and high Coulombic efficiency. Specific energy is normalized to the dry mass of the activated carbon electrode.

To demonstrate that this concept can function with other bromine complexing agents, another CB-PE pouch cell was built with cetyltrimethylammonium bromide (CTAB) instead of TBABr. The cell was charged to 150 mAh/g at different rates and only 3% capacity fade was observed over more than 3000 cycles (FIG. 42).

6. Process Steps

Figure 43:
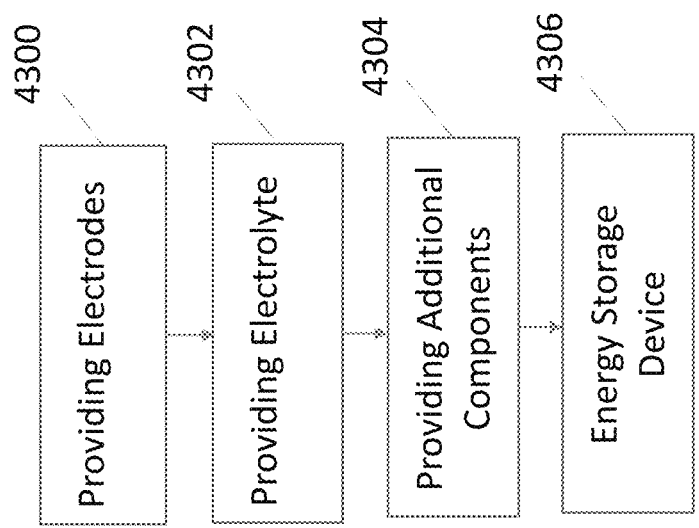
FIG. 43 is a flowchart illustrating a method fabricating an energy storage device.
Figure 44A:
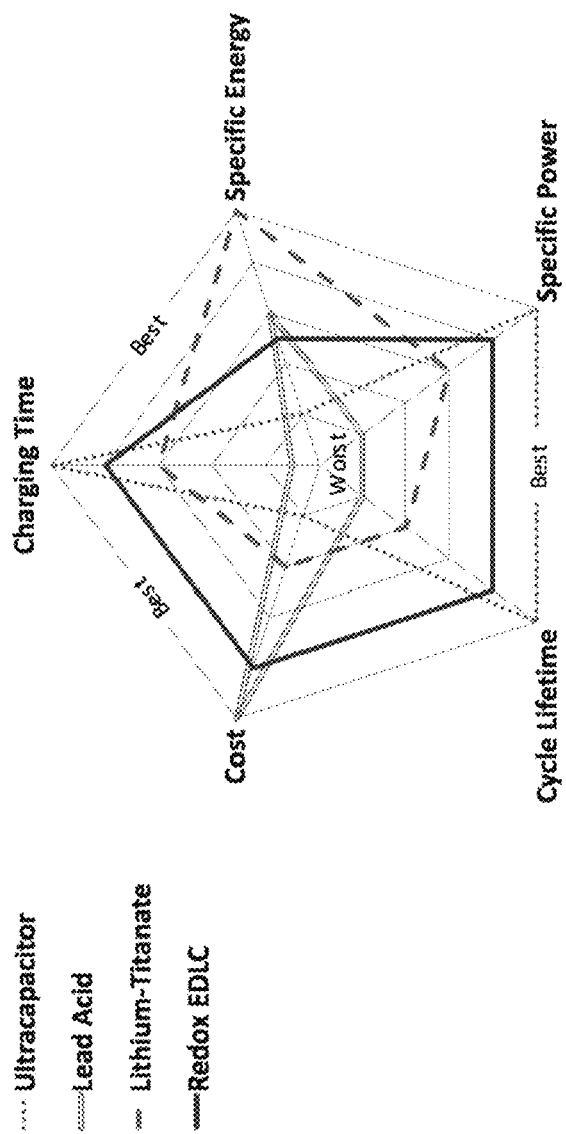
FIGS. 44(a)-44(b) illustrate hybrid EDLC technology according to one or more embodiments of the present invention combines performance advantages of batteries and capacitors.
Figure 44B:
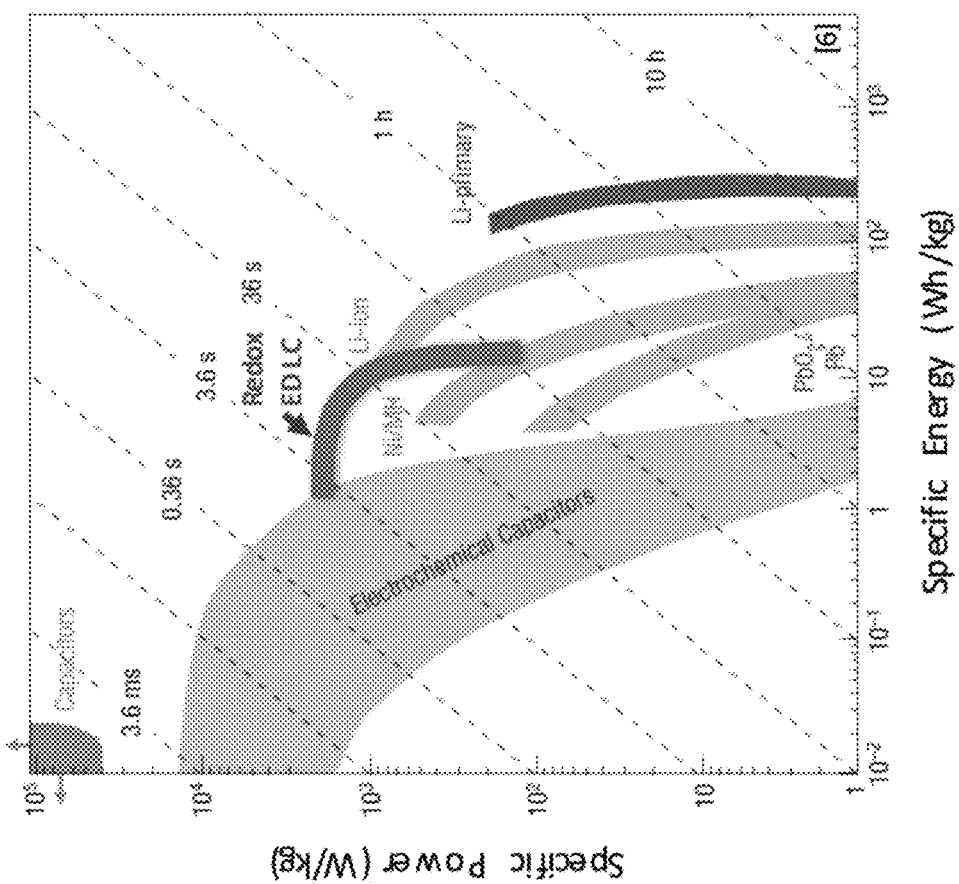

FIG. 43 is a flowchart illustrating a method of fabricating an energy storage device such as an electrochemical capacitor, supercapacitor, or EDLC, or a supercapacitor/battery hybrid.

Block 4300 represents providing or fabricating a first electrode 12 and a second electrode 14 (e.g., an anode and a cathode). In one or more examples, the cathode comprises carbon. In one or more further examples, the cathode comprises carbon and the anode comprises carbon.

In one or more embodiments, the step comprises providing a pouch 2500 having a first wall 2512 and a second wall 2514, the first wall and the second wall each including a current collector comprising a carbon-polymer composite 2502. The electrodes 2510, 2511, electrolyte 2508 and separator 2504 are disposed inside the pouch 2500.

Block 4302 represents providing an electrolyte 16 between and in contact with the electrodes 12, 14.

In one or more embodiments, the electrolyte comprises an integral active component for storing a charge.

In one embodiment, the electrolyte includes a first redox couple 18 comprising a halogen or halide (e.g., bromine, bromide, iodine, iodide, bromine moiety, iodine moiety) and a second redox couple 20 comprising a viologen. In one or more examples, the halogen is provided in a compound, e.g., NaBr or KBr in cases where the halogen is bromine.

In yet a further embodiment, the first redox couple comprises bromine (or bromine moiety) and the electrolyte comprises a complexing agent, such as a viologen or a tetraalkylammonium, tetraalkylammonium compound or moiety (e.g., but not limited to, tetrabutylammonium bromide in cases where the halogen in the first redox couple is bromine, or tetrabutylammonium triiodide or tetrabutylammonium tribromide in the cases where the halide is iodide) that forms a complex with the halogen (e.g., bromine, bromine moiety, iodine, iodine moiety) in the catholyte. In one example, the tetrabutylammonium bromide combines with the bromine or bromine moeity in the catholyte so as to form a [TBA$^+$.Br$_3^-$] solid complex retained in the pores of the porous carbon material in the cathode. In another embodiment wherein the complexing agent comprises a viologen, the viologen forms a complex with the bromine or bromine moiety in the catholyte. In one example, the electrolyte comprises 10 mol % of TBABr to the molar concentration of EVBr$_2$.

Examples of the viologens used herein include a viologen having the structure:

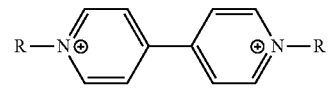

wherein R is an alkyl.

In one or more examples wherein the anolyte and/or the catholyte comprise viologen or viologen moiety, the viologen is at least one compound selected from ethyl viologen, butyl viologen, pentyl viologen, hexyl viologen, and other viologens comprising an alkyl having at least four carbon atoms.

In yet a further embodiment, the electrolyte includes a zinc moiety such as zinc halide (e.g., ZnBr$_2$) and tetraalkylammonium complexing agent (including, but not limited to tetrabutylammonium bromide (TBABr) or cetyltrimethylammonium bromide (CTAB)) is pre-adsorbed/pre-soaked on the cathode. In one example with the electrolyte comprising zinc halide, the electrolyte does not comprise a viologen.

In one or more zinc bromine system embodiments, the TBABr or CTAB pre-adsorption solution has a TBABr or CTAB concentration in a range of 10 mM to 1 M, the electrolyte comprises a ZnBr$_2$ concentration in a range of 1 M to 9 M and comprises an amount of PEG200 additive in a range of 1000 ppm to 100,000 ppm (0.1 wt. % to 10 wt. %), although other additives may also be used. In one or more further zinc bromine embodiments the electrolyte may further comprises an NaBr supporting electrolyte wherein the NaBr concentration is in a range of 0 M to 3 M. Other salts could also work (KBr, etc.). The supporting electrolyte may provides extra conductivity and additional bromide source.

Block 4304 represents providing additional EDLC or supercapacitor/battery hybrid components, if necessary. In one pouch embodiment, the step comprises sealing (e.g., heat sealing, in which case the carbon-polymer composite may comprise a thermoplastic) a plastic spacer 2506, the electrodes 2510 and 2511, the electrolyte 2508, 16, and a separator 2504 inside the pouch 2500. The seals 2518 are formed between the wall 2512 and the plastic spacer 2506, and the second wall 2514 and the opposite side of the plastic spacer 2506. The compartment bound above and below by the walls 2512 and 2514 and on the edges by the inside of the plastic spacer 2506 houses the two electrodes 2510 and 2511, the separator 2504, and the electrolyte 2508 permeating the electrodes and separator. Multiple such pouches can be stacked to get the desired stack voltage. In this embodiment, walls/current collectors 2512 and 2514 from adjacent cells can be in direct contact, as shown in FIG. 28*d*, or can be replaced by a single bipolar wall/current collector 2801 as shown in FIGS. 28*a* and 28*c*.

In one or more embodiments, the first wall 2512 and the second wall 2514 are flexible and have a thickness of 100 micrometers or less.

In one or more embodiments wherein the pouch is sealed using heat-sealing, the heat sealing comprises melting the walls 2512, 2514 and spacer 2506 together with no adhesive and with no additional sealing.

In one or more embodiments, the separator and the spacer are made from one component with a microporous polymer separator that has porosity collapse in the region of the heat-seal (see e.g., FIGS. 30(*e*) and 30(*f*)).

Block 4306 represents the end result, an energy storage device including, but not limited to, an EDLC, an EC, a battery, or supercapacitor/battery hybrid.

In one or more embodiments, during charging, the electrolyte evolves into a catholyte including the first redox couple and an anolyte including the second redox couple. When charged, the charge is stored in Faradaic reactions with the first and second redox couples in the electrolyte and in a double-layer capacitance of a porous carbon material that comprises at least one of the electrodes. In one or more embodiments, synergistic electrodes tune the pore size and volume of the carbon in the electrodes.

In an embodiment wherein the electrolyte comprises zinc halide:
   during charging, the zinc or zinc moiety from the zinc halide plates onto the anode and the halogen in the halide oxidizes so as to form a solid complex (e.g., (TBABr$_3^-$]) with the tetraalkylammonium on the cathode; and
   when charged, the charge is stored in Faradaic reactions with the electrolyte and in a double-layer capacitance of a porous carbon material in the cathode.

7. Advantages and Improvements

As described herein, viologen and bromide were identified as promising dual redox-active electrolytes for aqueous redox ECs. Bromide is a promising high-performance redox-active species for aqueous redox-enhanced electrochemical capacitors (redox ECs) due to the reversible redox reaction of Br$^-$/Br$_3^-$, excellent solubility and high redox potential.

With methyl viologen (MV) and bromide as the electrolytes, the system delivered a specific energy of ~50 Wh/kg$_{dry}$, but performance faded with prolonged cycling. Substituting heptyl viologen (HV) for MV dramatically improved cycling stability and slowed the self-discharge rate without the use of an ion-selective membrane separator. Improved performance of HV/Br over MV/Br was attributed to the strong adsorption of the charged HV$^+$. onto the activated carbon electrode. However, the specific energy of HV/Br system was ~20% lower than MV/Br system due to the low solubility of HV (<0.2 M). The critical challenge was to increase the solubility of a redox active viologen and still maintain stable cycling and slow self-discharge through strong adsorption. Since the development of promising HV/Br system, the present disclosure has investigated the viologen/bromide system in detail to understand the underlying mechanism, and to further improve the system.

The advantages of bromine as a catholyte are offset by the corrosive and volatile Br$_2$/Br$_3^-$ generated and its crossover through a separator. Asymmetric quaternary ammonium salts are conventionally used in flow batteries to complex Br$_2$/Br$_3^-$ as a mobile, oily-liquid phase and reduce the reactivity and vapor pressure. As demonstrated herein, this practice is not effective for static redox ECs. Instead, the present disclosure proposes stable bromine charge storage using tetrabutylammonium bromide as a complexing agent. In contrast to liquid complexation, this cation induces the reversible phase transition of soluble Br$_3^-$ into an insoluble solid complex and physically confines it in the pores of carbon electrodes upon charging. This mechanism suppresses unwanted chemical reactivity and cross-diffusion, leading to better stability and slower self-discharge for bromide-based aqueous redox ECs—without the use of an expensive ion-selective membrane separator. Based on this new mechanistic insight on the utilization of solid-state bromine storage in redox ECs, the present disclosure developed a dual-redox EC consisting of a bromide catholyte and a viologen anolyte with the addition of tetrabutylammonium bromide. For example, in comparison to aqueous and organic electric double-layer capacitors, the system using ethyl viologen and tetrabutylammonium bromide enhances energy by a factor of ca. 11 and 3.5, respectively, with a specific energy of ~64 W·h/kg at 1 A/g, a maximum power density >3 kW/kg, and cycling stability over 7000 cycles.

Furthermore, example systems disclosed herein are simple to fabricate in ambient conditions, use aqueous electrolyte, which is in principle safer, and provide further potential for higher power density due to the lower ionic resistance.

Conventional supercapacitors deliver high power for short periods of time, while conventional batteries deliver low power for long periods of time. Designing to these extremes requires tradeoffs on safety, lifetime, and cost. Embodiments of the EDLCs presented herein, on the other hand, integrate battery level energy density with capacitor level durability and power density into one safe, low cost device. Applications include using embodiments of the EDLCs described herein in an electrical grid or microgrid (e.g., with renewables), transportation (electric buses, engine start-stop, regenerative braking), and for industrial applications (energy recovery, heavy equipment, and fork lifts). Examples of the EDLC technology presented herein are well positioned to compete with advanced lead acid batteries by delivering higher power and longer life time at lower cost (see FIGS. 32(*a*) and 32(*b*)).

TABLE 3

| | Redox EDLC (Demonstrated) | Redox EDLC (Proposed) | Lithium-Titanate | Ultracapacitor | Lead Acid |
|---|---|---|---|---|---|
| Cycle lifetime | >20,000 | 100,000 | 6,000 | 1,000,000 | 1,000 |
| Charging time | 2 min | 1 min | 10 min | 10 sec | 8 h |
| Specific power | 1.5 kW/kg | 4 kW/kg | 3 kW/kg | 10 kW/kg | 0.2 kW/kg |
| Specific energy | 12 Wh/kg | 17.5 Wh/kg | 30-80 Wh/kg | 6 Wh/kg | 18 Wh/kg |
| Cost | | <$500/kWh | $1500/kWh | $2000/kWh | $200/kWh |

Comparison of redox EDLC embodiments and other technologies

8. Supplementary Information a. Methods and Materials Used for the Third Example (TBABr Complexing Agent with Ethyl Viologen Bromide Dual Redox Active Electrolyte)

Chemicals—

All reagents and starting materials were obtained commercially and used as received without any further purification:

Sodium bromide (NaBr), sodium sulfate ($Na_2SO_4$), tetrabutylammonium bromide (TBABr), 1-ethyl-1-methylpyrrolidinium bromide (methyl ethyl pyrrolidinium bromide; MEPBr), and ethyl viologen dibromide ($EVBr_2$) were purchased from Sigma-Aldrich. Hydrobromic acid (HBr) was purchased from Acros Organics, tetrabutylammonium tribromide was purchased from Alfa Aesar, sodium bromate ($NaBrO_3$) was purchased from J. T. Baker Chemical Co., sodium hydroxide (NaOH) was purchased from Fisher Chemical, and potassium bromide (KBr) was purchased from EMD Chemicals Inc. Water was from a Milli-Q Simplicity™ 185 system with resistivity ≥18.2 MΩ·cm (if not specified, all solutions in the SI and text refer to aqueous solutions).

Carbon Electrodes—

Activated carbon was prepared by $CO_2$ activation of high-purity carbon fibers (Donacarbo S-241, Osaka Gas Co., ~13 μm OD×130 μm long) in a tube furnace at 890° C. under flowing $CO_2$ (100 SCCM) for 22.5 h. Detailed characterization data, including specific surface area, elemental composition and pore size distribution were reported previously.[1]

For the preparation of electrodes, activated carbon, polytetrafluoroethylene (PTFE) binder (60 weight % aqueous dispersion from Sigma-Aldrich), and acetylene black conductive additive (Vulcan® XC72R) were mechanically mixed with a 90:5:5 mass ratio with isopropanol, and the resulting slurry was rolled into a single freestanding film with a PTFE rolling pin. This film was dried overnight at 160° C. in air, ground into a powder through a mesh sieve, and further dried under high vacuum at room temperature for two days. Freestanding electrode pellets were pressed from the powder in a 1-cm-diameter die (MTI Corporation) on a Carver hydraulic press under an applied uniaxial force of 2 tons, applied 3 times. Electrodes were 1 cm in diameter and 300±5 μm thick, for a total volume of 0.024 $cm^3$, and density of 0.42 g/$cm^3$.

Electrolytes—

The electrolytes were prepared by dissolving $EVBr_2$ and/or bromide salts in 18.2 MΩ water.

Tribromide ($Br_3^-$) Solution—

Bromine and $Br_3^-$ were generated using the following chemical reactions:[2]

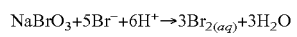

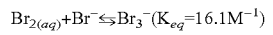

Cell Design and Assembly—

The construction of the redox-enhanced electrochemical capacitor (redox EC) cell including cell housing, current collectors, and the cell stack with two electrodes and a separator is described in detail in a previous report by the inventors.[3] Briefly, a two-electrode cell was built from a perfluoroalkoxy (PFA) Swagelok fitting with glassy-carbon-capped current collectors. For the preparation of each cell stack, two electrodes were soaked in 1.5 mL of test electrolyte, and vacuum and $N_2$ (150 psi) were alternately applied to infiltrate the hydrophobic carbon electrodes with aqueous electrolyte. Electrodes were then placed on either side of an electrolyte-wetted, 12-mm-diameter filter paper separator (Whatman™ #1). Thereafter, the cell stack was pressed between the two glassy-carbon-capped current collectors inside the cell body. For the three-electrode configuration tests, a T-shaped Swagelok PFA union was used with an Ag/AgCl reference electrode (Fisher Scientific™ Accumet™) placed with the tip at the edge of the separator with ~0.5 mL of excess test electrolyte added to submerge the reference electrode frit.

b. Electrochemical Studies

All electrochemical experiments (cyclic voltammetry, controlled potential electrolysis, and galvanostatic charge/discharge cycling test) were performed on a Bio-logic VMP3 potentiostat/galvanostat.

Analytical Voltammetry—

The cyclic voltammetry experiments were carried out in a conventional three electrode cell with either glassy carbon (CH Instruments, 3 mm diameter) or activated carbon pellet (identical to carbon electrode used in cells; pasted on a carbon cloth with conducting grease) working electrode, a Pt wire counter electrode, and an Ag/AgCl reference electrode (CH Instruments). The glassy carbon electrode was polished using polishing alumina (0.05 μm), and the Pt wire electrode was rinsed first with acetone followed by water and methanol, and then dried before each experiment. Test solutions were purged with $N_2$ for 10 mins prior to each measurement.

Controlled Potential Electrolysis—

Electrolysis experiments were performed in an open beaker-type cell with 6 mL of test electrolyte, i.e., 1 M KBr/0.2 M TBABr solution. Either carbon cloth, graphite rod or an activated carbon pellet (identical to carbon electrode used in cells; pasted on a carbon cloth with conducting grease)

served as working electrodes and a platinum wire served as the counter electrode. An Ag/AgCl electrode was used as the reference electrode.

Electrochemical Characterization of Redox ECs—

All galvanostatic charge/discharge (GCD) cycling tests were performed at a temperature of 25±1° C., or in a temperature chamber for temperature-dependent studies. The applied current for GCD cycling tests was normalized to the combined dry mass (activated carbon, carbon black, and PTFE binder) of both positive and negative electrodes. Potential limits were applied with the voltage range from 0 V (for discharging) to various $V_{max}$ values (for charging). Energy and power reported in the text indicate discharge energy ($E_{dis}$) and average discharge power ($P_{dis}$), which are normalized to the dry mass of both positive and negative electrodes to get specific energy (W·h/kg) and specific power (W/kg), respectively. The following equations are used for calculating device performance (I=applied current, t=time, and V=voltage):

| | |
|---|---|
| Charge capacity, $Q_{ch}$ (mA · h) | $Q_{ch} = I_{ch} \cdot t_{ch}$ |
| Discharge capacity, $Q_{dis}$ (mA · h) | $Q_{dis} = I_{dis} \cdot t_{dis}$ |
| Coulombic efficiency, $\eta_C$ | $\eta_C = Q_{dis}/Q_{ch}$ |
| Charge energy, $E_{ch}$ (W · h) | $E_{ch} = \int_0^{t_{ch}} I_{ch} \cdot V(t)\, dt$ |
| Discharge energy, $E_{dis}$ (W · h) | $E_{dis} = \int_0^{t_{dis}} I_{dis} \cdot V(t)\, dt$ |
| Average discharge power, $P_{dis}$ (W) | $P_{dis} = E_{dis}/t_{dis}$ |

The self-discharge rate was quantified based on the remaining discharge energy as a function of open circuit time, δ. An open circuit energy efficiency, $\eta_R$, is defined as the ratio of the energy retained after time δ at open circuit to the initial discharge energy and calculated by the following formula:

| | |
|---|---|
| Open circuit energy efficiency, $\eta_R$ | $\eta_R(\delta) = E_{dis}(\delta)/E_{dis}(0)$ |

Other Characterization Methods

The UV-vis spectra were acquired on an Agilent 8453 UV-vis spectrophotometer equipped with a cuvette holder. All spectra were recorded under ambient conditions with a 1 cm light-path. Contact angle measurements were taken on a DataPhysics OCA 15Pro system using an automatic elliptical fitting program, and the images were recorded with a charge-coupled device (CCD) camera horizontal to the drop to allow measurements of the test electrolytes' contact angles on the sample surface. Raman spectroscopy was performed on a Horiba JY Aramis Raman microscope equipped with a CCD detector thermoelectrically cooled to −70° C. Raman spectra were recorded with the incident laser of 0.86 mW, 600-µm hole, 400-µm slit width and a 600 lines/mm grating. The structure/morphology changes of carbon materials were observed through electron microscopes of a FEI Titan operating at 300 kV in scanning TEM mode, a FEI Quanta 600 SEM, and a FEI TECNAI™ T20 high-resolution transmission electron microscope (TEM) operating at 200 kV. The elemental composition of positive electrodes and carbon pellets was analyzed by energy-dispersive X-ray spectroscopy (EDX) at an accelerating voltage of 24.4 kV.

c. Normalized Performance Metrics

When the performance of devices including redox ECs is reported, normalizing to the dry mass of both positive and negative electrodes is the common practice in the literature. Therefore, the inventors evaluated cell performance normalized by dry mass in the present disclosure so that direct comparisons can be made. However, the inventors note that the redox couples in the electrolyte significantly contribute to the capacity through faradaic energy storage for the redox ECs. To clarify and address this discrepancy of the performance normalization, the inventors have included a table (Table S1) which normalizes energy, power, and capacity to both masses, i.e., performance metrics based on "wet" cell mass (electrodes plus electrolyte) and "dry" cell mass (electrodes only).

Performance Normalization—

Electrodes and electrolyte from a 1.2 M $EVBr_2$/0.12 M TBABr/2.88 M NaBr two-electrode cell massed before and after cycling weighed 90 mg. The cell performance was then normalized to the total masses of electrodes only (indicated as g), and electrodes plus electrolyte (indicated as $g_{wet}$) in Table S1.

TABLE S1

Performance metrics normalized to different cell components (cell was charged/discharged between 0 V and 1.35 V at 1 A/g. Energy, capacity, and power reported here are from the 20$^{th}$ charge/discharge cycle.)

| | Dry electrodes | Wet electrodes |
|---|---|---|
| Mass for normalization (mg) | 20 mg (Cathode: 10 mg; Anode: 10 mg) | 90 mg (Electrolyte: 70 mg; electrodes: 20 mg) |
| Specific energy (W · h/kg) | 63.6 W · h/kg | 14.1 W · h/kg$_{wet}$ |
| Specific capacity (mA · h/g) | 66.6 mA · h/g | 14.8 mA · h/g$_{wet}$ |
| Specific power (W/kg) | 970 W/kg | 216 W/kg$_{wet}$ | d. Further Experimental Details

Contact-Angle Measurements (Figure S1)—

Aqueous solutions of 1 M KBr, 1 M MEPBr, and 1 M TBABr were prepared, and an activated carbon pellet (identical to carbon electrode used in cells) was used as a test surface. A 2 µL liquid droplet of test electrolyte was gently placed on the surface with a syringe, and the needle was withdrawn immediately to minimize any inconsistency that might be caused by solution evaporation prior to image capture. The contact angle was determined by using an automatic elliptical fitting program.

Controlled Potential Electrolysis, Scanning Transmission Electron Microscopy (STEM), and Energy-Dispersive X-Ray Spectroscopy (EDX) (Table S2)—

To demonstrate the electrochemical generation of the [TBA$^+$.Br$_3^-$] solid complex, anodic oxidation of bromide was carried out with a carbon cloth as working electrode. To an open beaker-type cell was added 6 mL of 1 M KBr/0.2 M TBABr solution, and controlled potential electrolysis at 1.2 V (vs Ag/AgCl reference electrode; a Pt wire counter electrode) was performed until yellow solids were clearly visible on the working electrode. Following electrolysis, the working electrode was photographed and its image is displayed in FIG. 10b.

To investigate solid-state confinement of electrochemically generated [TBA$^+$.Br$_3^-$] solid complex in the pores of the high-surface-area carbon electrode, analysis of carbon surface/pores was conducted using STEM following electrolysis. For the electrolysis, a high-surface-area activated carbon pellet was pasted and pressed on a carbon cloth with conducting grease. The remaining area of the carbon cloth was masked with electrochemical tape to block its exposure to the electrolyte. As a control, an identical activated carbon pellet was separately prepared. Both pellets were immersed in the 1 M KBr/0.2 M TBABr solution, and vacuum/$N_2$ (150 psi) were alternately applied to infiltrate the hydrophobic carbons with aqueous electrolyte. Then, electrolysis was performed with the first pellet (electrolyzed C pellet) as the working electrode in an open beaker-type cell with 1 M KBr/0.2 M TBABr solution at set potential of 0.6 V (vs Ag/AgCl reference electrode; a Pt wire counter electrode). The potential increased incrementally to 1.2 V before the electrolysis was terminated after a charge of 10.4 C was passed. For the full duration of electrolysis, the control pellet (control C pellet) was immersed in a separate 1 M KBr/0.2 M TBABr solution.

Both carbon pellets were removed from the solutions and each surface was washed with water, soaked in 10 mL of water for 7 h, and dried in air at room temperature for 24 h. Samples for STEM analysis were prepared by sonicating (10 mins) small pieces of each pellet in isopropanol and dropcasting the dispersion onto lacey-carbon TEM grids. The samples were imaged by STEM with the signal being acquired using a high angle annular dark field detector (HAADF-STEM). In addition, elemental analysis by EDX of the electrolyzed C pellet and control C pellet were performed and results are summarized in Table S2.

TABLE S2

Elemental analysis by EDX of the electrolyzed C pellet and control C pellet (relative atomic ratio of C to Br present in the sample; calculation based on the atom %)

| Sample | C | Br |
|---|---|---|
| Electrolyzed C pellet | 28 | 72 |
| Control C pellet | 100 | 0 |

UV-Vis Measurements for Testing Complexation of Ethyl Viologen Dication ($EV^{2+}$) and $Br_3^-$ (FIG. 15)—

To generate spectra of uncomplexed $EV^{2+}$, 20 mM $EVBr_2$ solution was prepared in a 1.5 mL centrifuge tube, and the solution was agitated with a vortex mixer for 1 min followed by centrifugation for 5 min at 4,000 rpm (Eppendorf® MiniSpin Plus Centrifuge). Then, a 5 µL sample of the 20 mM $EVBr_2$ solution was diluted 400 times into 1.995 mL of water in a quartz cuvette. The capped cuvette was shaken to ensure a homogeneous analyte before UV-vis measurements.

To generate spectra of the $EV^{2+}$ after complexation with $Br_3^-$, 500 µL of 60 mM $EVBr_2$ solution was combined with equal volumes of 120 mM $Br_3^-$ solution and water. Then, EV remaining dissolved in the supernatant after the addition of $Br_3^-$ was processed with the same methods stated above before UV-vis measurements. Optical absorption data for both uncomplexed and complexed $EV^{2+}$ samples were normalized to the absorbance at the absorption maxima ($\lambda_{max}$=260 nm) for the uncomplexed $EV^{2+}$ sample.

UV-Vis Measurements for Testing Complexation of $EV^{2+}$ and $Br_3^-$ in the Presence of Methyl Ethyl Pyrrolidinium Bromide (MEPBr) and Tetrabutylammonium Bromide (TBABr) (FIG. 15)—

To generate spectra of the $EV^{2+}$ in the presence of $Br_3^-$ and MEPBr or TBABr, respectively, to test competitive $Br_3^-$ complexation between $EV^{2+}$ and these quaternary ammonium cations, 500 µL of 60 mM $EVBr_2$ solution was combined with equal volumes of 120 mM $Br_3^-$ solution and 120 mM quaternary ammonium bromide solution in a 1.5 mL centrifuge tube. Then, EV remaining dissolved in the supernatant was processed with the same methods stated above before UV-vis measurements. Each spectrum was normalized by the absorption maxima measured for uncomplexed $EV^{2+}$ samples (in a solution containing the corresponding concentrations of MEPBr and TBABr, respectively, but without $Br_3^-$).

Control/Comparison Devices (FIG. 16d)—

An aqueous EDLC cell (1 M $Na_2SO_4$ electrolyte) and commercial non-aqueous device (BCAP0001 P270 T01, Maxwell Technologies) were tested to provide reference performance data in comparison to the EV/TBA/Br dual-redox EC. The 1 M $Na_2SO_4$ cell was assembled with the same cell housing, current collectors, electrodes, and separator as the EV/TBA/Br cell. The commercial cell was tested with a specified 2.7 V of working potential range. To report specific energy and specific power of the Maxwell cell normalized to the dry mass of both positive and negative electrodes, the device was disassembled after GCD cycling tests. The extracted cell stack was placed in 20 mL aqueous NaOH solution to dissolve the aluminum foil current collectors and isolate the electrodes. Thereafter, the electrodes were soaked in ~20 mL of doubly distilled water and dried in an oven at 160° C. until the mass remained constant.

e. Supplementary Data

TABLE S3

Open circuit energy efficiency ($\eta_R$) for each asymmetric cell at 0° C., 25° C., and 40° C. (Self-discharge rates)

| Open circuit energy efficiency, $\eta_R$ (□ h) | 1.2M KBr cell | | | 1M KBr/0.2M MEPBr cell | | | 1M KBr/0.2M TBABr cell | | |
|---|---|---|---|---|---|---|---|---|---|
|  | 0° C. | 25° C. | 40° C. | 0° C. | 25° C. | 40° C. | 0° C. | 25° C. | 40° C. |
| $\eta_R$ (2 h) (%) | 43 | 40 | 8 | 63 | 66 | 44 | 80 | 79 | 70 |
| $\eta_R$ (6 h) (%) | 20 | 5 | 0 | 44 | 34 | 9 | 67 | 62 | 49 |
| $\eta_R$ (10 h) (%) | 10 | 1 | 0 | 32 | 14 | 2 | 59 | 50 | 37 |

TABLE S4

Elemental analysis by EDX of positive electrodes after cycling (relative atomic ratio of C to F; calculation based on the atom %)

| Cells | C | F |
|---|---|---|
| Pristine activated carbon electrode | 97 | 3 |
| Electrode after cycling in a KBr cell | 83 | 17 |
| Electrode after cycling in a KBr/MEPBr cell | 84 | 16 |
| Electrode after cycling in a KBr/TBABr cell | 98 | 2 |

REFERENCES

The following references are incorporated by reference herein:

(1) Béguin, F.; Presser, V.; Balducci, A.; Frackowiak, E. Adv. Mater. 2014, 26, 2219.

(2) Simon, P.; Gogotsi, Y. Nat. Mater. 2008, 7, 845.
(3) Burke, A. J. Power Sources 2000, 91, 37.
(4) Blomquist, N.; Wells, T.; Andres, B.; Backstrom, J.; Forsberg, S.; Olin, H. Sci. Rep. 2017, 7, 39836.
(5) Wang, Y.; Song, Y.; Xia, Y. Chem. Soc. Rev. 2016, 45, 5925.
(6) Fic, K.; Meller, M.; Menzel, J.; Frackowiak, E. Electrochim. Acta 2016, 206, 496.
(7) Gao, Q.; Demarconnay, L.; Raymundo-Pinero, E.; Beguin, F. Energy Environ. Sci. 2012, 5, 9611.
(8) Arbizzani, C.; Biso, M.; Cericola, D.; Lazzari, M.; Soavi, F.; Mastragostino, M. J. Power Sources 2008, 185, 1575.
(9) Augustyn, V.; Simon, P.; Dunn, B. Energy Environ. Sci. 2014, 7, 1597.
(10) Sheberla, D.; Bachman, J. C.; Elias, J. S.; Sun, C. J.; Shao-Horn, Y.; Dinca, M. Nat. Mater. 2016.
(11) Brezesinski, T.; Wang, J.; Tolbert, S. H.; Dunn, B. Nat. Mater. 2010, 9, 146.
(12) Lang, X.; Hirata, A.; Fujita, T.; Chen, M. Nat. Nanotechnol. 2011, 6, 232.
(13) Yan, J.; Wang, Q.; Wei, T.; Fan, Z. J. Adv. Energy Mater. 2014, 4, 1300816.
(14) Muller, G. A.; Cook, J. B.; Kim, H.-S.; Tolbert, S. H.; Dunn, B. Nano Lett. 2015, 15, 1911.
(15) Boota, M.; Chen, C.; Becuwe, M.; Miao, L.; Gogotsi, Y. Energy Environ. Sci. 2016, 9, 2586.
(16) Fic, K.; Meller, M.; Frackowiak, E. J. Electrochem. Soc. 2015, 162, A5140.
(17) Frackowiak, E.; Meller, M.; Menzel, J.; Gastol, D.; Fic, K. Faraday Discuss. 2014, 172, 179.
(18) Roldán, S.; Blanco, C.; Granda, M.; Menéndez, R.; Santamaria, R. Angew. Chem., Int. Ed. 2011, 50, 1699.
(19) Lee, J.; Kruner, B.; Tolosa, A.; Sathyamoorthi, S.; Kim, D.; Choudhury, S.; Seo, K.-H.; Presser, V. Energy Environ. Sci. 2016, 9, 3392.
(20) Senthilkumar, S. T.; Selvan, R. K.; Melo, J. S. J. Mater. Chem. A 2013, 1, 12386.
(21) Lee, J.; Choudhury, S.; Weingarth, D.; Kim, D.; Presser, V. ACS Appl. Mater. Interfaces 2016, 8, 23676.
(22) Wang, X.; Chandrabose, R. S.; Chun, S.-E.; Zhang, T.; Evanko, B.; Jian, Z.; Boettcher, S. W.; Stucky, G. D.; Ji, X. ACS Appl. Mater. Interfaces 2015, 7, 19978.
(23) Lee, J.; Tolosa, A.; Krüner, B.; Jäckel, N.; Fleischmann, S.; Zeiger, M.; Kim, D.; Presser, V. Sustainable Energy Fuels 2017, 1, 299.
(24) Chen, L.; Bai, H.; Huang, Z.; Li, L. Energy Environ. Sci. 2014, 7, 1750.
(25) Wang, B.; Maciá-Agulló, J. A.; Prendiville, D. G.; Zheng, X.; Liu, D.; Zhang, Y.; Boettcher, S. W.; Ji, X.; Stucky, G. D. J. Electrochem. Soc. 2014, 161, A1090.
(26) Chun, S.-E.; Evanko, B.; Wang, X.; Vonlanthen, D.; Ji, X.; Stucky, G. D.; Boettcher, S. W. Nat. Commun. 2015, 6, 7818.
(27) Senthilkumar, S. T.; Selvan, R. K.; Lee, Y. S.; Melo, J. S. J. Mater. Chem. A 2013, 1, 1086.
(28) Tang, X.; Lui, Y. H.; Chen, B.; Hu, S. J. Power Sources 2017, 352, 118.
(29) Li, Q.; Haque, M.; Kuzmenko, V.; Ramani, N.; Lundgren, P.; Smith, A. D.; Enoksson, P. J. Power Sources 2017, 348, 219.
(30) Zhao, Y.; Ding, Y.; Song, J.; Peng, L.; Goodenough, J. B.; Yu, G. Energy Environ. Sci. 2014, 7, 1990.
(31) Sankar, K. V.; Kalai Selvan, R. Carbon 2015, 90, 260.
(32) Biswas, S.; Senju, A.; Mohr, R.; Hodson, T.; Karthikeyan, N.; Knehr, K. W.; Hsieh, A. G.; Yang, X.; Koel, B. E.; Steingart, D. A. Energy Environ. Sci. 2017, 10, 114.
(33) Gerhardt, M. R.; Tong, L.; Gómez-Bombarelli, R.; Chen, Q.; Marshak, M. P.; Galvin, C. J.; Aspuru-Guzik, A.; Gordon, R. G.; Aziz, M. J. Adv. Energy Mater. 2017, 7, 1601488.
(34) Lancry, E.; Magnes, B.-Z.; Ben-David, I.; Freiberg, M. ECS Trans. 2013, 53, 107.
(35) Poon, G.; Parasuraman, A.; Lim, T. M.; Skyllas-Kazacos, M. Electrochim. Acta 2013, 107, 388.
(36) Evanko, B.; Yoo, S. J.; Chun, S.-E.; Wang, X.; Ji, X.; Boettcher, S. W.; Stucky, G. D. J. Am. Chem. Soc. 2016, 138, 9373.
(37) Hoshino, K.; Ando, M.; Oikawa, Y.; Okuma, M.; Murashiro, K. Sol. Energy Mater. Sol. Cells 2015, 137, 15.
(38) Fic, K.; Lota, G.; Frackowiak, E. Electrochim. Acta 2010, 55, 7484.
(39) Fic, K.; Lota, G.; Frackowiak, E. Electrochim. Acta 2012, 60, 206.
(40) Chen, X.; Rickard, M. A.; Hull, J. W.; Zheng, C.; Leugers, A.; Simoncic, P. Inorg. Chem. 2010, 49, 8684.
(41) Zambounis, J. S.; Kamitsos, E. I.; Patsis, A. P.; Papavassiliou, G. C. J. Raman Spectrosc. 1992, 23, 81.
(42) Klein, N. D.; Hurley, K. R.; Feng, Z. V.; Haynes, C. L. Anal. Chem. 2015, 87, 4356.
(43) Pennycook, S. J. In Characterization of Materials; John Wiley & Sons, Inc.: 2002.
(44) Genovese, M.; Jiang, J.; Lian, K.; Holm, N. J. Mater. Chem. A 2015, 3, 2903.
(45) Gaier, J. R.; Ditmars, N. F.; Dillon, A. R. Carbon 2005, 43, 189.
(46) Izumi, I.; Sato, J.; Iwashita, N.; Inagaki, M. Synth. Met. 1995, 75, 75.
(47) Sathyamoorthi, S.; Kanagaraj, M.; Kathiresan, M.; Suryanarayanan, V.; Velayutham, D. J. Mater. Chem. A 2016, 4, 4562.
(48) Chun, S.-E.; Evanko, B.; Wang, X.; Vonlanthen, D.; Ji, X.; Stucky, G. D.; Boettcher, S. W. Nat. Commun. 2015, 6, 7818.
(49) Wang, T. X.; Kelley, M. D.; Cooper, J. N.; Beckwith, R. C.; Margerum, D. W. Inorg. Chem. 1994, 33, 5872.
(50) Evanko, B.; Yoo, S. J.; Chun, S.-E.; Wang, X.; Ji, X.; Boettcher, S. W.; Stucky, G. D. J. Am. Chem. Soc. 2016, 138, 9373.
(51) S.-E. Chun, B. Evanko, X. Wang, D. Vonlanthen, X. Ji, G. D. Stucky and S. W. Boettcher, Nat. Commun., 2015, 6, 7818.
(52) B. Evanko, S. J. Yoo, S.-E. Chun, X. Wang, X. Ji, S. W. Boettcher and G. D. Stucky, J. Am. Chem. Soc., 2016, 138, 9373-9376.
(53) Wang, T. X.; Kelley, M. D.; Cooper, J. N.; Beckwith, R. C.; Margerum, D. W. Inorg. Chem. 1994, 33, 5872.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An energy storage device, comprising:
an electrical double layer capacitor (EDLC) including:
one or more cells, each cell including:
a pouch having a first wall and a second wall, the first wall and the second wall each comprising a current collector including a carbon-polymer composite; a plastic spacer, a first electrode, a second electrode , an electrolyte, and a separator inside the pouch; and
a seal between the first wall and the second wall so that the plastic spacer, the first electrode, the second electrode, the electrolyte, and the separator are sealed inside the pouch; and wherein:
the first electrode and the second electrode are in contact with the electrolyte,
the electrolyte includes a first redox couple comprising bromine or a bromine moiety and a second redox couple comprising a viologen;
during charging, the electrolyte evolves into a catholyte including the first redox couple and an anolyte including the second redox couple; and
when charged, the charge is stored in Faradaic reactions with the first redox couple and the second redox couple in the electrolyte and in a double-layer capacitance of athc porous carbon material that comprises at least one of the first electrodecicctrodcs or the second electrode.

2. The device of claim 1, wherein the viologen has the structure:

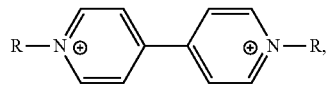

and
R is an alkyl.

3. The device of claim 2, wherein the viologen comprises at least one compound selected from ethyl viologen, butyl viologen, and pentyl viologen.

4. The device of claim 1, wherein the catholyte further comprises a viologen.

5. The device of claim 1, wherein the electrolyte further comprises a complexing agent comprising a viologen that forms a complex with the bromine moiety in the catholyte.

6. The device of claim 5, wherein the viologen is at least one compound selected from hexyl viologen and pentyl viologen.

7. The device of claim 5, wherein the viologen forming a complex with the bromine moiety has the structure:

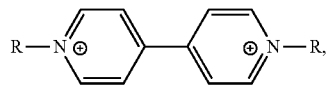

and
R is an alkyl having at least 4 carbons.

8. The device of claim 1, wherein the seal is a heat seal and the carbon-polymer composite is a thermoplastic.

9. The device of claim 8, wherein the separator and the plastic spacer are made from one component with a microporous polymer separator that has porosity collapse in the region of the heat-seal.

10. The device of claim 1, wherein the first and second walls are flexible and each have a thickness of 100 micrometers or less.

11. The device of claim 1, further comprising a compartment housing the first electrode, the second electrode, the separator, and the electrolyte permeating the electrodes and separator, wherein the compartment is bound above and below by the walls and on the edges by the inside of the plastic spacer.

12. The device of claim 1, comprising a plurality of the cells stacked on top of one another in a series configuration, wherein the positive current collector of one cell and the negative current collector of the adjacent cell are replaced by a single bipolar current collector made of the carbon-polymer composite.

13. The device of claim 1, wherein the first redox couple further comprises a complexing agent comprising a tetraalkylammonium that forms a complex with the bromine or the bromine moiety in the catholyte.

14. The device of claim 13, wherein the tetraalkylammonium is tetrabutylammonium bromide.

15. The device of claim 14, wherein:
the tetrabutylammonium bromide combines with the bromine moiety to form a [$TBA^+ \cdot Br_3^-$] solid complex retained in the pores of the porous carbon material of the electrode comprising a cathode.

16. The device of claim 1, wherein the electrolyte further comprises a complexing agent comprising a viologen that forms a complex with the bromine or the bromine moiety in the catholyte.

17. An energy storage device, comprising:
one or more cells, each cell including:
a pouch having a first wall and a second wall, the first wall and the second wall each comprising a current collector including a carbon-polymer composite; a plastic spacer, a first electrode, a second electrode , an electrolyte, and a separator inside the pouch; and
a seal between the first wall and the second wall so that the plastic spacer, the first electrode, the second electrode, the electrolyte, and the separator are sealed inside the pouch; and wherein:
the electrolyte includes zinc halide,
the electrodes comprise a cathode and an anode, the cathode comprising carbon, tetraalkylammonium complexing agent is pre-soaked on the carbon in the cathode, and
during charging, the zinc from the zinc halide plates onto the anode and the halogen in the halide oxidizes so as to form a solid complex with the tetraalkylammonium on the cathode.

18. The energy storage device of claim 17, wherein the carbon in the cathode is soaked with the tetraalkylammonium complexing agent and the tetraalkylammonium complexing agent is tetrabutylammonium bromide or cetyltrimethylammonium bromide.

19. The energy storage device of claim 17, wherein the electrolyte does not include a viologen.

* * * * *